US008206395B2

United States Patent
McLean et al.

(10) Patent No.: US 8,206,395 B2
(45) Date of Patent: Jun. 26, 2012

(54) SURGICAL INSTRUMENT AND METHOD FOR THE DISTRACTION OR COMPRESSION OF BONES

(75) Inventors: Scott McLean, Waterbury, CT (US); David Boisvert, Meriden, CT (US)

(73) Assignee: Spine Wave, Inc., Shelton, CT (US)

( * ) Notice: Subject to any disclaimer, the term of this patent is extended or adjusted under 35 U.S.C. 154(b) by 187 days.

(21) Appl. No.: 12/819,007

(22) Filed: Jun. 18, 2010

(65) Prior Publication Data

US 2011/0313477 A1 Dec. 22, 2011

(51) Int. Cl.
*A61B 17/70* (2006.01)

(52) U.S. Cl. ....................... 606/86 A; 606/99
(58) Field of Classification Search ............... 606/86 A, 606/90, 99, 105, 205–208, 279
See application file for complete search history.

(56) References Cited

U.S. PATENT DOCUMENTS

| | | |
|---|---|---|
| 4,238,339 A | 12/1980 | Khutoretsky et al. |
| 4,411,191 A | 10/1983 | Combeau |
| 4,411,259 A | 10/1983 | Drummond |
| 4,448,191 A | 5/1984 | Rodnyansky et al. |
| 4,657,001 A | 4/1987 | Fixel |
| 4,736,738 A | 4/1988 | Lipovsek et al. |
| 4,913,134 A | 4/1990 | Luque |
| 5,049,151 A | 9/1991 | Durham et al. |
| 5,092,866 A | 3/1992 | Breard et al. |
| 5,242,443 A | 9/1993 | Kambin |
| 5,263,953 A | 11/1993 | Bagby |
| 5,411,503 A | 5/1995 | Hollstien et al. |
| 5,439,464 A | 8/1995 | Shapiro |
| 5,458,608 A | 10/1995 | Wortrich |
| 5,741,261 A | 4/1998 | Moskovitz et al. |
| 5,814,072 A | 9/1998 | Bonutti |
| 5,897,574 A | 4/1999 | Bonutti |
| 5,902,231 A | 5/1999 | Foley et al. |
| 5,910,141 A | 6/1999 | Morrison et al. |
| 5,948,002 A | 9/1999 | Bonutti |
| 5,954,635 A | 9/1999 | Foley et al. |
| 5,961,538 A | 10/1999 | Pedlick et al. |
| 5,961,554 A | 10/1999 | Janson et al. |
| 6,090,113 A | 7/2000 | LeCouedic et al. |
| 6,102,934 A | 8/2000 | Li |
| 6,183,472 B1 | 2/2001 | Lutz |
| 6,188,472 B1 | 2/2001 | Gage et al. |
| 6,235,028 B1 | 5/2001 | Brumfield et al. |

(Continued)

OTHER PUBLICATIONS

Synthes Constellation CP System Surgical Technique Guide, ©2008 Synthes, Inc., West Chester, PA.

(Continued)

*Primary Examiner* — Eduardo C Robert
*Assistant Examiner* — Christina Negrelli
(74) *Attorney, Agent, or Firm* — Hoffmann & Baron, LLP

(57) ABSTRACT

A surgical instrument for the distraction or compression of bones or bone portions comprises a pair of elongate cross members pivotally coupled for relative movement having at one end a respective pair of handles and at the other end a respective pair of jaws. The jaws are generally parallel to each other and define a first plane within which the jaws are relatively movable, the space on both sides of the plane defining a work space between the jaws. The instrument further comprises a fulcrum supported by at least one of the cross members projecting into the work space and having an axis spaced from the jaws.

28 Claims, 56 Drawing Sheets

U.S. PATENT DOCUMENTS

| | | |
|---|---|---|
| 6,440,133 B1 | 8/2002 | Beale et al. |
| 6,530,926 B1 | 3/2003 | Davison |
| 6,530,929 B1 | 3/2003 | Justis et al. |
| 6,660,006 B2 | 12/2003 | Markworth et al. |
| D488,229 S | 4/2004 | Rinner et al. |
| 6,716,218 B2 | 4/2004 | Holmes et al. |
| 6,793,656 B1 | 9/2004 | Mathews |
| 6,802,844 B2 | 10/2004 | Ferree |
| 6,830,574 B2 | 12/2004 | Heckele et al. |
| 6,945,933 B2 | 9/2005 | Branch et al. |
| 7,008,422 B2 | 3/2006 | Foley et al. |
| 7,011,660 B2 | 3/2006 | Sherman et al. |
| 7,160,300 B2 | 1/2007 | Jackson |
| 7,179,261 B2 | 2/2007 | Sicvol et al. |
| 7,188,626 B2 | 3/2007 | Foley et al. |
| 7,250,052 B2 | 7/2007 | Landry et al. |
| 7,306,603 B2 | 12/2007 | Boehm, Jr. et al. |
| 7,420,279 B2 | 9/2008 | Ohnishi et al. |
| 7,465,306 B2 | 12/2008 | Pond, Jr. et al. |
| 7,473,267 B2 | 1/2009 | Nguyen et al. |
| 7,476,240 B2 | 1/2009 | Raymond et al. |
| 7,491,208 B2 | 2/2009 | Pond, Jr. et al. |
| 7,491,218 B2 | 2/2009 | Landry et al. |
| 7,497,869 B2 | 3/2009 | Justis |
| 7,520,879 B2 | 4/2009 | Justis et al. |
| 7,527,638 B2 | 5/2009 | Anderson et al. |
| 7,563,264 B2 | 7/2009 | Landry et al. |
| 7,572,276 B2 | 8/2009 | Lim et al. |
| 7,588,575 B2 | 9/2009 | Colleran et al. |
| 7,588,588 B2 | 9/2009 | Spitler et al. |
| 7,597,694 B2 | 10/2009 | Lim et al. |
| 7,618,442 B2 | 11/2009 | Spitler et al. |
| 7,648,506 B2 | 1/2010 | McCord et al. |
| 7,648,507 B2 | 1/2010 | Techiera et al. |
| 7,648,521 B2 | 1/2010 | Hestad |
| 7,666,188 B2 | 2/2010 | Anderson et al. |
| 7,666,189 B2 | 2/2010 | Gerber et al. |
| 7,686,814 B2 | 3/2010 | Lim et al. |
| 7,708,763 B2 | 5/2010 | Selover et al. |
| 7,758,584 B2 | 7/2010 | Bankoski et al. |
| 7,758,617 B2 | 7/2010 | Iott et al. |
| 2002/0161268 A1 | 10/2002 | Lee et al. |
| 2003/0208203 A1 | 11/2003 | Lim et al. |
| 2004/0138662 A1 | 7/2004 | Landry et al. |
| 2005/0065517 A1 | 3/2005 | Chin |
| 2005/0080418 A1 | 4/2005 | Simonson et al. |
| 2005/0131422 A1 | 6/2005 | Anderson et al. |
| 2005/0154389 A1 | 7/2005 | Selover et al. |
| 2005/0228380 A1 | 10/2005 | Moore et al. |
| 2005/0245928 A1 | 11/2005 | Colleran et al. |
| 2005/0277934 A1 | 12/2005 | Vardiman |
| 2006/0084993 A1 | 4/2006 | Landry et al. |
| 2006/0111714 A1 | 5/2006 | Foley |
| 2006/0142761 A1 | 6/2006 | Landry et al. |
| 2006/0200135 A1 | 9/2006 | Sherman et al. |
| 2006/0229614 A1 | 10/2006 | Foley et al. |
| 2006/0247630 A1 | 11/2006 | Iott et al. |
| 2006/0264942 A1 | 11/2006 | Lim et al. |
| 2006/0264962 A1 | 11/2006 | Chin et al. |
| 2006/0276803 A1 | 12/2006 | Salerni |
| 2007/0016198 A1 | 1/2007 | Boehm, Jr. et al. |
| 2007/0016199 A1 | 1/2007 | Boehm, Jr. et al. |
| 2007/0078460 A1 | 4/2007 | Frigg et al. |
| 2007/0167954 A1 | 7/2007 | Sicvol et al. |
| 2007/0173745 A1 | 7/2007 | Diederich et al. |
| 2007/0185491 A1 | 8/2007 | Foley et al. |
| 2007/0198015 A1 | 8/2007 | Foley et al. |
| 2007/0233097 A1 | 10/2007 | Anderson et al. |
| 2008/0009864 A1 | 1/2008 | Forton et al. |
| 2008/0039838 A1 | 2/2008 | Landry et al. |
| 2008/0051787 A1 | 2/2008 | Remington et al. |
| 2008/0077135 A1 | 3/2008 | Stad et al. |
| 2008/0077139 A1 | 3/2008 | Landry et al. |
| 2008/0125788 A1 | 5/2008 | Cohen et al. |
| 2008/0208258 A1 | 8/2008 | Foley et al. |
| 2008/0312703 A1 | 12/2008 | Hestad et al. |
| 2008/0319477 A1 | 12/2008 | Justis et al. |
| 2009/0005814 A1 | 1/2009 | Miller et al. |
| 2009/0082666 A1 | 3/2009 | Geist et al. |
| 2009/0082811 A1 | 3/2009 | Stad et al. |
| 2009/0099172 A1 | 4/2009 | Cai et al. |
| 2009/0105774 A1 | 4/2009 | Jones et al. |
| 2009/0138056 A1 | 5/2009 | Anderson et al. |
| 2009/0143828 A1 | 6/2009 | Stad et al. |
| 2009/0149892 A1 * | 6/2009 | Stad et al. .................. 606/86 A |
| 2009/0182382 A1 | 7/2009 | Justis et al. |
| 2009/0264930 A1 | 10/2009 | Mcbride |
| 2009/0312797 A1 | 12/2009 | Lim et al. |
| 2010/0004695 A1 * | 1/2010 | Stad et al. .................. 606/86 A |
| 2010/0024487 A1 | 2/2010 | Khoo et al. |
| 2010/0030283 A1 | 2/2010 | King et al. |
| 2010/0036443 A1 | 2/2010 | Hutton et al. |
| 2010/0069972 A1 | 3/2010 | Jones et al. |
| 2010/0094359 A1 | 4/2010 | Techiera et al. |
| 2010/0137915 A1 | 6/2010 | Anderson et al. |
| 2010/0145348 A1 | 6/2010 | Marino |
| 2010/0145349 A1 | 6/2010 | Lim et al. |
| 2010/0145389 A1 | 6/2010 | Triplett et al. |
| 2010/0174326 A1 | 7/2010 | Selover et al. |
| 2010/0331849 A1 | 12/2010 | Riesinger et al. |
| 2011/0166610 A1 | 7/2011 | Altarac et al. |

OTHER PUBLICATIONS

Synthes Cannulated Pangea System Technique Guide, ©2007 Synthes Inc., Westchester, PA.
Mark Peterson, M.D., Frank Phillips, M.D. and William Taylor, M.D., NuVasive DBR Technique Guide, ©2005 NuVasive, Inc., San Diego, California.
Abbott PathFinder Surgical Technique Guide, Oct. 2008, 1199-0005-MKC Rev H per DCR 6005, Austin Texas.
Kevin T. Foley, M.D., Medtronic Sextant Technique Guide, © 2002 Medtronic Sofamor Danek, Memphis TN.
D. Greg Anderson, M.D., Robert Heary, M.D., Carl Lauryssen, M.D., and Tony Tannoury, M.D., DePuy-Viper2 Surgical Technique Guide, May, 2008, MIO4-03-000, JC/UM, Raynham, MA.
Biomet Ballista Surgical Technique Guide, Copyright 2008 Bioment, Inc., Parisppany, NJ.

* cited by examiner

SURGICAL INSTRUMENT AND METHOD FOR THE DISTRACTION OR COMPRESSION OF BONES

BACKGROUND

The present disclosure contemplates instrumentation and procedures for achieving spinal fixation or more particularly for percutaneously introducing a spinal fixation system into a patient.

A typical spinal fixation system 10 as shown in FIG. 1 spans between successive vertebrae V of the spine. An elongated member, such as rod 12, extends along the length of the spine and provides an anchor point for connecting each vertebra to the rod. The rod is typically contoured to approximate the normal curvature of the spine for the particular instrumented spinal segments, which may include lordosis or kyphosis. Anchor devices 15 are provided for connecting the vertebral segments to the elongated member. These anchor devices may include hooks, bolts, screws or other means for engaging a vertebra. For the purposes of the present discussion, the anchor device 15 is a bone screw assembly, such as the screw assembly shown in FIG. 2. However, it should be appreciated that the instrumentation and procedures disclosed herein may be implemented with other types of anchor devices, such as a hook engaged to the lamina of a vertebra for instance.

The bone engaging fastener or screw assembly 15 includes a shank 16 that carries threads configured to engage vertebral bone. For instance, the fastener is a pedicle screw with a shank that is threaded for engagement within the pedicle of the vertebra. The screw assembly further includes a head 16a by which the screw, and ultimately the vertebra, is fastened to the spinal rod 12. In particular, the head 16a supports a yoke 17 that is generally U-shaped to receive the spinal rod therethrough, as depicted in FIG. 2. The rod 12 may be supported in part by a collar 18 mounted over the head 16a of the bone screw. A cap 19 carries a set screw 20 that locks the rod within the yoke 17 and thus fastens the rod 12 to the bone screw.

One embodiment of a bone screw assembly 15 is disclosed in co-pending U.S. application Ser. No. 11/762,898 (the '898 application), entitled "Multi-Axial Fixation Assembly", field on Jun. 14, 2007 and published as No. 2008/0119858, the disclosure of which is incorporated herein by reference. For the purposes of the present disclosure, the bone screw 15 may be constructed as disclosed in the '898 application, although it is understood that other bone screw or multi-axial fastener configurations may be implanted using the instruments and procedures disclosed herein. In the multi-axial bone screw assembly 15 the yoke 17 is articulatingly attached to the threaded bone screw 16, and more specifically to the head 16a of the bone screw, so that the yoke 17 can adopt a range of spherical angles relative to the bone screw. Thus, the yoke can articulate relative to the bone screw fastened in the vertebra so that the slot 42 can be aligned to receive the connecting rod 25.

While in the past spinal fixation systems have been implanted in open procedures involving relatively large incisions through the patient's tissue with significant muscle retraction, more recent procedures have been developed to percutaneously introduce spinal fixation systems in a minimally invasive manner. One technique known as the Sextant® System is described in U.S. Pat. No. 6,530,929, issued to Justis, et al. In the '929 patent, separate incisions are made for introducing respective pedicle screws each attached to a tubular extension extending outwardly from the patient through each incision. A pivot arm coupled to the extensions introduces an elongate rod through another separate incision remote from the incisions receiving the extensions. The pivot arm urges the rod beneath the skin and into the pedicle screws for fixation. Other percutaneous systems such as that shown in U.S. Pat. No. 7,306,603 issued to Boehm, Jr. et al. utilize tubular pedicle screw extensions to place a rod longitudinally through the extension into one of the pedicle screws. The rod is then pivoted about the pedicle screw through an incision between the pedicle screws to the second pedicle screw. Others still employ systems such as that shown in U.S. Pat. No. 7,250,052 issued to Landry et al. wherein slots in the screw extensions are used to guide a rod between the extensions through a single incision into position in two or more pedicle screws.

Nevertheless, there is current desire for minimally invasive instruments and procedures for the percutaneous placement of spinal fixation systems that are relatively simple and easy to use and that provide for enhanced assurance of rod introduction and connection to the spinal implants.

SUMMARY

A surgical instrument for the distraction or compression of bones or bone portions comprises a pair of elongate cross members pivotally coupled for relative movement having at one end a respective pair of handles and at the other end a respective pair of jaws. The jaws are generally parallel to each other and define a first plane within which the jaws are relatively movable, the space on both sides of the plane defining a work space between the jaws. The instrument further comprises a fulcrum supported by at least one of the cross members projecting into the work space and having an axis spaced from the jaws.

In another aspect, a method of selectively compressing or distracting bones or bone portions during surgery comprises the steps of: providing a surgical instrument having a pair of jaws operably movable relative to each other in a first plane, the space on both sides of the plane and between the jaws defining a work space, the instrument including a fulcrum projecting into the work space and having an axis spaced from the jaws; and operating the jaws with the instrument selectively being in a first position or a second position, the fulcrum in the first instrument position being in a first orientation to cause compression, the second instrument position being the inverse of the first instrument position, the fulcrum in the second position being in a second orientation to cause distraction.

In another aspect, a method of selectively compressing or distracting vertebral bodies in a patient during percutaneous surgery comprises the steps of: providing a surgical instrument having a pair of jaws operably movable relative to each other in a first plane, the space on both sides of the plane and between the jaws defining a work space, the instrument including a fulcrum projecting into the work space and having an axis spaced from the jaws; coupling a pair of elongate extensions to one each of respective vertebral bodies of the spine, the extensions each having a length to project outwardly of the exterior surface of the patient; inserting the fulcrum between and in a direction generally transverse to the longitudinal axis of the extensions with the jaws disposed exteriorly of the extensions; and operably moving the jaws relatively toward each other to contact the extensions and pivot the extensions about the fulcrum to cause one of compression and distraction of said vertebral bodies.

DETAILED DESCRIPTION

Figure 2:
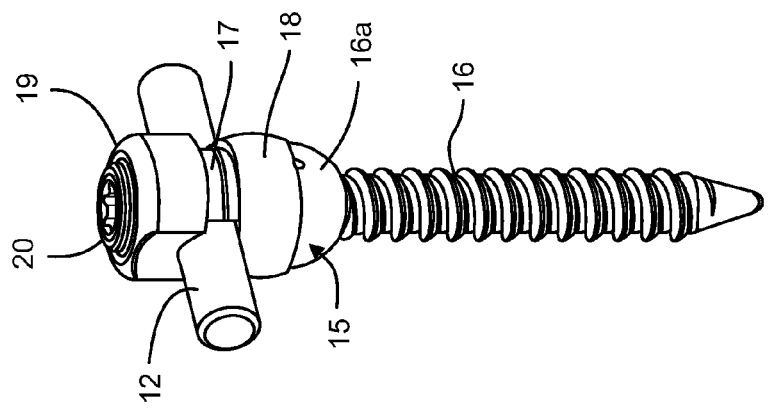
FIG. 2 is a perspective view of a bone engaging fastener in the form of a pedicle screw suitable for use with the instrumentation and procedures disclosed herein.
Figure 1:
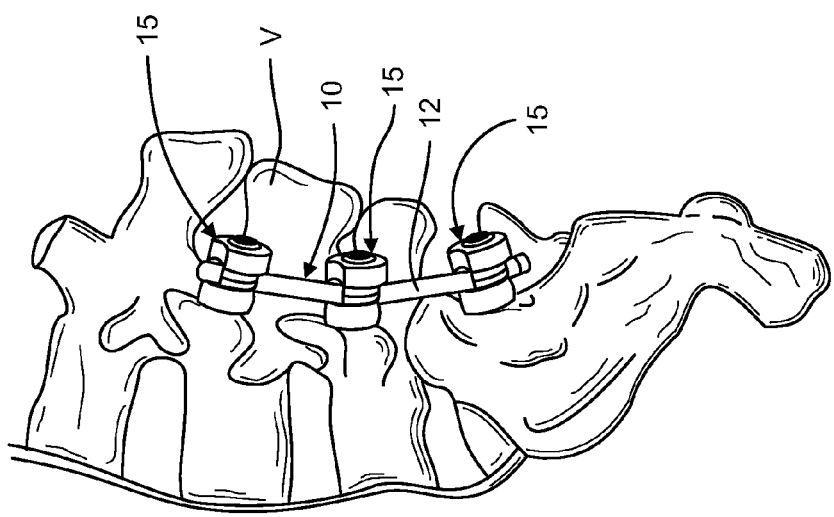
FIG. 1 is a representation of a portion of a patient's spine instrumented with a multi-level fixation system.

For the purposes of promoting an understanding of the principles of the invention, reference will now be made to the embodiments illustrated in the drawings and described in the following written specification. It is understood that no limitation to the scope of the invention is thereby intended. It is further understood that the present invention includes any alterations and modifications to the illustrated embodiments and includes further applications of the principles of the invention as would normally occur to one skilled in the art to which this invention pertains.

Figure 3:
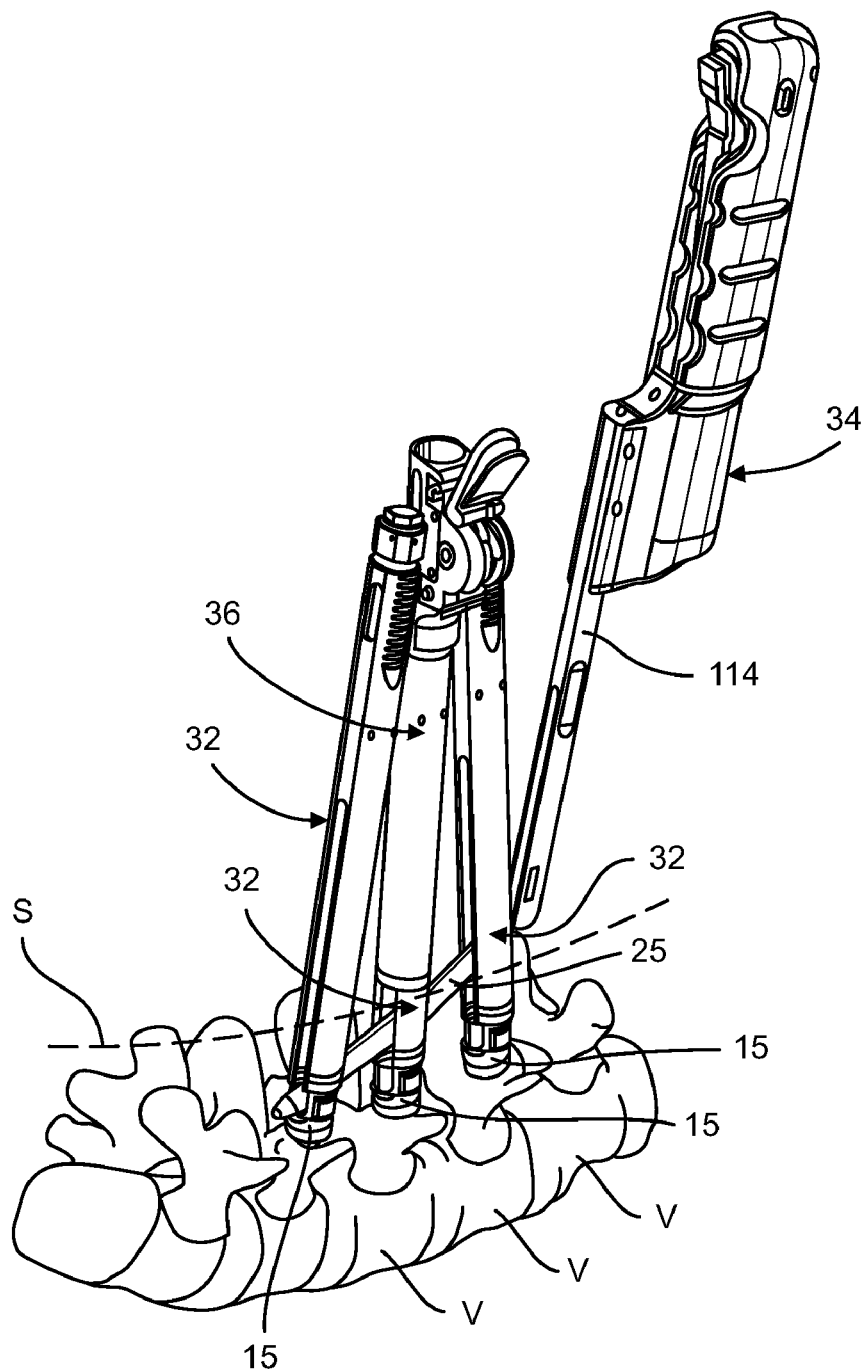
FIG. 3 is a perspective view of instrumentation disclosed herein used to introduce an elongated connecting element to a fixation assembly.
Figure 4:
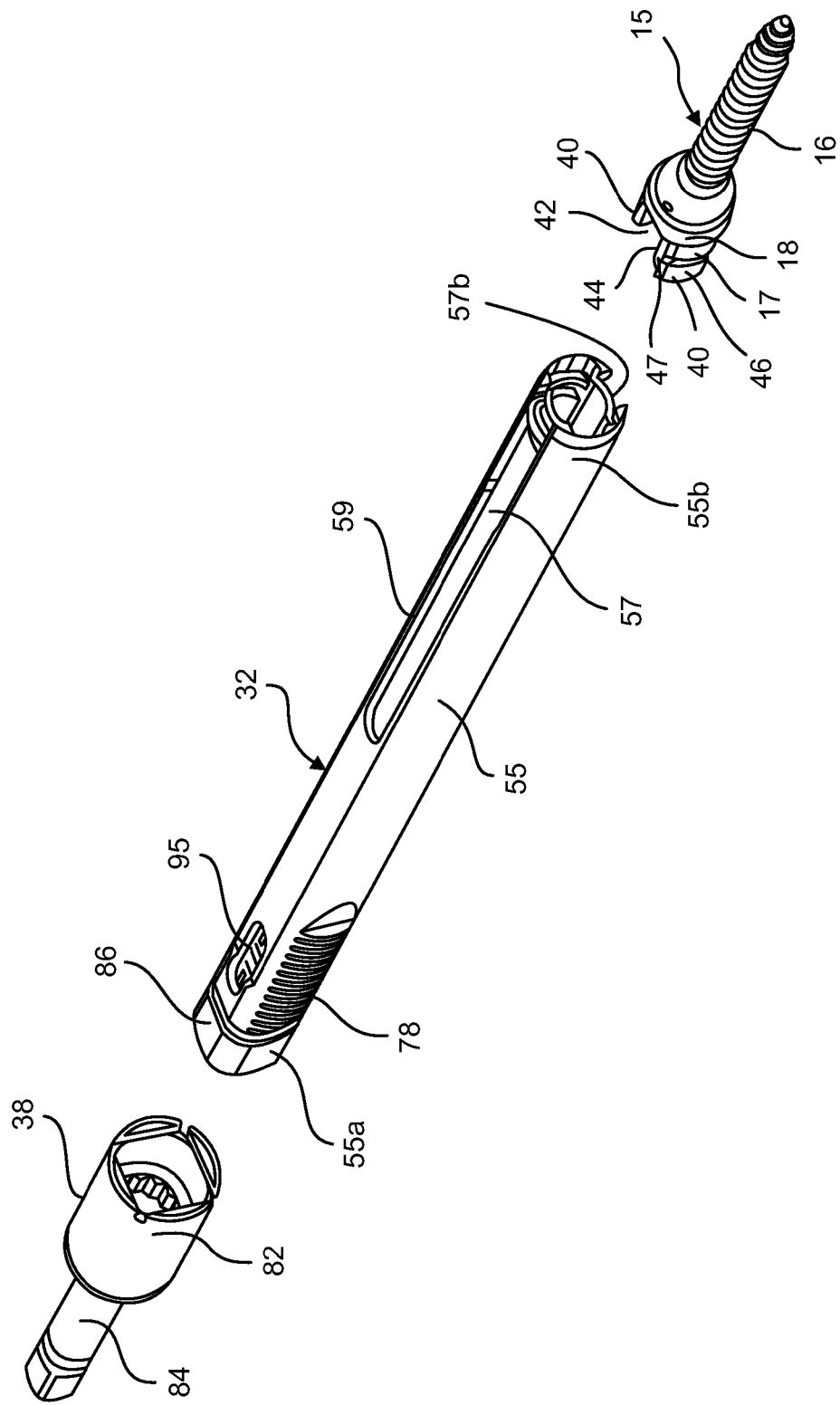
FIG. 4 is an exploded perspective view of a bone screw and a screw extension assembly disclosed herein.

Referring to FIGS. 3 and 4, certain components of the instrumentation disclosed herein are depicted as used according to certain procedures disclosed herein. In particular, three bone screw assemblies 15 are engaged to three vertebrae V in preparation for a multi-level fixation of the spine. An elongate connecting member, such as connecting rod 25, is configured to be received within the yokes 17 of each of the screw assemblies to connect each of the vertebral levels in a conventional manner. When the construct is complete, the rod will be locked to each of the screw assemblies, such as by the cap 19 and set screw 20 illustrated in FIG. 2. As shown in FIG. 3, each of the screw assemblies 15 carries a screw extension assembly 32 that is sized to be accessible outside the patient's skin. The patient's skin or fascia is depicted as a phantom line S for illustrative purposes only, with the understanding that the level of the fascia relative to the fixation location on the vertebral bodies will vary from patient to patient. The instruments further include a rod introducer assembly 34 that is used to introduce the connecting rod 25 through and into the yokes 17 of each of the bone screw assemblies 15. Once the rod is situated within the bone screw yokes, a rod persuader assembly 36 may be used to fully seat the rod therein for final tightening. The nature and manner of operation of these and other instruments are described herein.

Screw Extension Assembly

Details of the screw extension assembly 32 and its interface with the bone screw assembly 15 will be explained with reference to FIGS. 4-17. Looking first at the bone screw assembly 15, and particularly at FIGS. 4-7, the yoke 17 includes opposed upstanding arms 40 that are separated to define a slot 42 therebetween. The slot 42 is sized and configured to relatively snugly receive the connecting rod 25 therein. For some bone screw assemblies, the connecting rod may be seated within a U-shaped base of the slot 42. For the present disclosure, the connecting rod is seated on the sleeve 18 rather than at the base of the yoke slot, all in accordance with the bone screw assembly disclosed in the '898 application incorporated by reference above.

Figure 6:
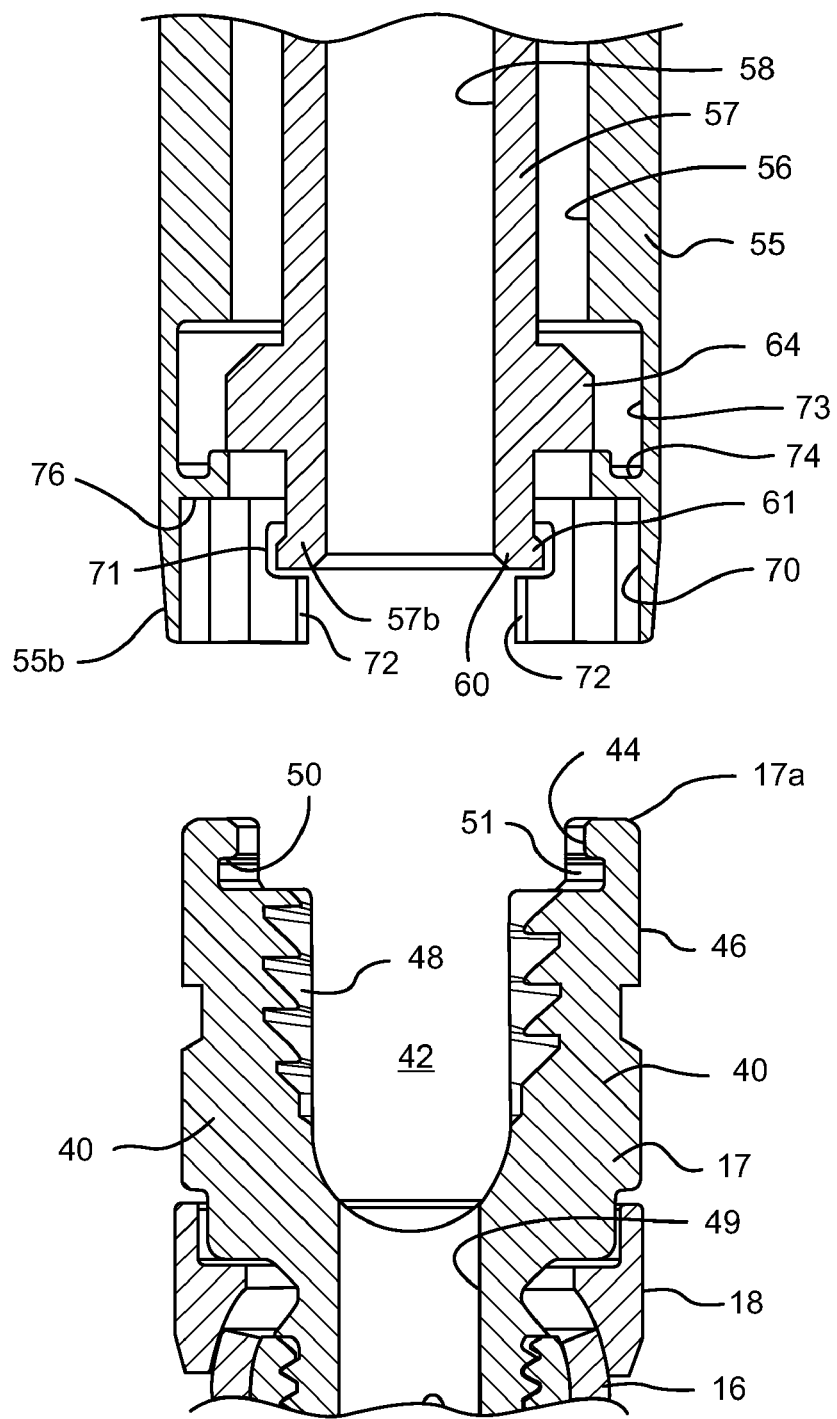
FIG. 6 is a cross-sectional view of the bone screw and screw extension assembly shown in FIG. 5 with the screw extension assembly in a first position.

The arms 40 of the yoke 17 include facing interior surfaces 44 which define internal threads 48, as best seen in FIG. 6. The threads 48 are configured to mate with the set screw 20 to clamp the connecting rod 25 within the yoke and for final fixation of the bone screw assembly, as described in the '898 application. The upstanding arms 40 further include an exterior surface 46 that is partially cylindrical and flat side surfaces 47 on opposite sides of the slot 42. The yoke further defines a tool bore 49 aligned with a tool recess 22 at the base of the bone screw head 16a that is used to drive the bone screw 16 into the vertebral bone.

As thus far described, the yoke 17 is generally similar to the yokes of other bone screw assemblies, including the bone screw described in the '898 application. In the embodiment disclosed herein, the interior surface 44 of the yoke 17 defines an undercut 50 that forms a coupling surface 51 at the mouth of the slot 42, as best seen in FIG. 6. The coupling surface 51 provides an interface for coupling to the screw extension assembly 32.

Figure 7:
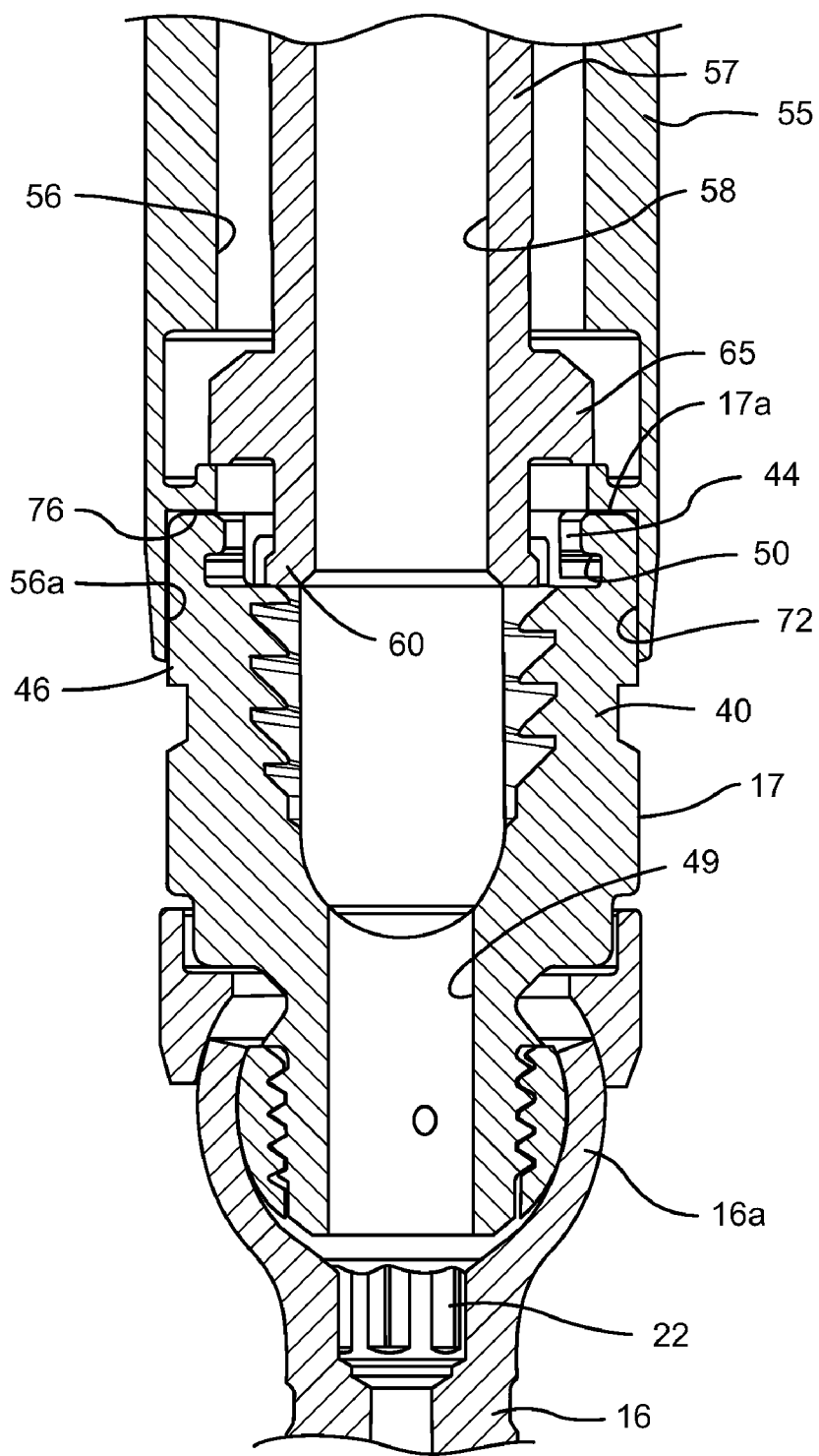
FIG. 7 is a cross-sectional view of the bone screw and screw extension assembly shown in FIG. 6 with the screw extension assembly mounted on the bone screw in the first position.

The pedicle screw extension assembly 32 includes an elongate hollow outer sleeve 55 having a perimetric sidewall that defines a bore 56 extending from a proximal end 55a to a distal end 55b. A lower bore portion 56a of the bore adjacent the distal end 55b is sized to be relatively snugly received about the exterior surface 46 of the yoke 17 as shown in FIG. 7. The outer sleeve further defines a slot 59 through the sleeve sidewall adjacent the distal end 55b of the sleeve and extending across the diameter of the sleeve, as shown in FIG. 4. The slot 59 is sized to receive a connecting rod 25 therethrough as depicted in FIG. 3. The slot 59, which opens through the distal end 55b, may be long enough proximally in certain embodiments to extend above the fascia S so that the connecting rod 25 may be introduced into the screw extension assembly 32 outside the patient, as explained in more detail herein.

Returning to FIGS. 5, 6, the extension assembly also includes an elongate hollow inner sleeve 57 concentrically and rotatably disposed within the bore 56 of the outer sleeve 55. The inner sleeve has a perimetric sidewall that defines a central bore 58 from a proximal end 57a (see FIG. 13) to a distal end 57b that is configured for passage of other instruments as described herein. The inner sleeve further defines a slot 67 opening through the sleeve sidewall at the distal end 57b of the inner sleeve that is generally coincident in length and width with the slot 59 of the outer sleeve. The inner sleeve 57 is rotatable relative to the outer sleeve 55 between a first position shown in FIG. 5 in which the inner sleeve 57 essentially covers or closes the slot 59 in the outer sleeve, and a second position illustrated in FIG. 8 in which the two slots 59 and 67 are aligned so that a connecting rod can be pass through the screw extension assembly 32.

Figure 5:
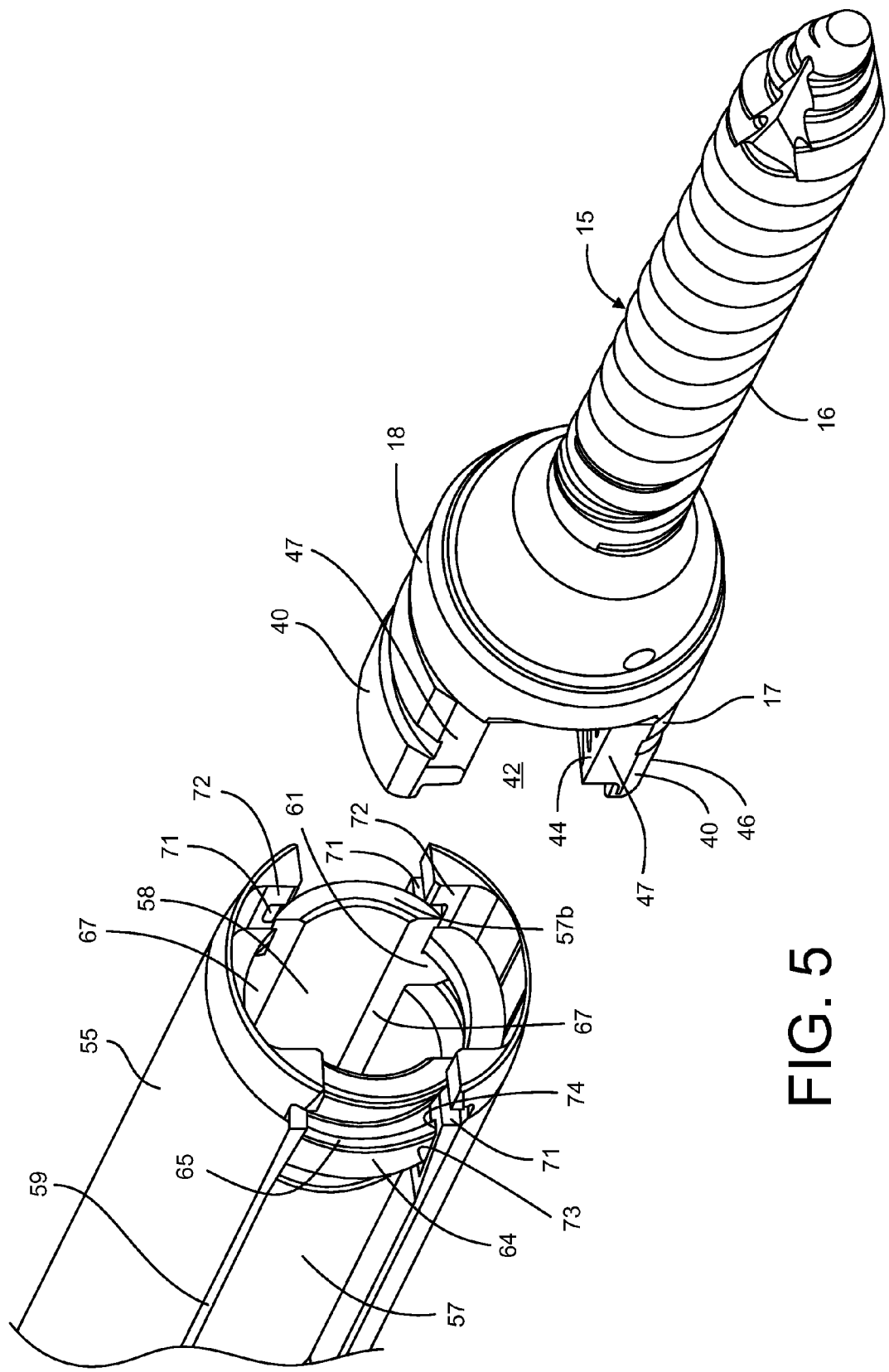
FIG. 5 is an enlarged view of the bone screw and the distal end of the screw extension assembly shown in FIG. 4.

FIGS. 5-11 show the screw extension assembly 32 in various stages of relative movement between the outer and inner sleeves 55, 57 to engage the yoke 17 of the bone screw assembly 15. In FIGS. 5 and 6, the screw assembly 15 is shown just prior to contact with the screw extension assembly. The outer and inner sleeves are in the first position described above in which the inner sleeve 57 covers or closes the slot 59 in the outer sleeve 55. The yoke 17 of the bone screw assembly is aligned so that the upstanding arms 40 are aligned with the slot 58 in the inner sleeve 57. The flat side faces 47 are thus aligned to pass into the slot 58 in a close fit.

In FIG. 7 the yoke 17 is fully seated within the screw extension assembly 32. More specifically, the proximal end 17a of the yoke is seated against the yoke mating surface 76 at the base of the lower bore portion 56a of the bore 56 in the outer sleeve 55. This lower portion 56*a* may further define flat surfaces 72 to align the flat side faces 47 of the yoke 17 as the yoke advances into the lower bore portion 56*a*. It can thus be appreciated that once the yoke 17 is fully seated within the lower bore portion 56*a* of the outer sleeve the yoke and outer sleeve will rotate and pivot together. More importantly, the outer sleeve will hold the yoke while the inner sleeve rotates relative to both components to firmly engage and lock the yoke to the screw extension assembly.

Figure 8:
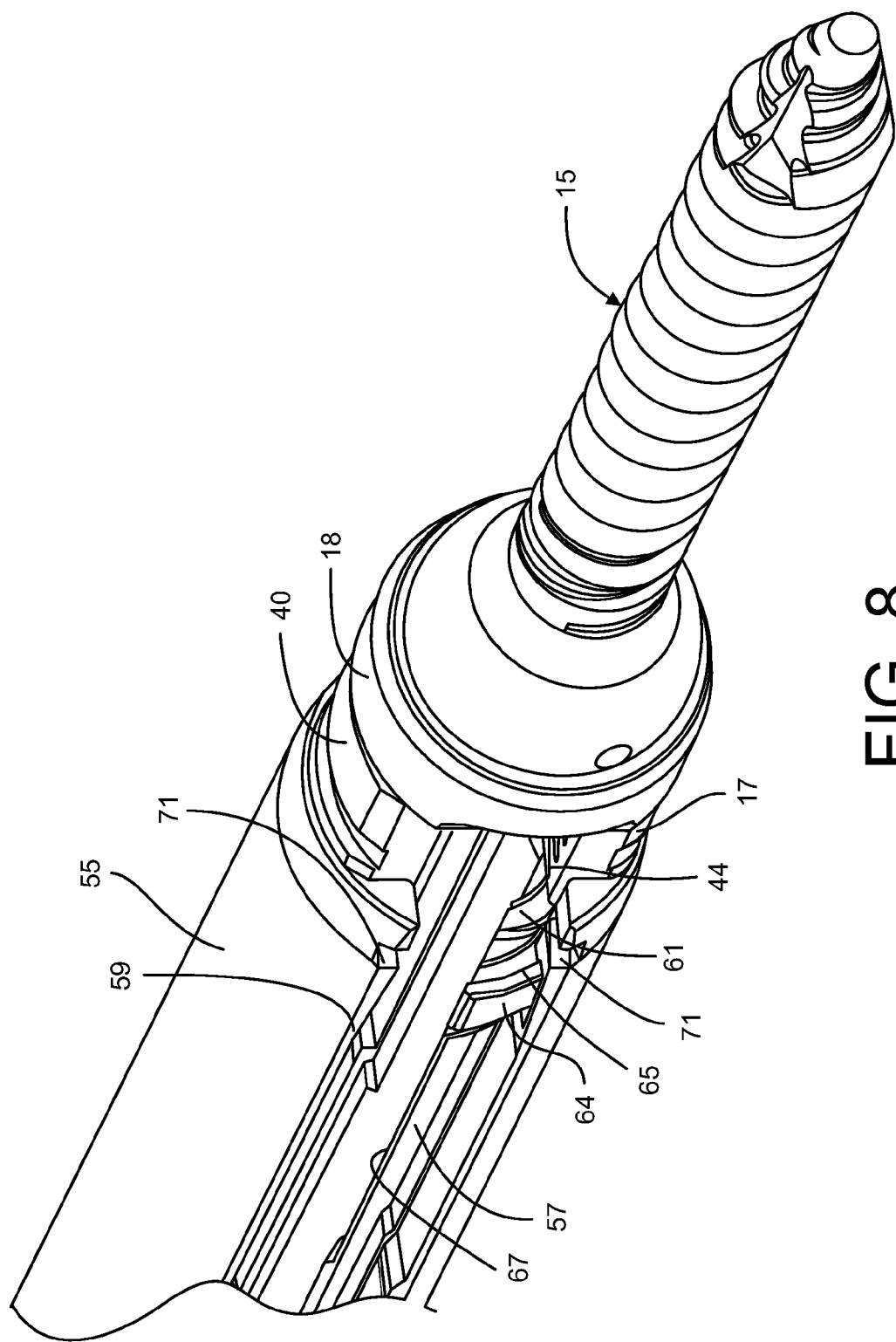
FIG. 8 is a perspective view of the bone screw and screw extension assembly shown in FIG. 7.
Figure 9:
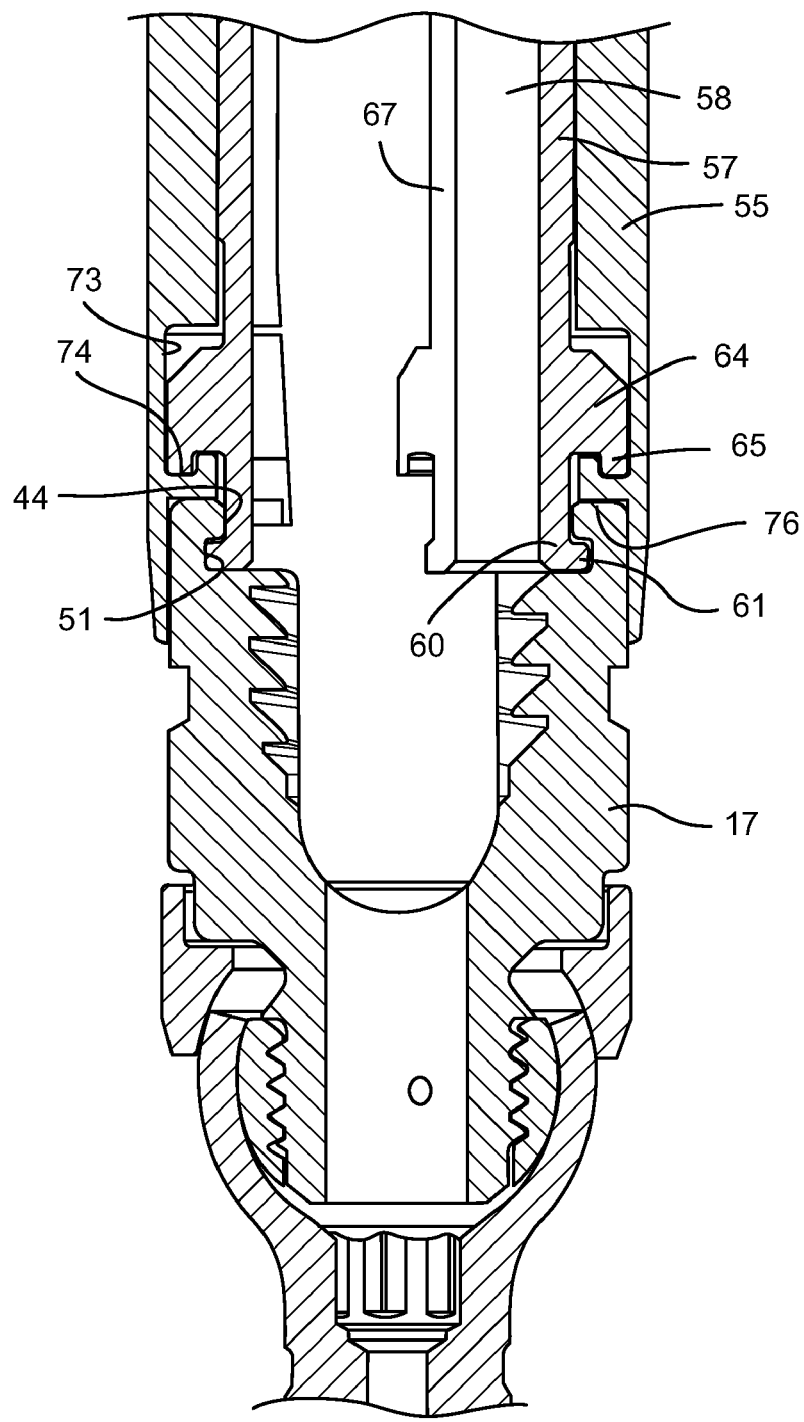
FIG. 9 is an enlarged cross-sectional view of the bone screw and screw extension assembly shown in FIG. 4 with the screw extension assembly mounted on the bone screw in a second position.
Figure 10:
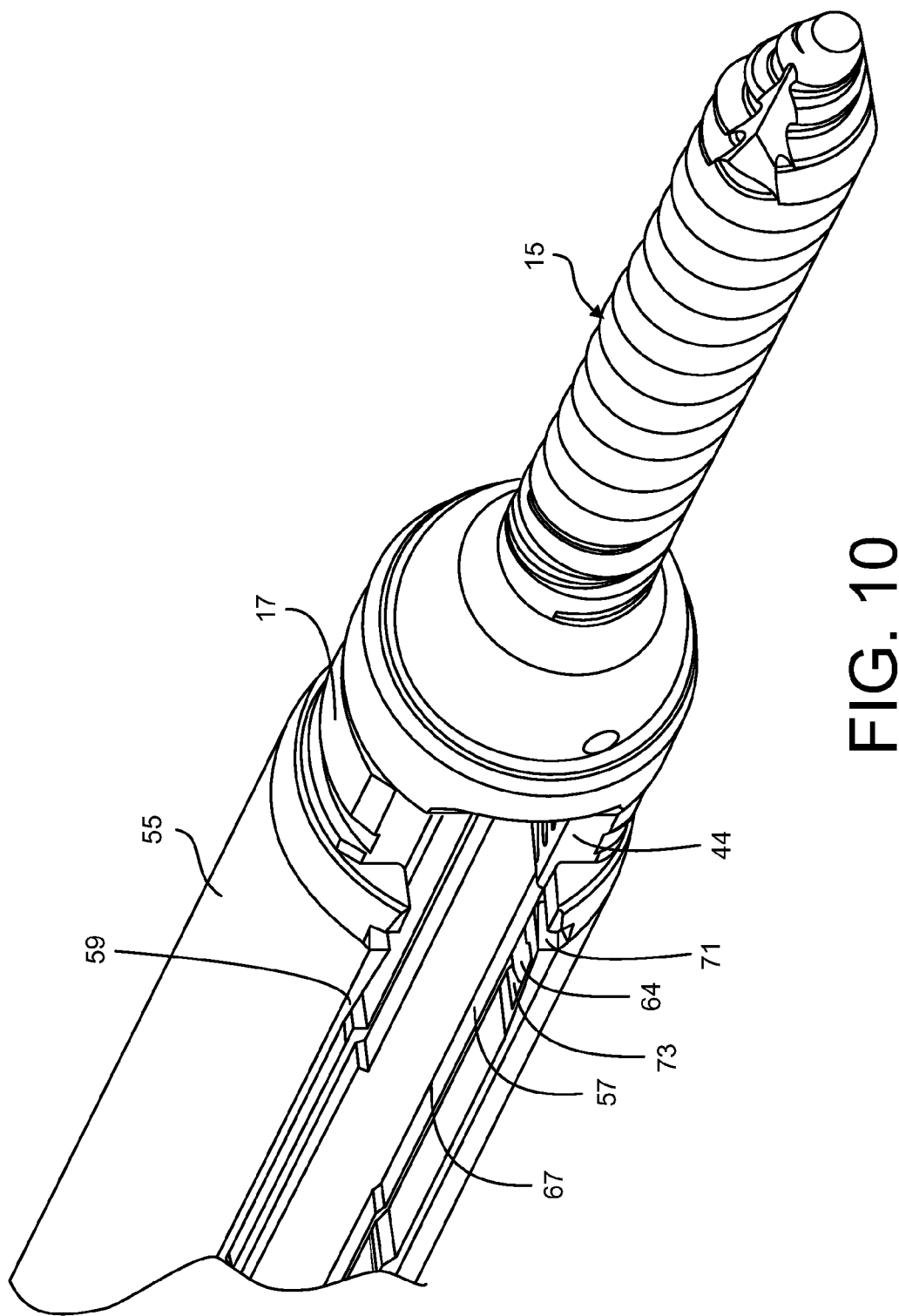
FIG. 10 is a perspective view of the bone screw and screw extension assembly shown in FIG. 9.
Figure 11:
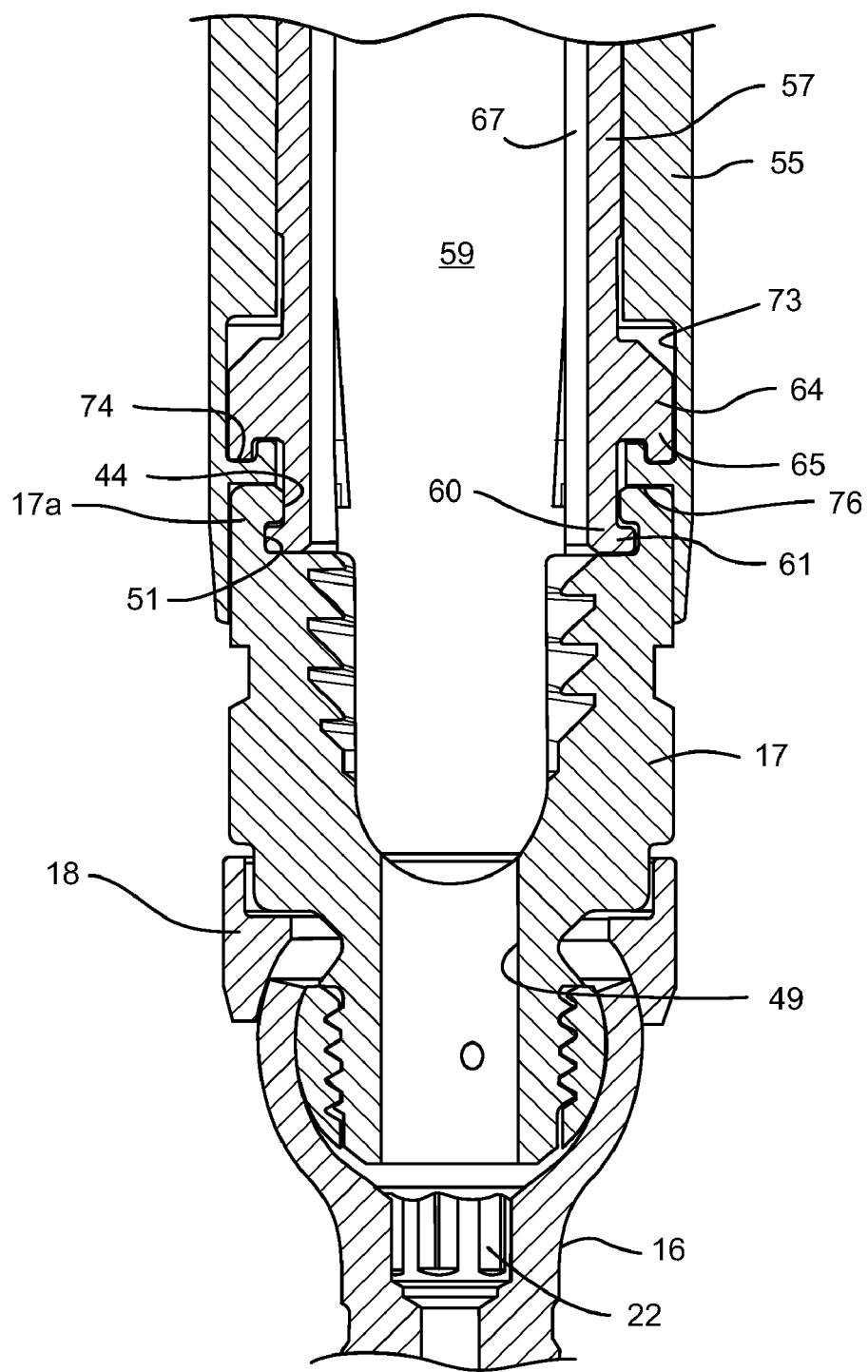
FIG. 11 is an enlarged cross-sectional view of the bone screw and screw extension assembly shown in FIG. 4 with the screw extension assembly mounted on the bone screw in a third position.

In order to effect this engagement, the inner sleeve 57 is provided with a yoke engagement member 60 at the distal end 57*b* of the sleeve. The yoke engagement member 60 includes generally radially outwardly directed flanges 61 that interface with coupling surfaces 51 defined by undercuts 50 at the proximal end 17*a* of the yoke, as seen in FIG. 6. As shown in FIG. 7, when the yoke is seated within the outer sleeve, the yoke engagement member 60 of the inner sleeve 57 is aligned with the coupling surfaces 51 of the yoke 17. The radial flanges 61 are initially situated within flange recesses 71 defined in the outer sleeve 55. From this position the inner sleeve 57 may be rotated relative to the outer sleeve 55 and to the yoke 17 connected to the outer sleeve. The effect of this relative rotation is illustrated in FIGS. 8-11. In FIGS. 8-9 the inner sleeve 57 is shown at the beginning of this relative rotation. As best seen in FIG. 9, as the inner sleeve rotates the radial flanges 61 are guided by the flange recesses 71 beneath the undercuts 50 and into engagement with the coupling surfaces 51 of the yoke proximal end 17*a*. The radial flanges 61 and the undercuts 50 are configured so that continued rotation of the inner sleeve relative to the yoke tends to pull the yoke upward or proximally toward the yoke mating surface 76 of the outer sleeve, as shown in FIGS. 10-11. In this position the rod slots 59 and 67 are aligned and the screw extension assembly is essentially supported by the bone screw assembly, which is itself subsequently anchored to the vertebra. The yoke engaging flange 61 and undercut 50 may be configured to provide a tighter fit as the inner sleeve is rotated relative to the outer sleeve. This may be accomplished, for instance, by increasing the thickness of the radial flange 61 radially outwardly in an upward angle and forming the undercut 50 to have a complementary configuration to accommodate the increased thickness of the radial flange 61 around the circumference of the coupling surface.

The screw extension assembly 32 may incorporate additional features to ensure a tight engagement between the extension assembly and the bone screw assembly 15 or yoke 17. Referring to FIGS. 5 and 9, the inner sleeve 57 may incorporate a securement member 64 that is configured to engage a securement recess 73 in the outer sleeve 55. The securement member may include a downwardly or distally projecting securement flange 65 that is received within an upwardly opening flange groove 74, as best seen in FIG. 9. Like the interface between the yoke engaging flange 61 and undercut 50, the securement flange 65 and flange groove 74 may be configured to provide a tighter fit as the inner sleeve 57 is rotated relative to the outer sleeve 55. Thus, the width of the flange 65 may be increased along the circumference or the width of the groove 74 decreased along the circumference so that the fit becomes tighter as the inner sleeve approaches the second position shown in FIG. 11. Upon rotation of the outer and inner sleeves 55, 57, securement flange 65 extending into flange groove 74 also serves to minimize or prevent outward radial splaying of the outer and inner sleeves 55, 57.

The combination of the yoke engaging member 60 and the securement member 64 of the inner sleeve and the interface of these elements to the yoke and outer sleeve, respectively, allows the screw extension assembly 32 to be firmly fastened to the yoke 17 and screw assembly 15 when the bone screw 16 is threaded into a vertebra. The screw extension assembly 32 may be manipulated or articulated relative to the bone screw 16. The rod slots 59 and 67 will thus always be aligned with the slot 42 in the yoke 17 of the bone screw assembly to facilitate placement of the connecting rod 25, as described herein.

In the illustrated embodiment, the yoke engagement member 60 incorporates a radially inwardly directed flange 61 while the yoke 17 incorporates a radially formed coupling surface 51 and undercut 50. Alternatively, these features may be reversed between the inner sleeve and yoke so that the yoke 17 incorporates a radially outwardly directed flange that mates with a radially inwardly formed groove in the distal end 55*b* of the inner sleeve 55. Similarly, the securement member 64 of the inner sleeve 57 and the securement recess 73 of the outer sleeve 55 may be reversed or re-oriented.

As thus far described it can be seen that the operation of the screw extension assembly 32 relies upon rotation of the inner sleeve relative to the outer sleeve. In one aspect of the assembly 32, the proximal end 55*a* of the assembly is configured to accept a socket driver 38, as shown in FIG. 4. The structure and operation of the socket driver is shown in more detail in FIGS. 12-17. The socket driver 38 includes a generally cylindrical socket 80 with a driver socket 82 formed in the base of the rectangular socket and a generally rectangular rim 81 formed at the distal opening of the cylindrical socket 80. A spindle 84 is provided for connection to a driving tool for rotating the socket driver 38 or to provide a gripping interface to manually rotate the socket driver. The rectangular rim 81 is configured to engage the generally rectangular outer surface 86 at the proximal end 55*a* of the outer sleeve 55. When the rim 81 is in contact with the outer surface 86 the socket driver 38 cannot be rotated relative to the outer sleeve 55. In the illustrated embodiment the mating surfaces of the rim and outer surface are generally rectangular, although other configurations are contemplated that prevent relative rotation between the socket driver and the outer sleeve.

Figure 14:
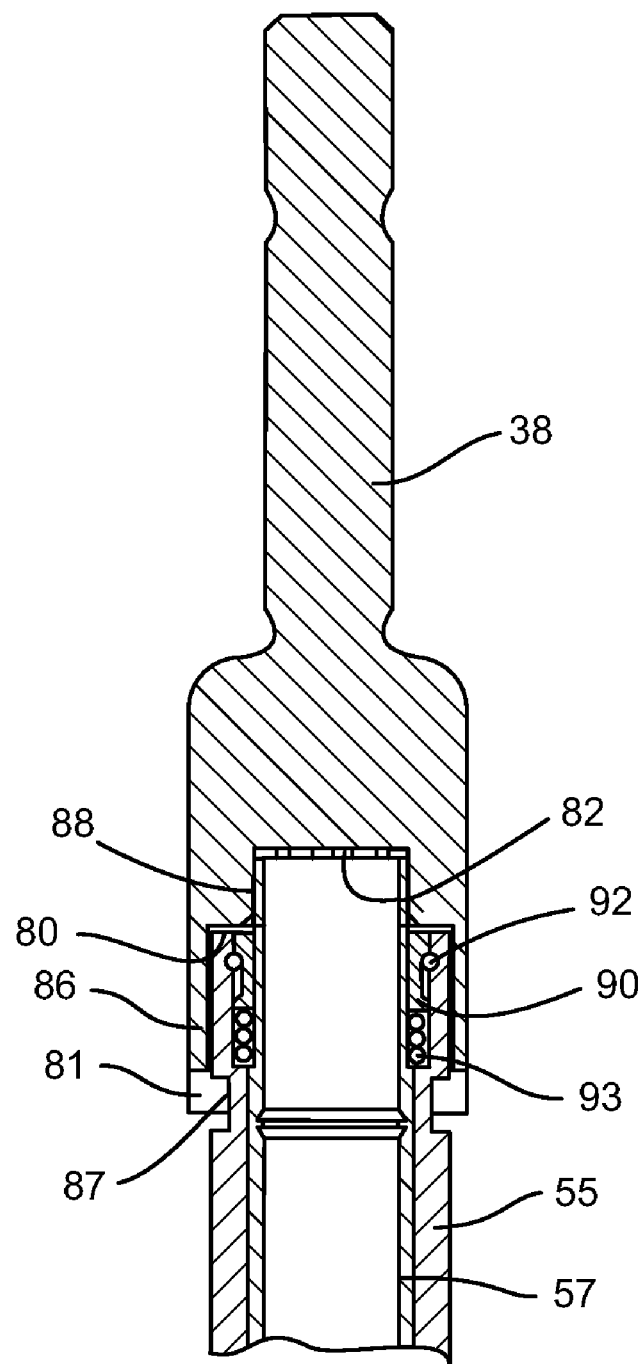
FIG. 14 is a cross-sectional view of the socket driver mounted to the distal end of the screw extension assembly in a first position.

However, the outer sleeve 55 further defines a radially inward groove 87 defined below or distal to the rectangular surface 86. This groove 87 is arranged to be aligned with the rectangular rim 81 when the socket driver 38 is fully seated on the proximal end 55*a* of the outer sleeve 55, as depicted in FIG. 14. Thus, when the end of the outer sleeve is adjacent the end of the cylindrical socket 80 the rim 81 is aligned with the groove 87. In this position, there is no surface of the outer sleeve that bears against the rectangular surface of the rim 81 so the socket driver 38 is free to rotate relative to the outer sleeve 55.

The driver socket 82 is configured to engage the proximal end 57*a* of the inner sleeve 57. In particular, the proximal end 57*a* includes a mating end 88 that is complementary to the driver socket 82. In one embodiment, the driver socket and mating end have a hex configuration so that the socket driver 38 can be used to rotate the inner sleeve 57 when the mating end 88 is disposed within the driver socket 82, as shown in FIG. 14. In a particular configuration the driver socket 82 may define a 12-point contact socket so that in combination with the rectangular outer surface 86 at the proximal end 55*a* of the outer sleeve 55, the socket driver 38 may be engaged every ninety degrees.

Figure 12:
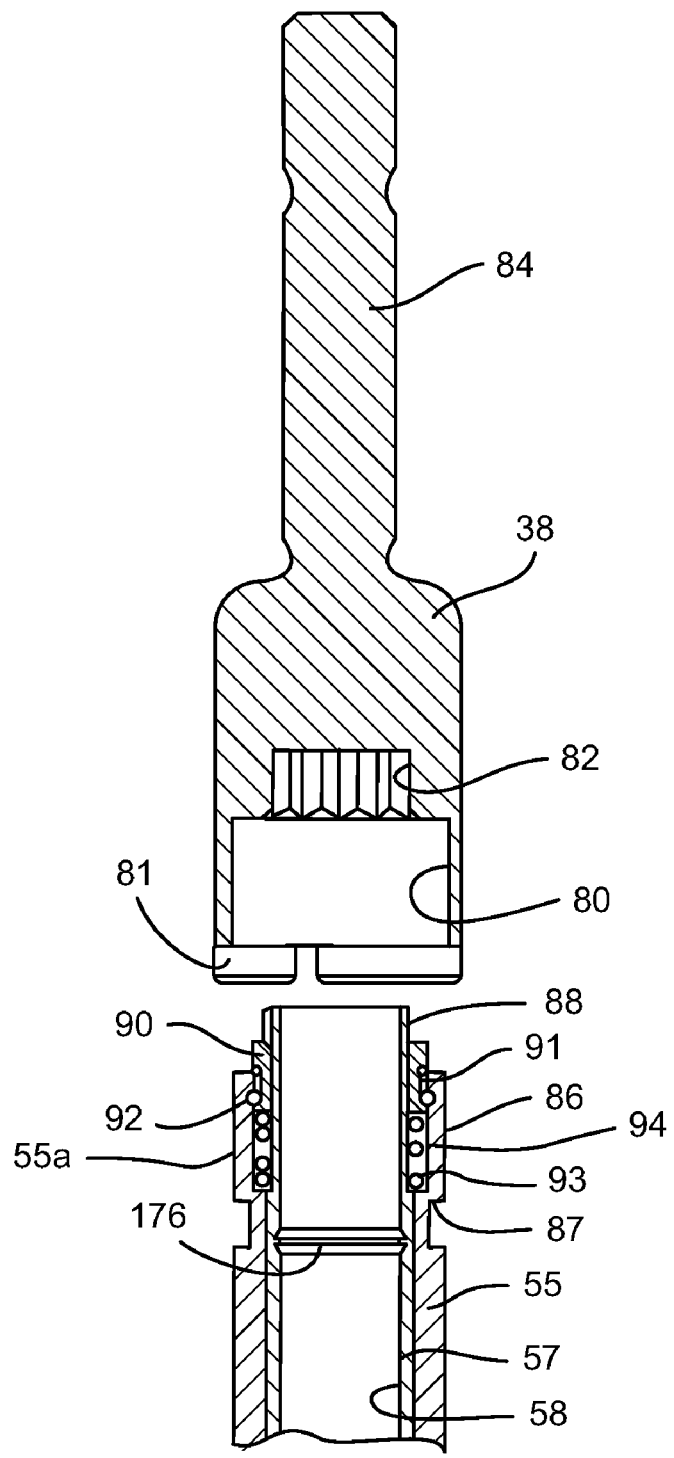
FIG. 12 is an enlarged exploded view of the proximal end of the screw extension assembly and the socket driver shown in FIG. 4
Figure 13:
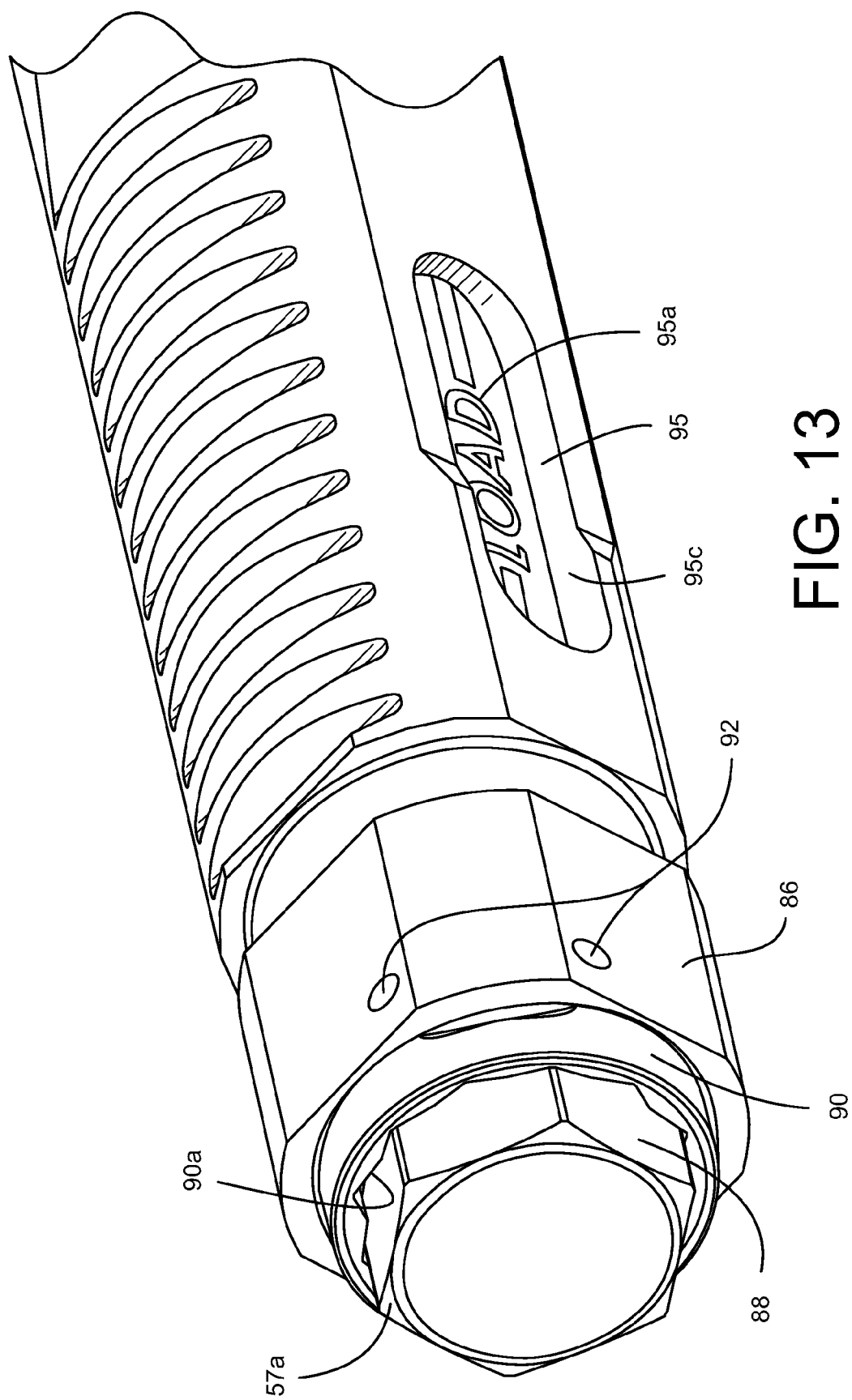
FIG. 13 is an enlarged perspective view of the distal end of the screw extension assembly shown in FIG. 4 with the assembly in a first loading position.

The screw extension assembly 32 may incorporate features to prevent relative rotation between the inner and outer sleeves. For instance, when the screw extension assembly is engaged to a bone screw assembly it is desirable to ensure that the two assemblies are locked and cannot be inadvertently disengaged. Since engagement or disengagement occurs with relative rotation between the inner and outer sleeves, preventing inadvertent rotation of the inner sleeve can prevent inadvertent disengagement from the screw assembly 15. Accordingly, the screw extension assembly includes a displaceable retention ring 90 that initially engages the mating end 88 of the inner sleeve 57. The retention ring 90 may include a hex interface 90a for engaging the hex features of the mating end. The retention ring 90 is held against rotation relative to the outer sleeve, while permitting axial movement of the ring within the outer sleeve. Thus, the retention ring may define one or more longitudinally extending capture slots 91 that receive a corresponding capture pin 92 that is embedded in the outer sleeve as shown in FIG. 12. The retention ring 90 is thus permitted to slide axially or longitudinally within a bore 94 at the proximal end 55a of the outer sleeve 55 from the extended position shown in FIG. 12 to a depressed position shown in FIG. 14. A biasing spring 93 is disposed within the bore 94 to bias the retention ring 90 to the extended position in which the retention ring engages the hex end 88 of the inner sleeve 57, as described above.

Figure 15:
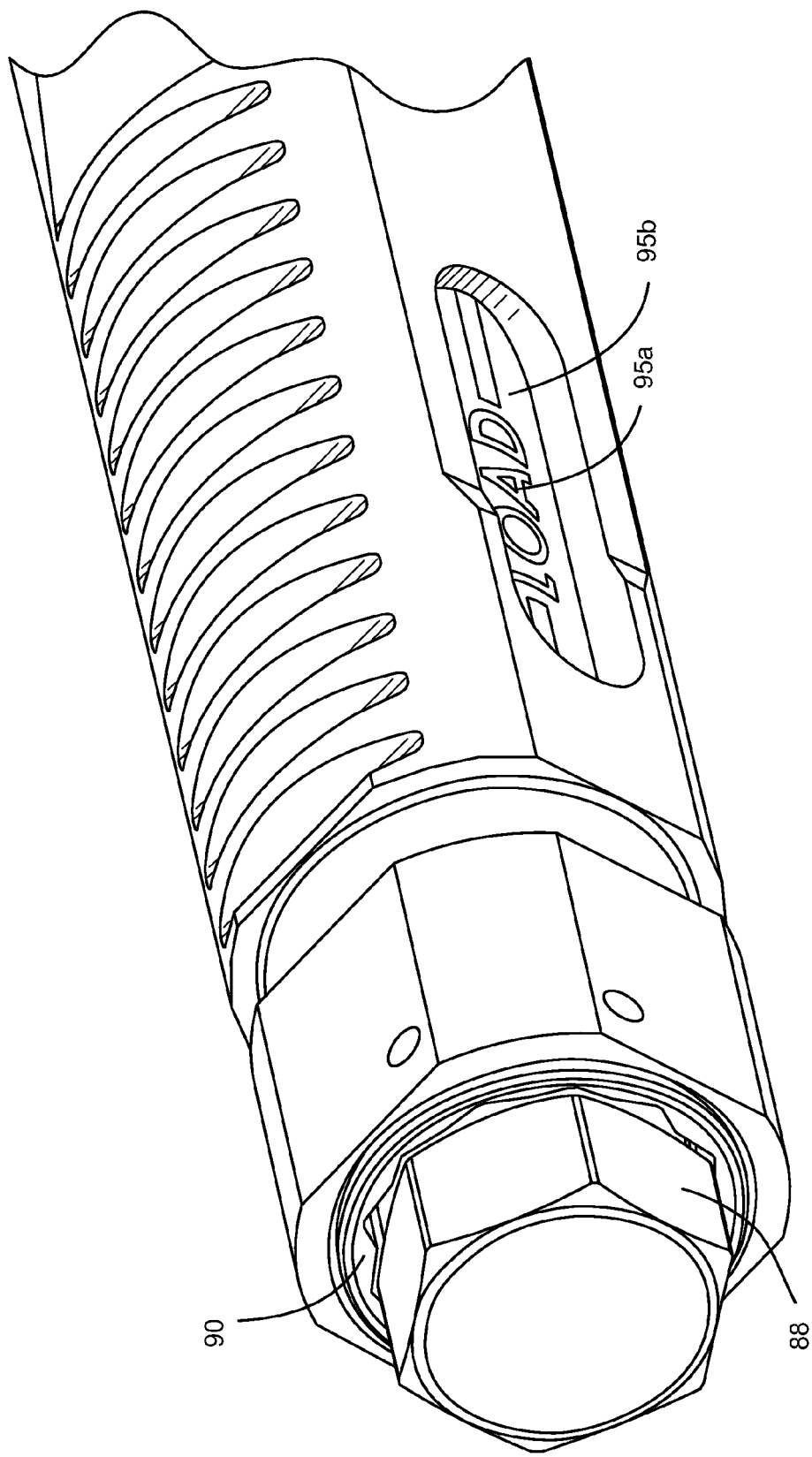
FIG. 15 is an enlarged perspective view of the distal end of the screw extension assembly shown in FIG. 4 with the assembly in a second loading position.

As shown in FIGS. 14-15, the retention ring 90 can be moved to its depressed position by pressing the socket drive 38 downward or toward the proximal end 55a of the outer sleeve. The base of the cylindrical socket 80 contacts the retention ring 90 pushing it down with the socket driver until the cylindrical socket bottoms on the top of the outer sleeve. In this position the retention ring 90 is clear of the hex end 88 so that the hex end is free to be rotated by the hex socket 82. (As explained above, in this position shown in FIG. 14 the rectangular rim 81 is also clear of the rectangular outer surface 86 of the outer sleeve).

Figure 16:
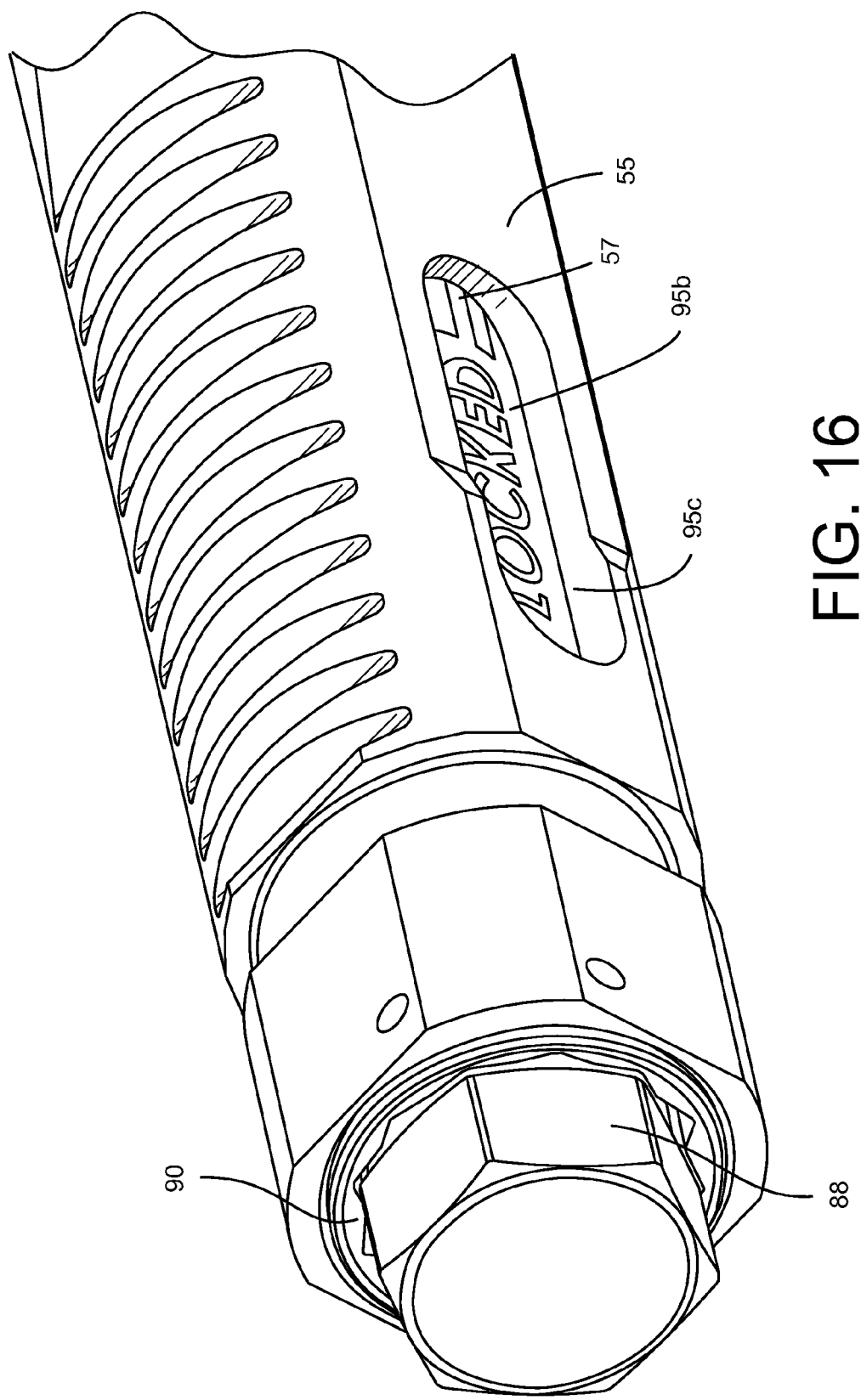
FIG. 16 is an enlarged perspective view of the distal end of the screw extension assembly shown in FIG. 4 with the assembly in a locked position.

The screw extension assembly 32 further includes an indicator 95 that indicates to the surgeon the relative position of the inner and outer sleeves. Thus, when the screw extension assembly 32 is in its initial orientation (i.e., with the inner sleeve in the position shown in FIG. 5 to accept a bone screw yoke) the indicator includes the indicia 95a "LOAD" viewable in the window 95c formed in the outer sleeve. The indicia 95a is affixed or applied in a suitable manner to the outer surface of the inner sleeve. When the screw extension assembly 32 has been coupled to the yoke 17 of the bone screw assembly (as shown in FIGS. 10-11) the indicia 95b "LOCKED" is visible through the window 95c, as illustrated in FIG. 16. As shown in FIG. 4, this indicator 95 is at the proximal end 55a of the outer sleeve so that it is readily visible to the surgeon outside the surgical site.

Figure 17:
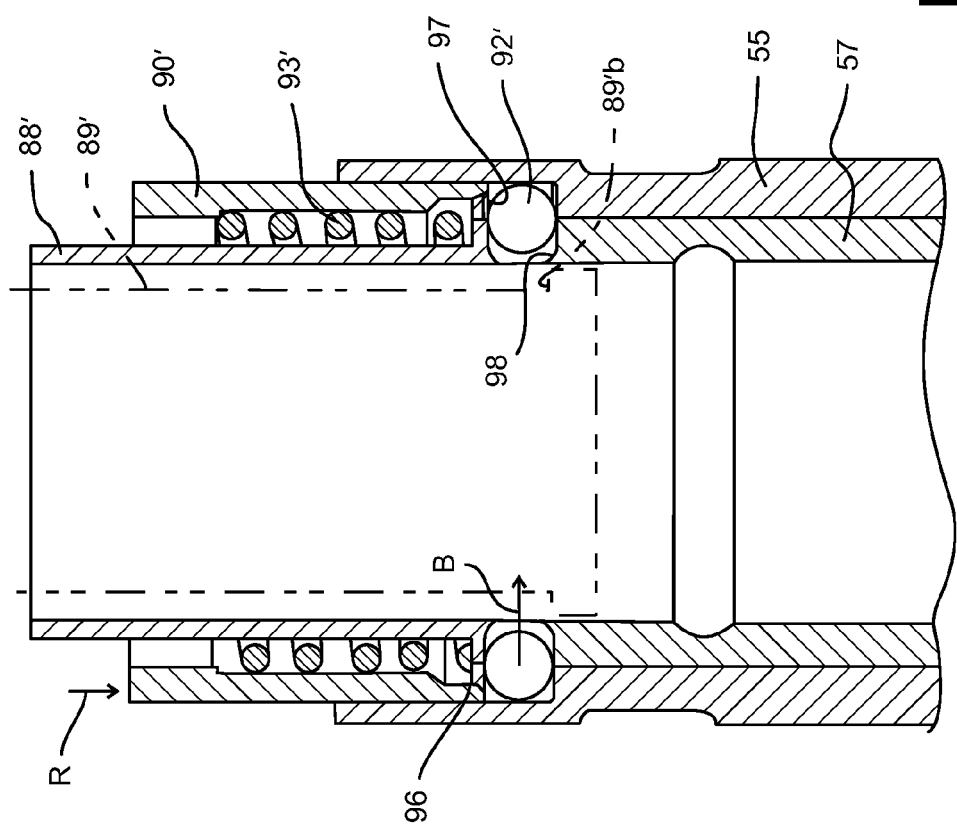
FIG. 17 is an enlarged cross-sectional view of one embodiment of the distal end of the screw extension assembly shown in FIG. 4.

In an alternative embodiment a modified retention ring 90' is operable to free the inner sleeve for rotation relative to the outer sleeve, as illustrated in FIG. 17. In this embodiment, a number of retention balls 92' are situated between a locking bore 97 defined in the outer sleeve 55 and a corresponding number of ball recesses 98 defined in the inner sleeve 57. The retention ring 90' is initially positioned as shown in FIG. 17. When the ring is pushed in the direction of the arrow R a lower cam surface 96 contacts and bears against the retention balls 92'. This contact gradually pushes the retention balls 92' radially inward in the direction of the arrow B to a release position in which the balls are seated within the corresponding recesses 98. In this position the inner sleeve 57 is free to rotate relative to the outer sleeve 55. A biasing spring 93' may be provided to bias the retention ring 90' away from the release position and to the locked position in which relative rotation is prevented.

In one embodiment, the socket driver 38 may be provided with a stepped shaft 89' extending from the socket hex 82 (FIG. 14) and projecting through the inner sleeve 57 as shown in FIG. 17. The stepped shaft 89 includes a stepped distal end 89'b that is sized to be retained by the capture balls 92' when the socket driver 38 is fully seated on the inner sleeve and has fully depressed the retention ring 90'. The capture balls 92' thus prevent removal of the socket driver as long as they are in the inboard position denoted by the arrow B.

Screw Driver Instrument

Figure 18:
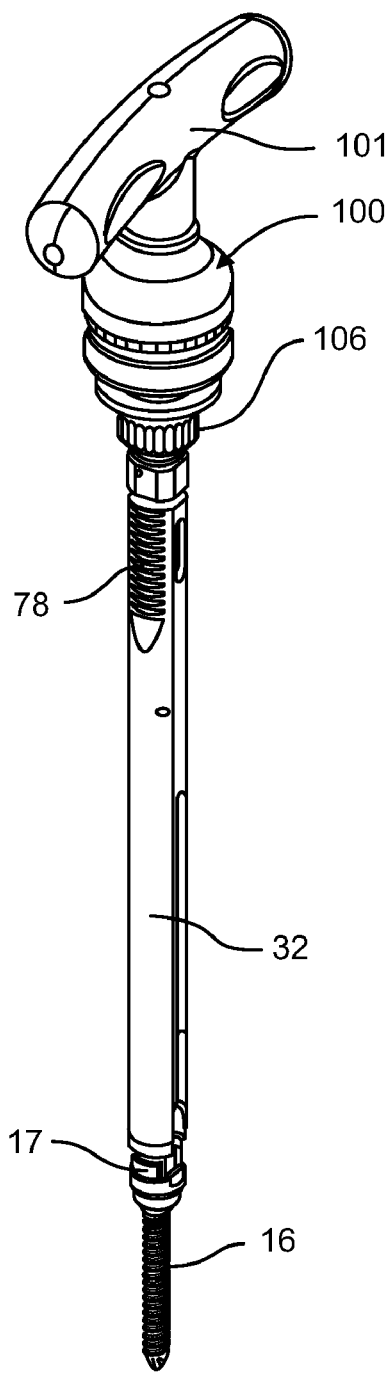
FIG. 18 is a perspective view of the bone screw and screw extension assembly with a screw driver mounted thereon.
Figure 19:
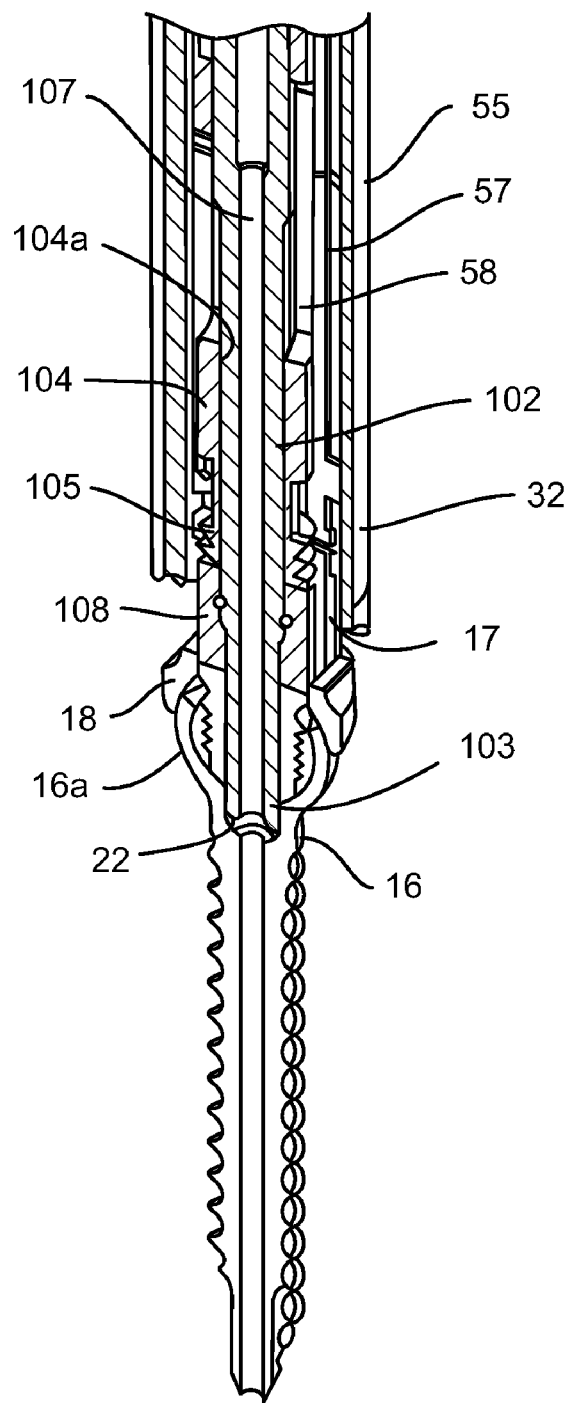
FIG. 19 is a cross-sectional view of the bone screw, screw extension assembly and screw driver shown in FIG. 18.

The screw extension assembly 32 is configured to accept additional tools for access to the bone screw assembly. For instance, the bore 58 of the inner sleeve 57 is sized to receive a screw driver 100 as shown in FIGS. 18-19. The screw driver 100 includes at the proximal end a handle 101 connected to a shaft 102 to permit manual rotation of the shaft. The shaft 102 includes at the distal end a tip defining an engagement end 103 that is configured to engage a drive tool recess 22 in the base of the bone screw head 16a. The engagement end and drive tool recess can be configured in a conventional manner, such as with a hex or Torx feature. The shaft 102 is sized so that the engagement end 103 can be received within the recess 22 while the handle 101 is accessible at the proximal end of the screw extension assembly 32.

The screw driver tool 100 includes an outer retention sleeve 104 having an interior bore 104a through which the shaft 102 extends. The shaft 102 and retention sleeve 104 are coupled to each other to allow free relative axial and rotational movement therebetween. The distal end 103a of the retention sleeve 104 is provided with exterior threads to match the internal threads 48 on the interior surfaces 44 of yoke 17. The retention sleeve 104 is connected to a knob 106 (FIG. 18) situated on or adjacent the proximal end of the screw extension assembly 32 that is configured to facilitate manual rotation of the retention sleeve to thread the distal end 103a into the yoke. A stop 108 is rotatably mounted on the shaft 102 and is configured to seat within the slot 42 of the yoke 17 to support the shaft and retain the sleeve. Upon threaded connection of the outer retention sleeve 104 to the yoke 17, the retention sleeve 104 bears against the stop 108 and the stop bears against the yoke to provide joint rotational movement of the retention sleeve, stop and yoke. Prior to such threaded connection, the engagement end 103 of the inner shaft is guided into the drive tool recess 22 in the base of the bone screw head 16a. The stop 108 may be sized to prevent threading of the retention sleeve into the yoke unless and until the end 103 of the shaft is engaged within the tool recess of the bone screw. Once the tool 100 is properly seated, rotation of the handle 101 that is connected to the shaft 102 will rotate the bone screw shank 16. With the screw extension assembly 32 and the retention sleeve 104 attached to the yoke for joint movement, and with the yoke 17 being able to freely articulate with respect to screw shank 16, the screw extension assembly 32 may be manually held while the handle 101 is rotated to drive the screw shank 16 into a pedicle of a vertebra.

The screw extension assembly thus provides an avenue for guiding the screw driver instrument 100 into engagement with the bone screw. Even if the screw extension assembly is articulated relative to the bone screw, a minor manipulation of the assembly will automatically align the screw driver instrument with the drive tool recess. Once engaged the screw driver can be used to thread the bone screw 16 into the vertebra in a known manner and then removed from the screw extension assembly. The shaft 102 of the screw driver 100 may be provided with a guide wire lumen 107 to allow introduction of the tool over a previously positioned guide wire.

Rod Introducer Assembly

With the bone screw assemblies anchored in the vertebrae with the screw extension assemblies engaged to the screw assemblies, the connecting rod 25 can be introduced through the rod slots 59, 67 in the extension assemblies using a rod introducer assembly 34, as shown in FIG. 3. Details of the rod introducer assembly and its operation are shown in FIGS. 20-28. The introducer assembly 34 includes a handle 110 configured to be manually grasped to manipulate the connecting rod 25 attached to the introducer assembly. The handle is also configured for easy access to the actuation mechanism 112 used to enable grabbing and locking a connecting rod to the assembly, as well as to push buttons 145 and 152 used to release the actuation mechanism in various stages of operation, as explained herein. The handle 110 and lever 113 of the actuation mechanism 112 may be particularly configured to permit one-handed operation of the lever during its stages of actuation.

Figure 26:
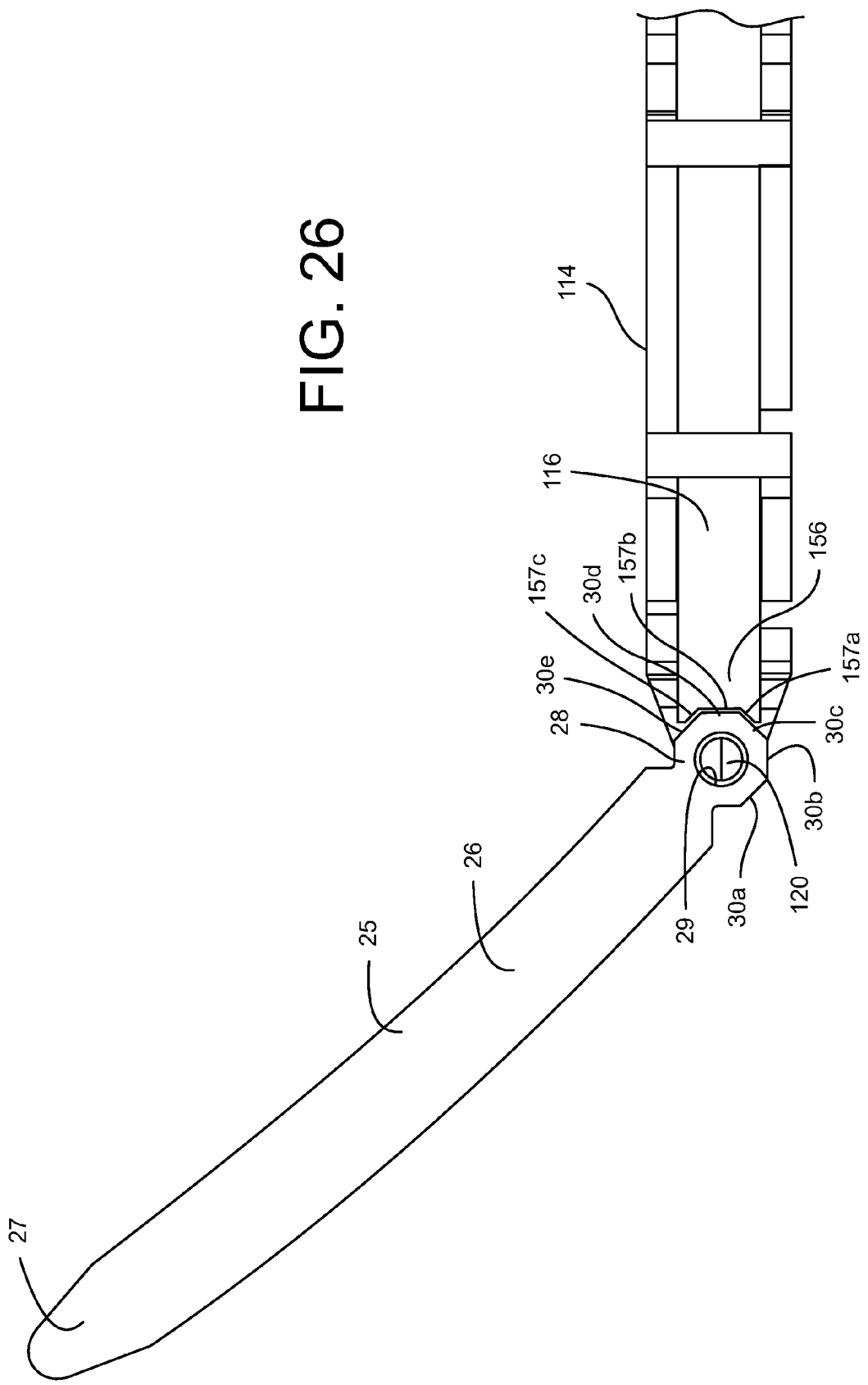
FIG. 26 is an enlarged cross-sectional view of the rod engaged to the assembly as shown in FIG. 25.

Looking first at FIG. 26, the connecting rod 25 includes an introduction end 27 that may be tapered to facilitate introduction of the rod through tissue, an incision, and/or the rod slots 59 and 67 in the screw extension assemblies. The elongated body 26 of the rod is sized to span the distance between the instrumented vertebrae and may have a curvature calibrated to accommodate or correct the orientation of the instrumented vertebral levels in a known manner, such as for lordosis and kyphosis. The connecting rod further includes an engagement end 28 that defines an opening 29 and a series of flats 30a-30e. These features of the engagement end 28 provide the interface with the rod insertion assembly 34.

Figure 20:
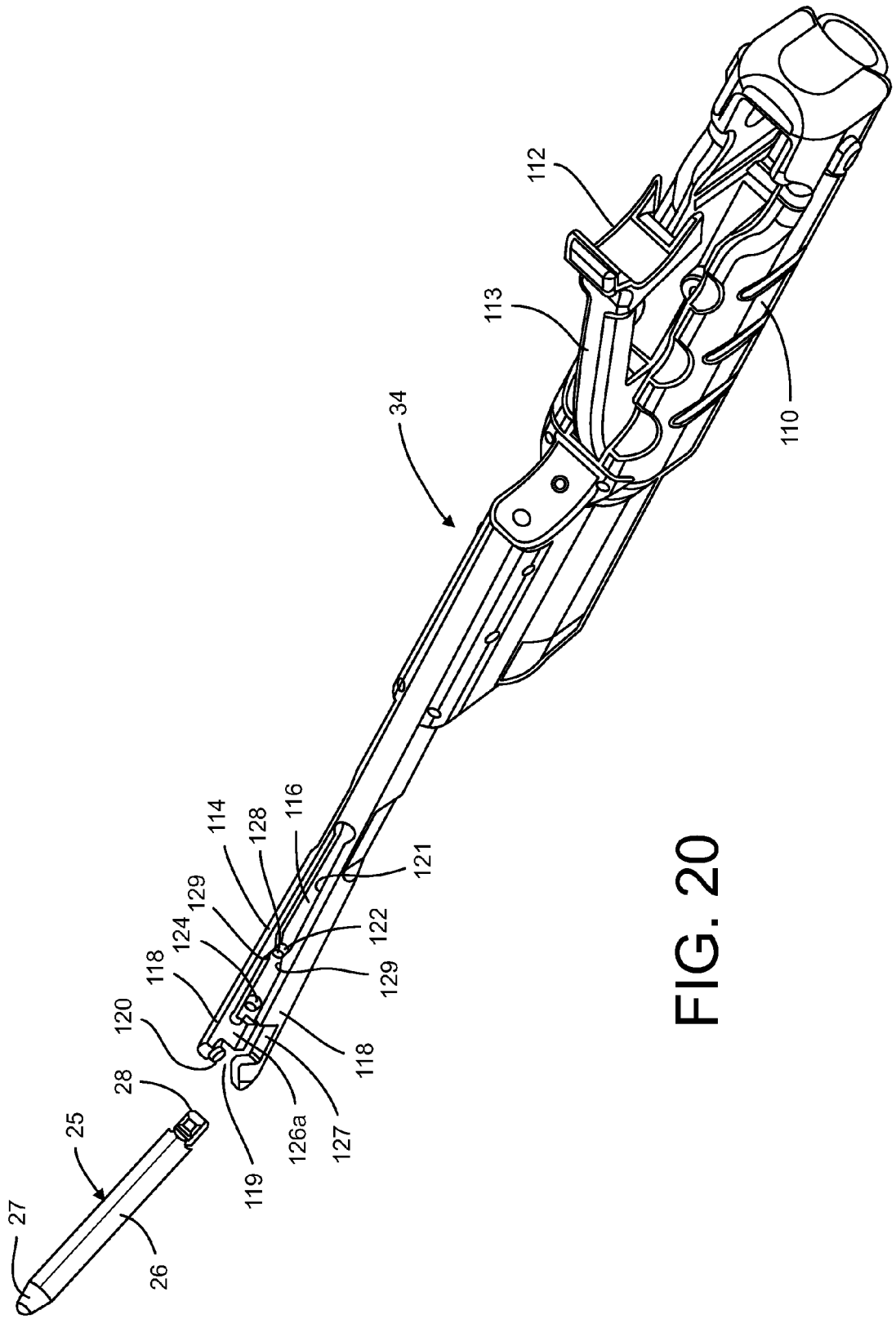
FIG. 20 is a perspective view of the rod introducer assembly and connecting rod shown in FIG. 3.
Figure 21:
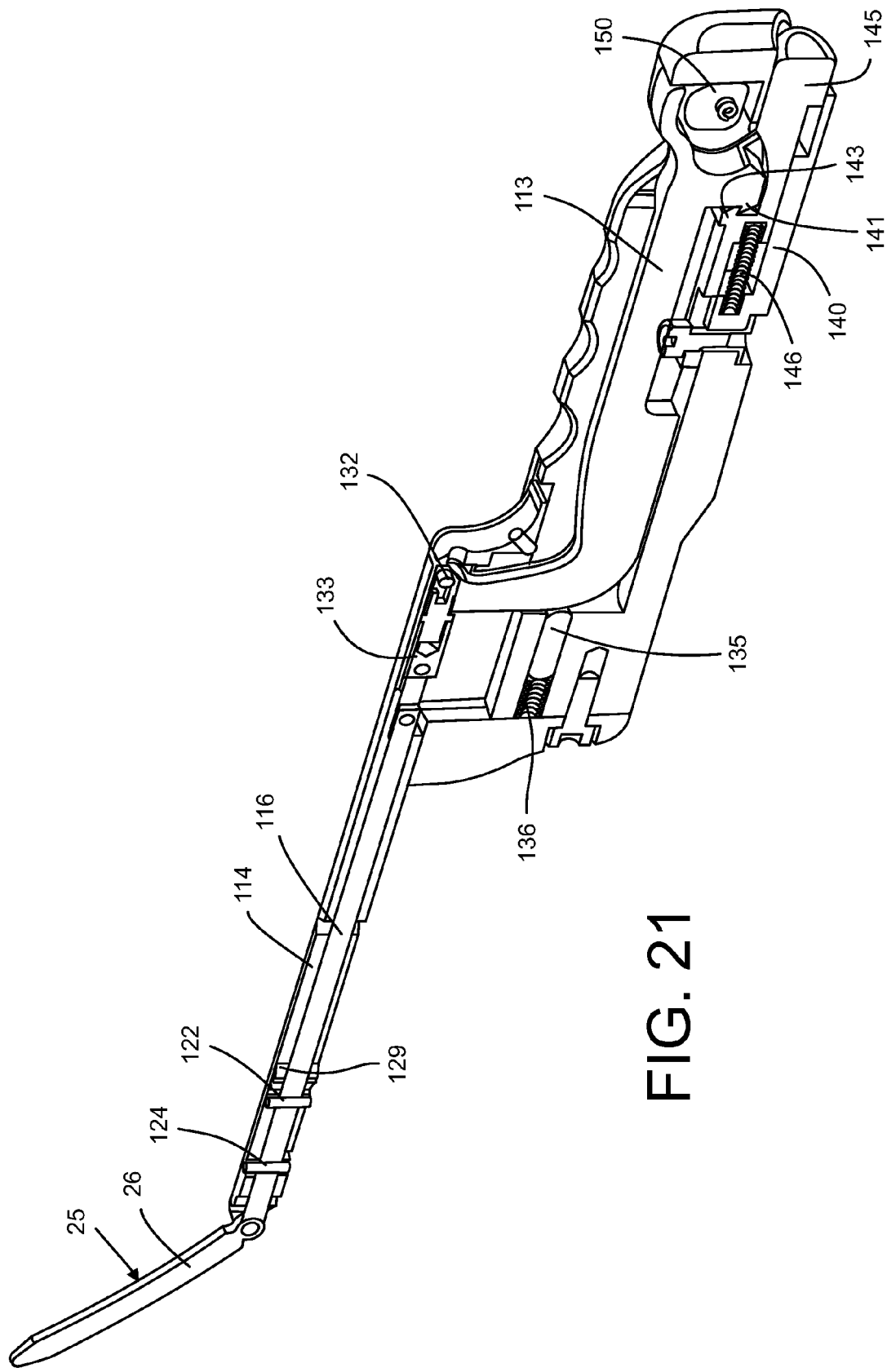
FIG. 21 is a cut-away view of the rod introducer assembly shown in FIG. 20 with the connecting rod engaged thereto and the assembly in a locked position.

Turning to FIGS. 20-21, the rod insertion assembly 34 includes an outer sleeve 114 extending from the handle 110. As shown in FIG. 3 the outer sleeve has a length approximating the height of the extension assemblies 32 above the bone screws mounted in the vertebrae. The outer sleeve has a length sufficient for the surgeon to manipulate the handle 110 outside the patient while the connecting rod 25 carried by the instrument is fully seated within the yokes of the bone screw assemblies. The outer sleeve 114 is at least generally tubular along a portion of its length and it thus hollow to slidably receive an inner actuator shaft 116 for translational movement within. The distal portion of the outer sleeve, which in the illustrated embodiment may constitute about half the length of the sleeve, branches into opposed flexible legs 118 separated by an expandable slot 121 through the top and bottom of the sleeve 114. The legs are capable of flexing outwardly relative to each other to form an expandable opening 119 into which the engagement end 28 of the connecting rod 25 is introduced (see also FIGS. 24-25). The legs 118 may be configured to be initially biased together or toward each other, the biasing force being provided by the natural resilience of the legs.

Figure 24:
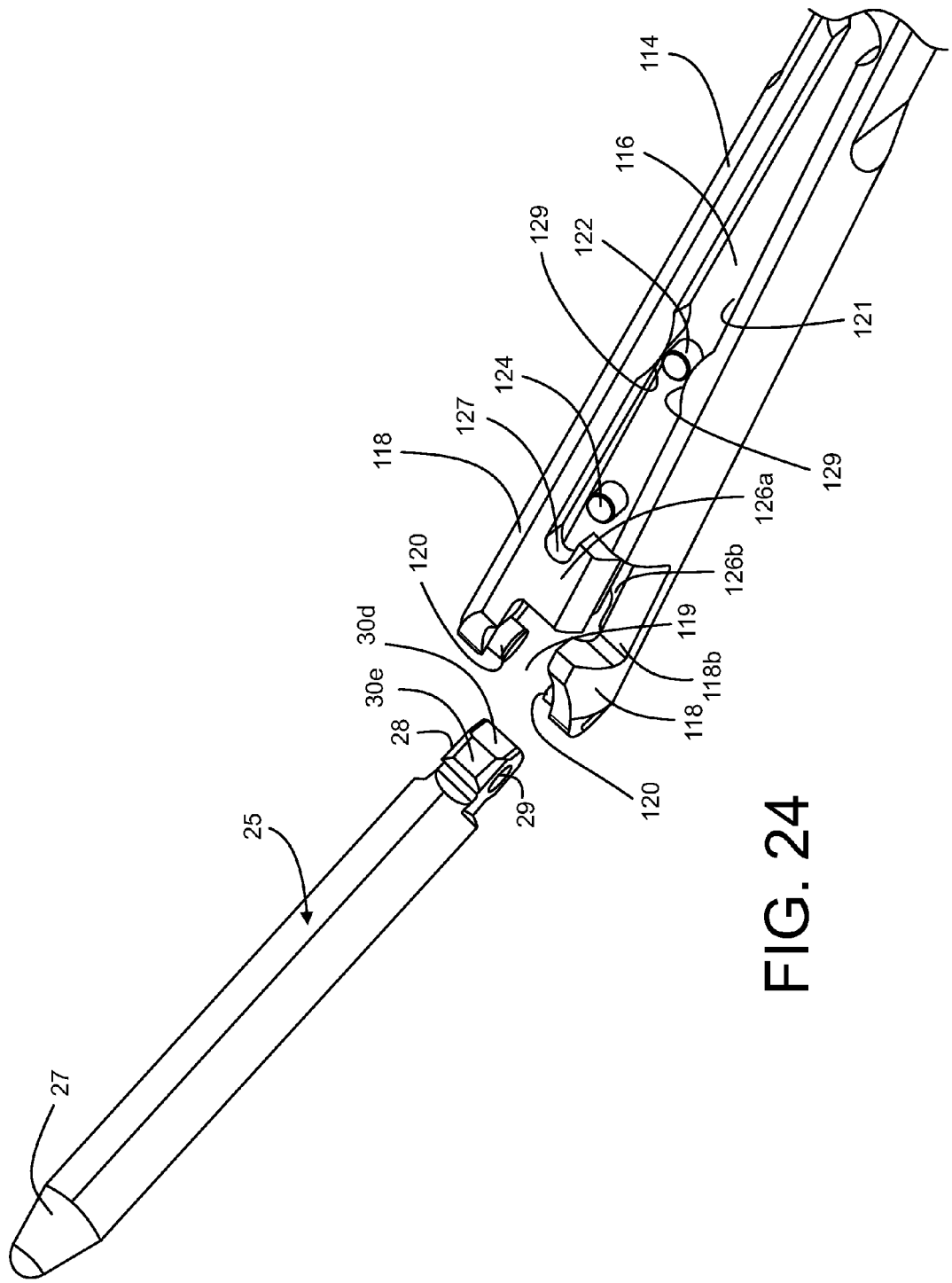
FIG. 24 is an enlarged perspective view of the distal end of the rod introducer assembly shown in FIG. 20 with the rod disengaged from the assembly.
Figure 25:
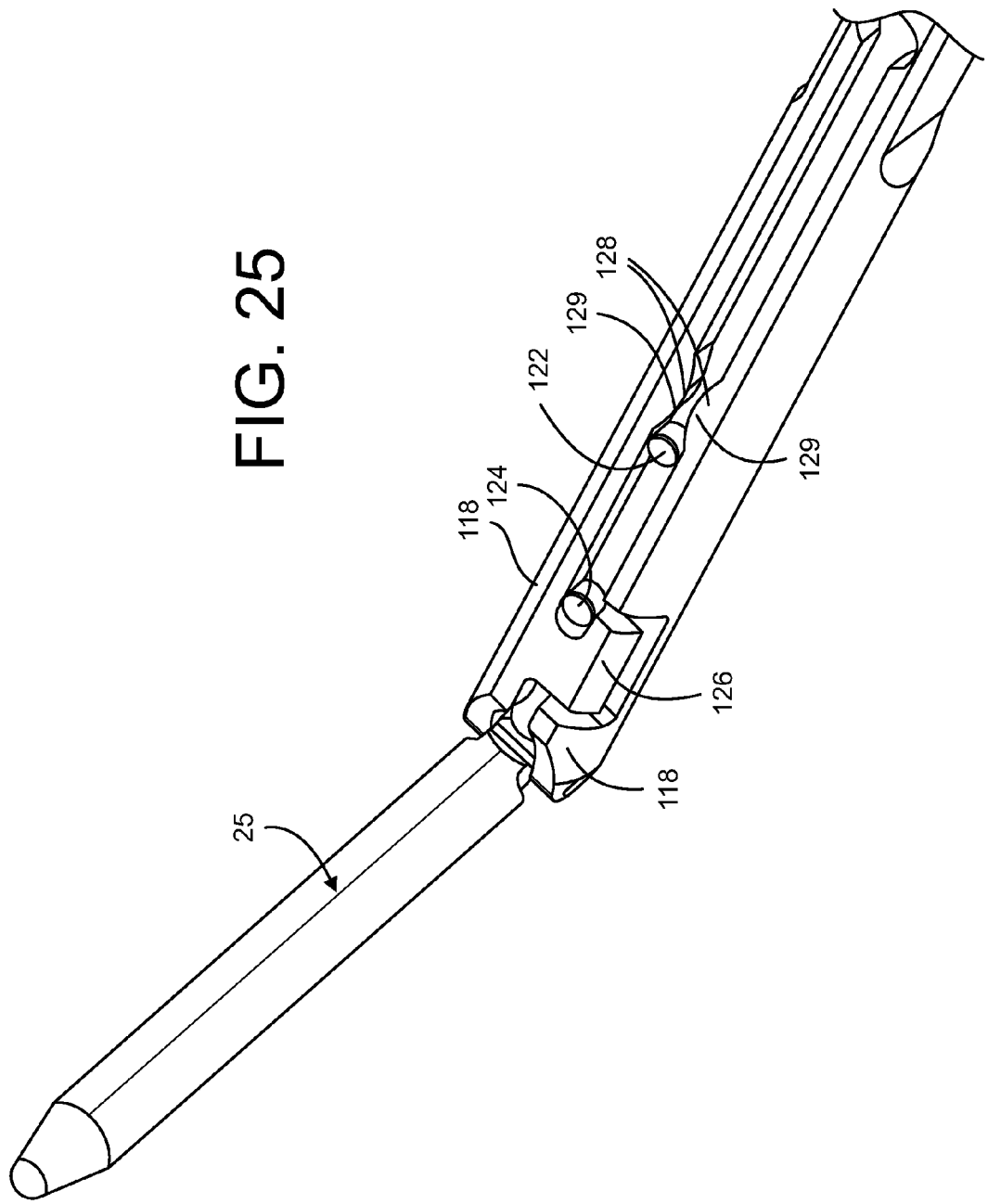
FIG. 25 is an enlarged perspective view of the distal end of the rod introducer assembly shown in FIG. 20 with the rod engaged to the assembly.

The expandable slot 121 of the legs defines opposing cam elements 128. The cam elements 128 are configured to provide a reduced slot width with a cam surface 129 (FIG. 25) leading to that reduced width. The inner actuator shaft 116 includes an actuator pin 122 that projects diametrically across the outer sleeve 114 (FIG. 21) and is arranged to contact the cam elements 128 as shown in FIGS. 24 and 25. In the configuration shown in FIG. 24 the actuator pin 122 is disposed directly between both cam elements 122, widening the gap between the elements, which in turn forcibly deflects the flexible legs 118 apart, and which ultimately increases the size of the expandable opening 119. On the other hand, when the actuator pin 122 is in the position shown in FIG. 25, the pin 122 is beyond or distal of the cam elements 128 so that the flexible legs are biased toward each other, thereby decreasing the size of the expandable opening 119. In this position, a locking pin 124 projecting from the inner actuator shaft 116 engages a recess 127 formed by locking hooks 126a, 126b adjacent the distal end 126 of the outer sleeve 114. It is noted that each leg includes a locking hook. Thus, when the locking pin 124 is disposed within the recess 127 defined by each locking hook 126a, 126b, the pin prevents separation of the locking hooks, and consequently separation of the flexible legs 118. Each leg defines a notch, such as notch 118b to receive the locking hook of the opposing leg, such as hook 126a, as shown in FIG. 25.

The flexible legs 118 of the outer sleeve 114 include inwardly directed posts 120 that are sized to be received within the opening 29 in the engagement end 28 of the connecting rod 25, as shown in FIG. 24. The posts 120 are disposed generally perpendicular to the longitudinal axis of the outer sleeve 114 and are particularly sized so that they provide adequate space between them when the expandable opening 119 is at its largest extent so that the engagement end 28 of the rod can fit between the posts. The posts are also sized so that they do not contact each other when disposed within the opening 119, as shown in FIG. 25. (Alternatively the posts may be half cylinders that overlap each other within the opening 119). The posts 120 thus provide structure for engaging the connecting rod 25 and holding it to the rod introducer assembly 34 when the flexible legs 118 are in their closed position. The locking pin 124 and locking hooks 126a, b hold the legs together so that the connecting rod cannot be removed from the rod introducer assembly 34, at least not without disengaging the locking pin and hooks.

The locking pin 124 and the actuator pin 122 are advanced or retracted by axial movement of the inner actuation shaft 116 within the outer sleeve 114. This movement is accomplished by the actuation mechanism 112. The lever 113 of the actuation mechanism is coupled to the inner shaft 116 by a linkage 133. The lever itself is pivotably mounted to the handle 110 at pivot pin 132 so that the lever can pivot from the first position shown in FIG. 21, to a second position shown in FIG. 22 to a third position shown in FIG. 23. The pivoting movement of the lever about pivot pin 132 is translated to linear movement of the inner shaft 116 through the linkage 133. In the first position shown in FIG. 21, the lever is locked within the handle 110 and the inner shaft has moved to its farthest distal extent. In this farthest distal position, the locking pin 124 is engaged in the locking recesses 127 and the legs 118 are locked together to grip the connecting rod, as shown in FIG. 25. In the third position shown in FIG. 23, the lever is fully unlocked from the handle and the inner shaft 116 has moved to its nearest proximal extent. In this proximal position, the actuator pin 122 has separated the legs 118 so that the connecting rod is automatically disengaged from the rod introducer assembly 34, as shown in FIG. 24. In the second position, also indicated as a neutral position, shown in FIG. 22, the posts 120 are disposed within the opening in the engagement end 28 of the connecting rod so the rod is still held by the rod introducer assembly, but in this position the rod can be pivoted about the posts to vary the angle of the connecting rod relative to the outer sleeve 114 as the rod is introduced into the surgical site, as explained more fully herein.

As shown in FIG. 26, the distal end of the inner actuator shaft 116 defines a rod engaging end 156. This end 156 defines a series of flat portions 157a, b, c that generally correspond to the flat surfaces 30a-30e of the engagement end 28 of the rod. The flat portions of the rod engaging end 156 define a partial polygonal socket which is configured to complementarily mate with the flat surfaces of the engagement end of the rod so that when the rod engaging end 156 is held directly against the engagement end 28 of the rod the rod cannot pivot about the posts 120. Flat surface 157b lies transverse, and preferably generally perpendicular, to and crosses the longitudinal axis of the inner shaft 116, with adjacent flat surfaces 157a and 157c lying angularly with respect to surface 157b and defining the socket therewith. In a preferred arrangement, the socket defined by the flat portions 157a, b, c of the rod engaging end 156 are the mirror image of the flat surfaces 30a-30e of the engagement end 28 of the rod. Thus, in the first position of the lever 113 shown in FIG. 21 the rod engaging end 156 is in flush contact with the engagement end 28 of the rod. However, in the second position of the lever shown in FIG. 22, the inner shaft 116 is backed off slightly from the engagement end 28 of the rod, as shown in FIG. 26. The gap between the flat surfaces of the engagement end, such as surfaces 30c, 30d and 30e, and the flat connecting surfaces 157a-c of the actuator shaft, allows the rod to be pivoted about the posts 120. The proximity of the rod engaging end 156 to the engagement end 28 of the rod provides resistance to this movement so that the rod can be moved to a particular angle and held there without any outside force. The resistance provided by the corners of the polygonal socket at the rod engaging end 156 acts as detent and is readily overcome by slight manual pressure which creates tactile feedback to the surgeon and an audible snapping sound.

The array of flat surfaces 30a-e at the engagement end 28 of the rod 25 allow the rod to be positioned and locked in five angular orientations relative to the rod introducer assembly 34. Thus, when the flat surface 30d is aligned with the rod engaging end 156 of the actuator shaft 116, the rod is oriented at a 45 degree angle relative to the outer sleeve 114 of the introducer assembly, as shown in FIG. 26. When flat surface 30e is aligned with flat engagement surface 157b, the rod is at an angle of 90 degrees. When the flat surface 30c is aligned the rod is generally collinear with the outer sleeve, or at an angle of 0 degrees. The rod 25 can also be pivoted downward from the position shown in FIG. 26 to the 45 and 90 degree angles. It is noted that when the rod is pivoted to one of the "upward" positions, such as shown in FIG. 26, the curvature of the rod is generally toward the rod introducer assembly and is used typically for lordotic applications. On the other hand, if the rod is reversed to one of the "downward" positions opposite that shown in FIG. 26, the curvature of the rod faces away from the introducer assembly and is used typically in kyphotic applications. This feature provides flexibility for the surgeon to apply different corrections using the same rod and introducer assembly.

It should be understood that the angular configurations of the flat portions 157a, b, c of the rod engaging end 156 and the corresponding flat surfaces 30a-30e of the engagement end 28 of the rod 25 may be varied to obtain other desired angles, which may, for example be in thirty degree or other increments. In addition, the rod engaging end 156 of the inner shaft 116 may be formed to have only a single flat surface, such as surface 157b to hold tightly against one of the flat surfaces 30a-30e of the engagement end 28 of the rod 25. It should also be appreciated that the socket defined at the rod engaging end 156 of the inner shaft 116 may be formed of a curved surface to mate frictionally with a like curved surface formed on the engagement end 28 of the rod 25. As such, in the second position as shown in FIG. 22 the gap would allow free non-detented pivotal movement of the rod 25 about the posts 120 until the shaft 116 is moved axially more distally to cause the rod engaging end 156 to tightly frictionally engage and hold the engagement end 28 of the rod 25 in a position as shown in FIG. 21.

Figure 22:
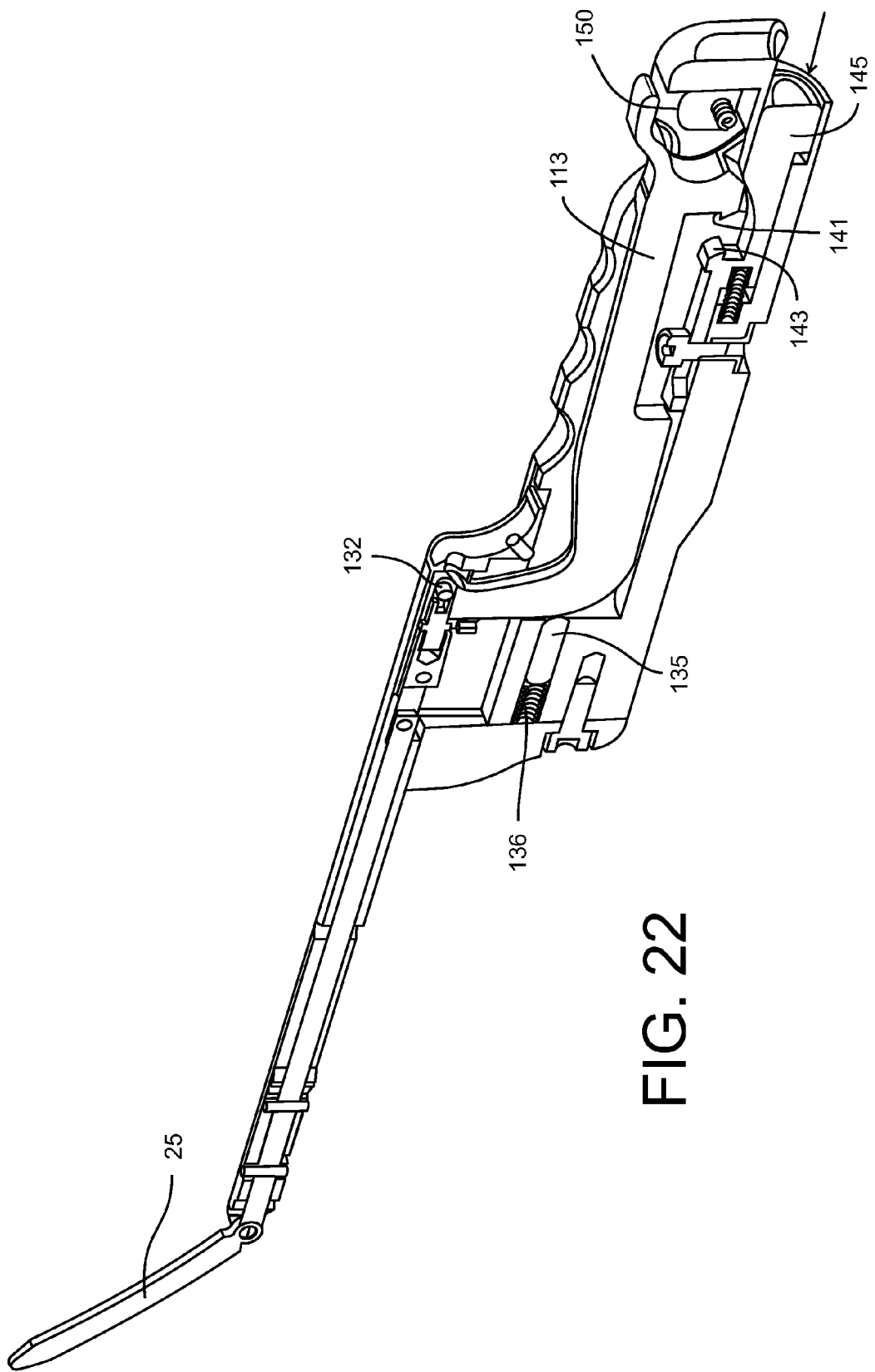
FIG. 22 is a cut-away view of the rod introducer assembly and rod shown in FIG. 21 with the assembly with a first locking mechanism released.

The rod introducer assembly 34 incorporates two locks used to hold the actuation mechanism 112, and particularly the lever 113, in the first position (FIG. 21) and in the second position (FIG. 22). As shown in FIG. 21, the first locking mechanism 140 includes a first locking surface 141 on the lever 113. A first locking element 143 is slidably mounted within the handle 110 and may be integrated onto a push button 145 that is biased outward by spring 146. The first locking surface 141 and the first locking element 143 may be in the form of engaging hooks, as illustrated in FIG. 21. The spring 146 biases the push button outward so that the two hooks remain engaged until the push button 145 is depressed against the spring.

When the push button 145 is depressed to release the first locking mechanism 140, the lever 113 pivots slightly upward to the second position shown in FIG. 22. The lever is pushed upward, or pivoted about the pivot pin 132 by the post 135. The post 135 is biased toward the lever 113 by a spring 136 and in a direction to cause the lever to pivot about the pivot pin. It can be appreciated that the lever can be returned to the first position shown in FIG. 21 by depressing the lever downward toward the handle, thereby pushing the lever back against the post 135 and spring 136.

Figure 23:
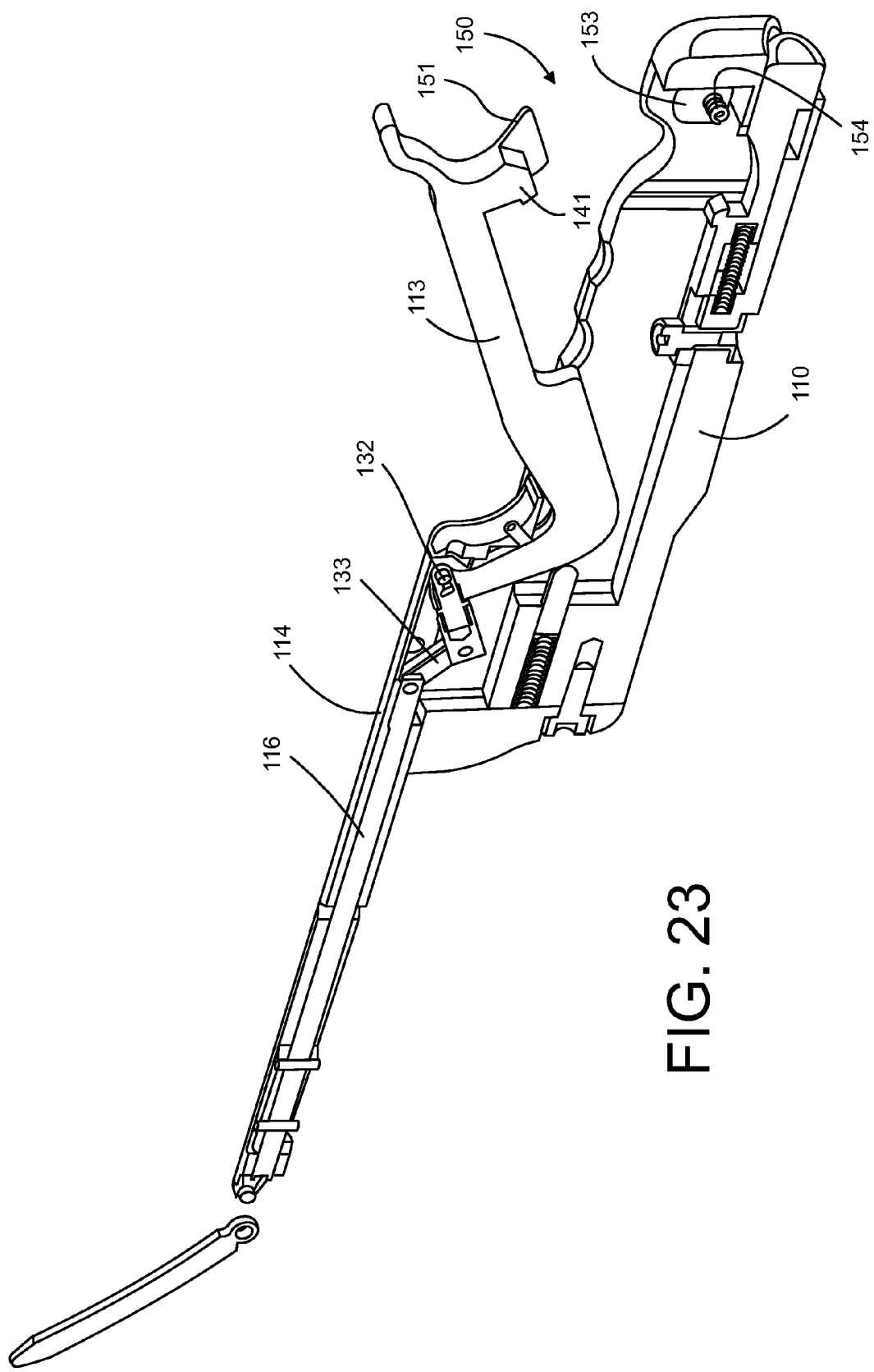
FIG. 23 is a cut-away view of the rod introducer assembly and rod shown in FIG. 21 with the assembly with a second locking mechanism released and the rod disengaged from the assembly.
Figure 27:
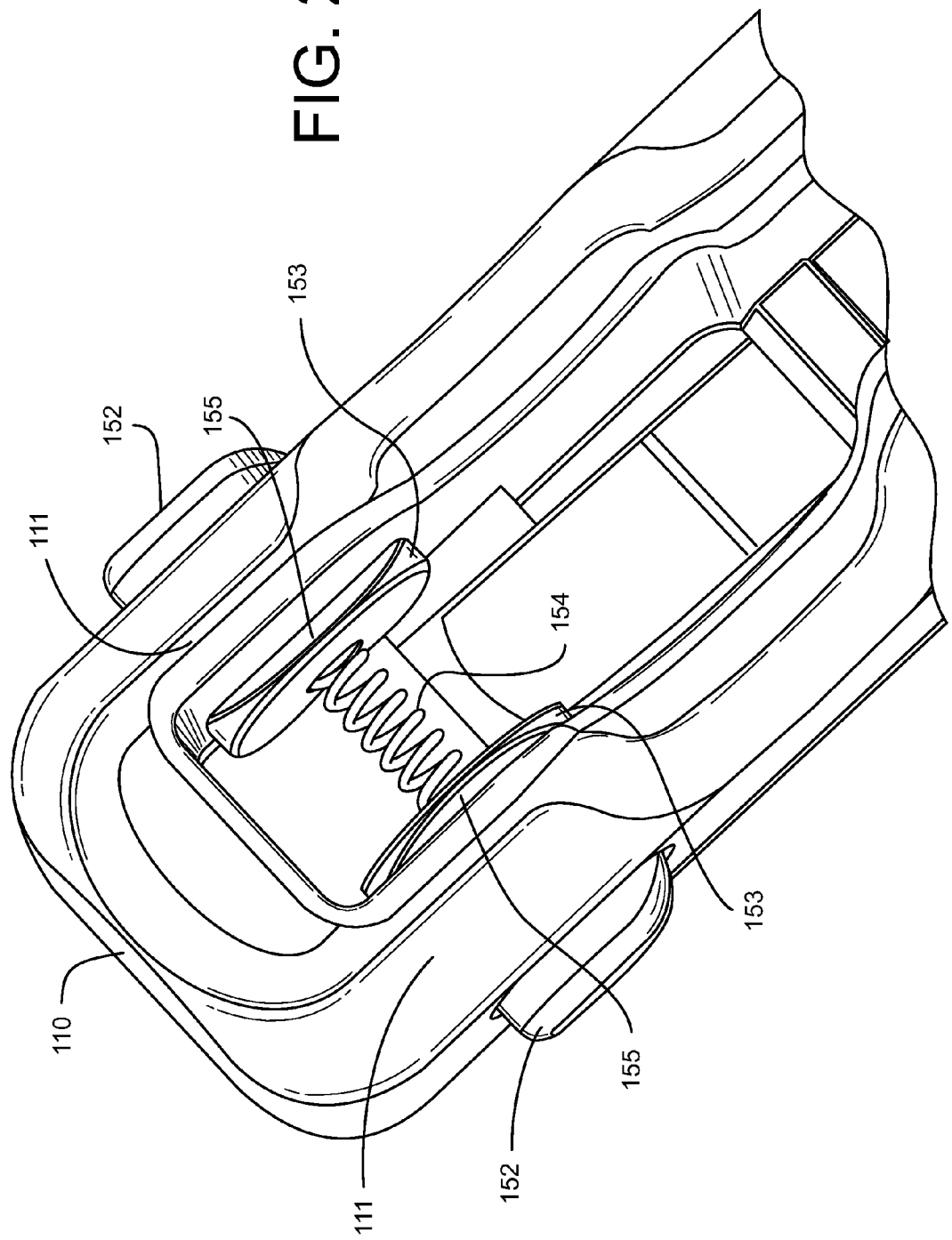
FIG. 27 is an enlarged view of the second locking mechanism of the rod introducer assembly shown in FIG. 20 with the mechanism in a locking position.
Figure 28:
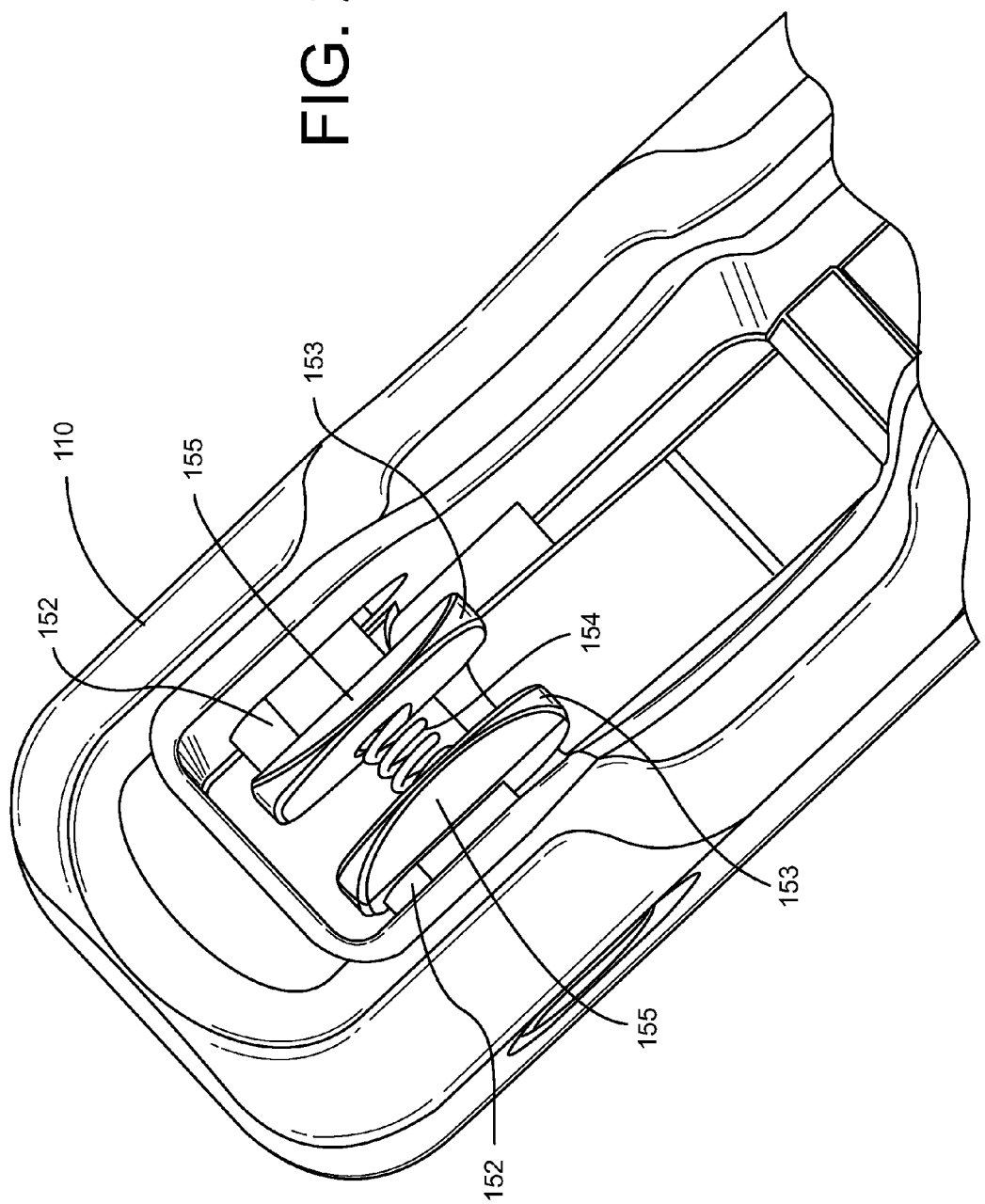
FIG. 28 is an enlarged view of the second locking mechanism of the rod introducer assembly shown in FIG. 20 with the mechanism in a release position.

The lever 113 is held in the second position shown in FIG. 22 by the second locking mechanism 150, which is shown in more detail in FIGS. 23, 27 and 28. The second locking mechanism 150 includes a second locking surface 151 integrated into the lever 113. It is noted that FIG. 23 only shows one such surface 151 since this figure is a cross-sectional view through the lever. Thus, an additional locking surface 151 is a mirror image to the surface depicted in FIG. 23. The second locking surfaces bear against the second locking element 153 mounted within the handle 110. As shown in the detail view of FIG. 27, the second locking element 153 includes two plates 155 forced apart by a spring 154 interposed therebetween. Each locking surface 151 of the lever 113 thus fit between a respective plate 155 and a side wall 111 of the handle 110, as generally depicted in FIG. 21. It can be appreciated that the plates 155 thus exert a friction force against the second locking surfaces 151 to prevent the lever 113 from pivoting upward.

The two plates 155 are carried by respective release buttons 152 that project laterally outward from the handle 110 when the second locking mechanism 150 is in its locked position illustrated in FIG. 27. The release buttons 152 may be depressed inward toward each other, as shown in FIG. 28, to push the plates 155 towards each other against the force of the spring 154. When the plates are in the position shown in FIG. 28, the contact between the plates and the second locking surfaces 151 of the lever 113 is reduced or eliminated so that the lever 113 is free to pivot upward to the third position shown in FIG. 23.

Rod Detector

Figure 29:
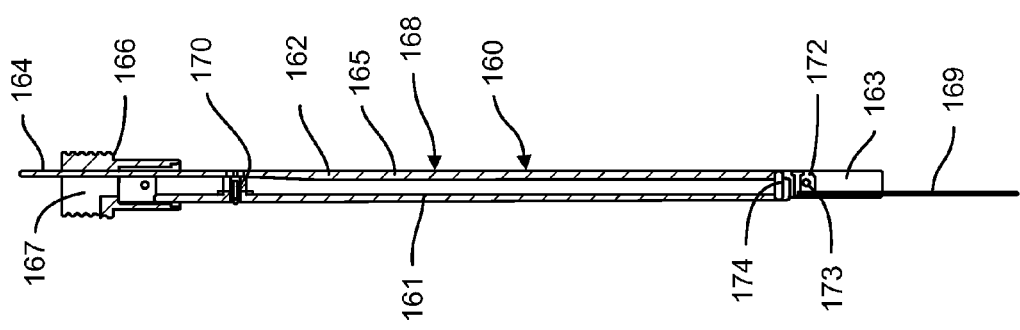
FIG. 29 is a cross-sectional view of a rod detector assembly for use with the instruments and procedures disclosed herein, shown with the detector flag in a first position.

The rod detector assembly 160 is used to detect the presence of an elongated connecting rod 25 into the bone screw assemblies 15 engaged to the vertebrae, as shown in FIG. 3. However, in certain procedures the point of entry of the rod 25 into the rod slots 59, 67 of the screw extension assemblies 32 (as described above) may not be visible to the surgeon. More particularly, since the rod may percutaneously enter the screw extension assemblies beneath the fascia S the surgeon may not be able to visually verify that the rod is properly positioned within the rod slots 59, 67, and ultimately within the slots 42 in the yokes 17 of the bone screw assemblies. A rod detector 160 is provided that can provide a readily seen and easily discernable visual indicator to the surgeon above the surgical site, as shown in FIG. 32. Details of the rod detector are shown in FIGS. 29-31.

Figure 30:
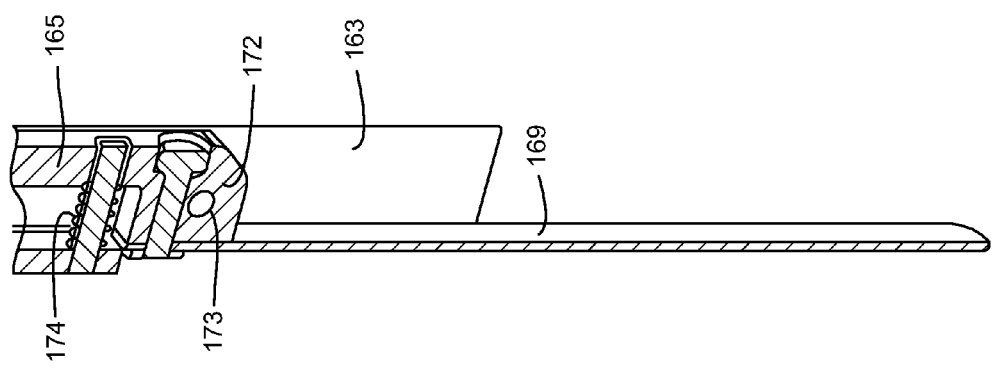
FIG. 30 is an enlarged cross-sectional view of the distal end of the rod detector assembly shown in FIG. 29.
Figure 31:
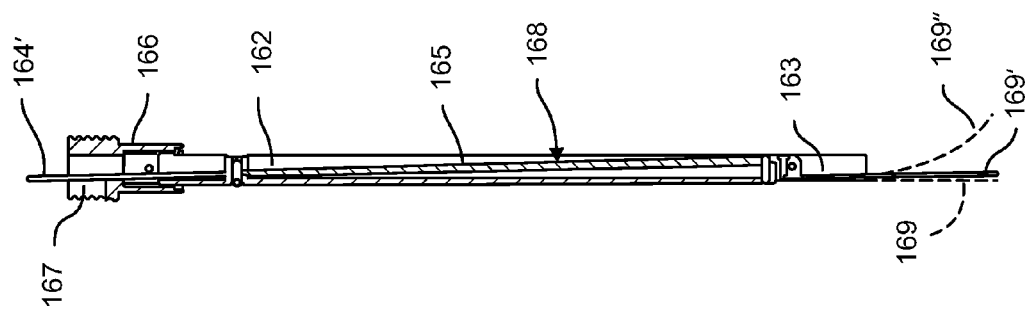
FIG. 31 is a cross-sectional view of the rod detector assembly shown in FIG. 29 with the detector flag in a second indicator position.
Figure 32:
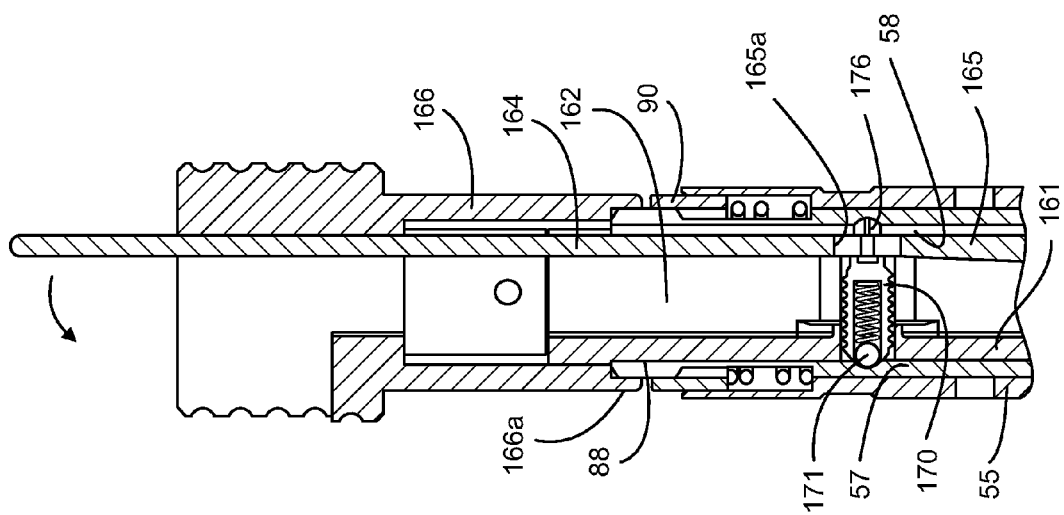
FIG. 32 is an enlarged cross-sectional view of the proximal end of the rod detector assembly shown in FIG. 29.

The rod detector 160 includes a generally tubular body 161 that is sized to fit within the bore 58 of the inner sleeve 57 of the screw extension assembly 32, as best seen in FIG. 31. In certain embodiments, the tubular body 161 is open at a slot 162 along a substantial portion of the length of the body, as seen in FIG. 30. At the distal end, the body forms two diametrically opposed branches 163 that are coincident with the slot 162 from one side of the body and that form a diametrically opposite slot. The detector includes a cap 166 affixed to the tubular body that is sized to seat on top of a screw extension assembly, as depicted in FIG. 32. The tubular body is sized to extend along a substantial portion of the length of the inner sleeve 57 but not so far as to interfere with the introduction of the rod 25 into the rod slot 67 of the sleeve.

The rod detector 160 includes a flag 164 that projects upward from the cap 166 as shown in the figures. The flag 164 may be connected to or integral with a strip 165 that spans the length of the tubular body to a base 172 at the top of the opposed branches 163, as seen in FIG. 29. The strip 165 is connected to a tip 169 that projects from the bottom of the tubular body 161. The tip 169 has a length or projects outward from the tubular body a sufficient distance to extend substantially into the slot 42 of the yoke 17 in a bone screw assembly mounted to the screw extension assembly 32 that the rod detector passes through. The tip 169 thus has a length sufficient so that it will be contacted by a rod 25 as it enters the slot 42 in the yoke.

The flag 154, strip 165 and tip 169 thus form a generally continuous indicator 168 that is pivotably connected to the tubular body 161 at a pivot mount 173 as shown in FIG. 30. The pivot mount thus permits the indicator 168 to rock back and forth about the mount 173 from the position shown in FIG. 29 in which the flag 164 is to the right of the cap 166, and the position shown in FIG. 31 in which the flag 164' is to the left of the cap. A slot 167 in the cap 166 accommodates this movement of the flag. A bias spring 174 bears against the strip 165 to push the strip and flag 164 to the position shown in FIG. 29. This position is the neutral position of the rod detector 160, indicative of the absence of a rod within the screw extension assembly 32.

Figure 33:
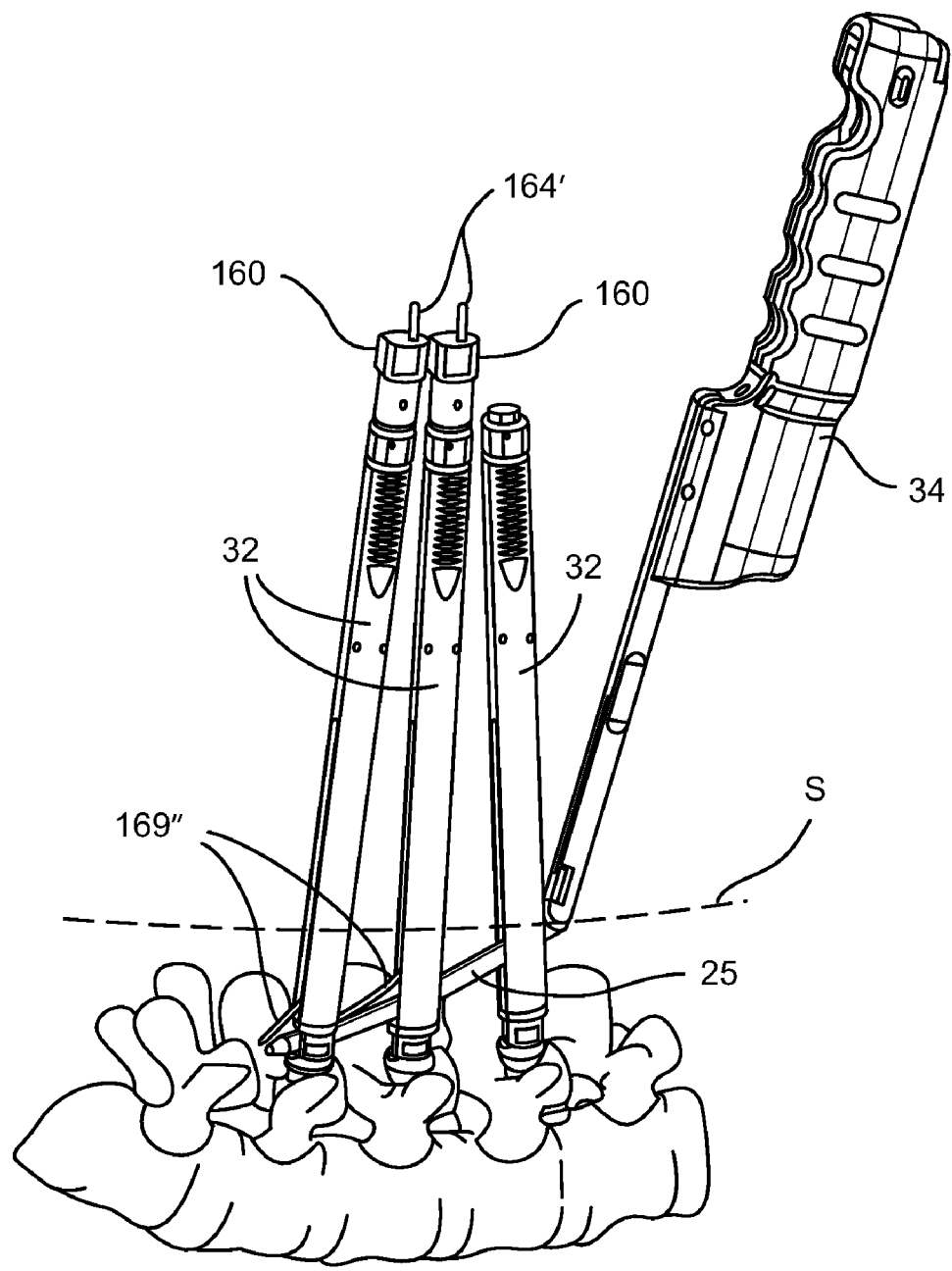
FIG. 33 is a perspective view of the screw extension assembly, rod introducer assembly and rod detector assembly in one position during a procedure disclosed herein.
Figure 34:
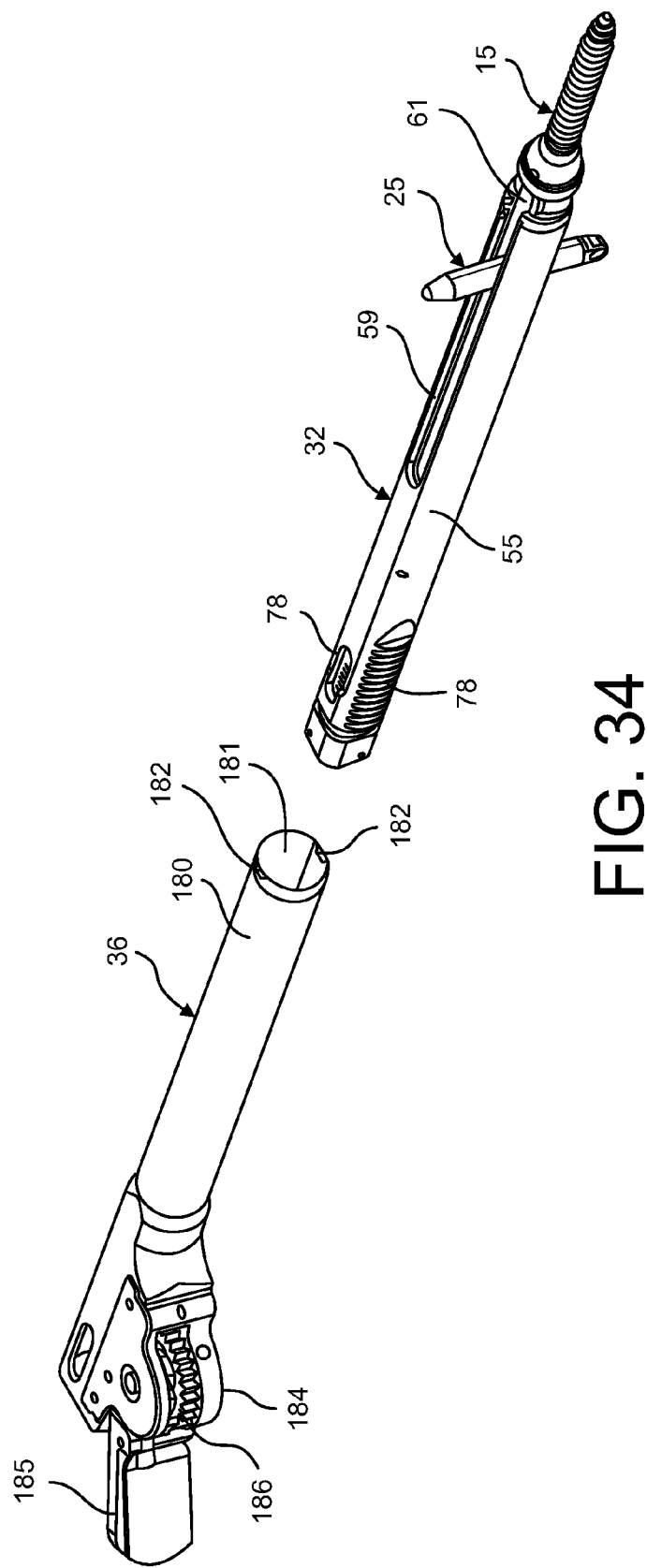
FIG. 34 is a view of a rod introducer assembly and screw extension assembly with a rod disposed therein, prior to mounting the introducer assembly on the extension assembly.

The flag is moved from the neutral position 164 to the positive indication position 164' in response to deflection of the tip 169. Movement of the tip to the position 169' in FIG. 31 is sufficient to cause the flag to shift to the position 164'. The slight movement of the tip is magnified by the pivot mount 174 operating as a fulcrum and the length of the strip 165 terminating in the flag 164. In one embodiment the tip 169 is formed as a thin flexible strip of material, such as Nitinol, that is capable of bending to the position 169". The tip deflects in response to pressure from a connecting rod 25 as shown in FIG. 33. The additional flexibility of the tip 169 allows the tip to be long enough to enter the slot 42 of the yoke 17 and still allow passage of the connecting rod through the screw extension assembly and/or bone screw yoke.

The rod detector 160 may incorporate elements to enforce proper positioning of the detector relative to the screw extension assembly and to temporarily restrain the detector from removal. Thus, the detector may include a guide post 170 extending through the slot 162 in the tubular body to pass through a hole 165a in the strip 165 when the strip is deflected, as shown in FIG. 31. The guide post 170 carries a spring biased positioning ball 171 that extends outward from the tubular body 161 opposite the slot 162. This positioning ball 171 is configured to seat within a positioning groove 176 (see also FIG. 12) defined in the bore 58 of the inner sleeve 57. This feature provides resistance to removal of the rod detector 160 from the screw extension assembly. The base 166a of the cap 166 may be configured complementarily to the proximal end 88 of the inner sleeve, such as in a hex configuration. This feature prevents relative rotation between the rod detector and the screw extension assembly once the detector has been seated within the inner sleeve.

Rod Persuader Assembly

Once a connecting rod 25 is situated at least within the screw extension assemblies 32 at each instrumented vertebral level, the rod must be nestled or seated within the slot 42 of the yoke 17 of each bone screw assembly 15. In the procedures described herein, the rod may be fully seated in the yoke slot by manipulation of the rod introducer assembly 34. This approach is often challenging in part because the rod introduction site is not readily visible or because there are no suitable tactile indicators that the rod is properly seated in every bone screw assembly. In order to ensure proper placement of the rod, a rod persuader assembly 36 may be mounted on one or more of the screw extension assemblies 32 as illustrated in FIG. 3. Details of the rod persuader assembly 36 and its operation can be understood from FIGS. 34-40.

Figure 35:
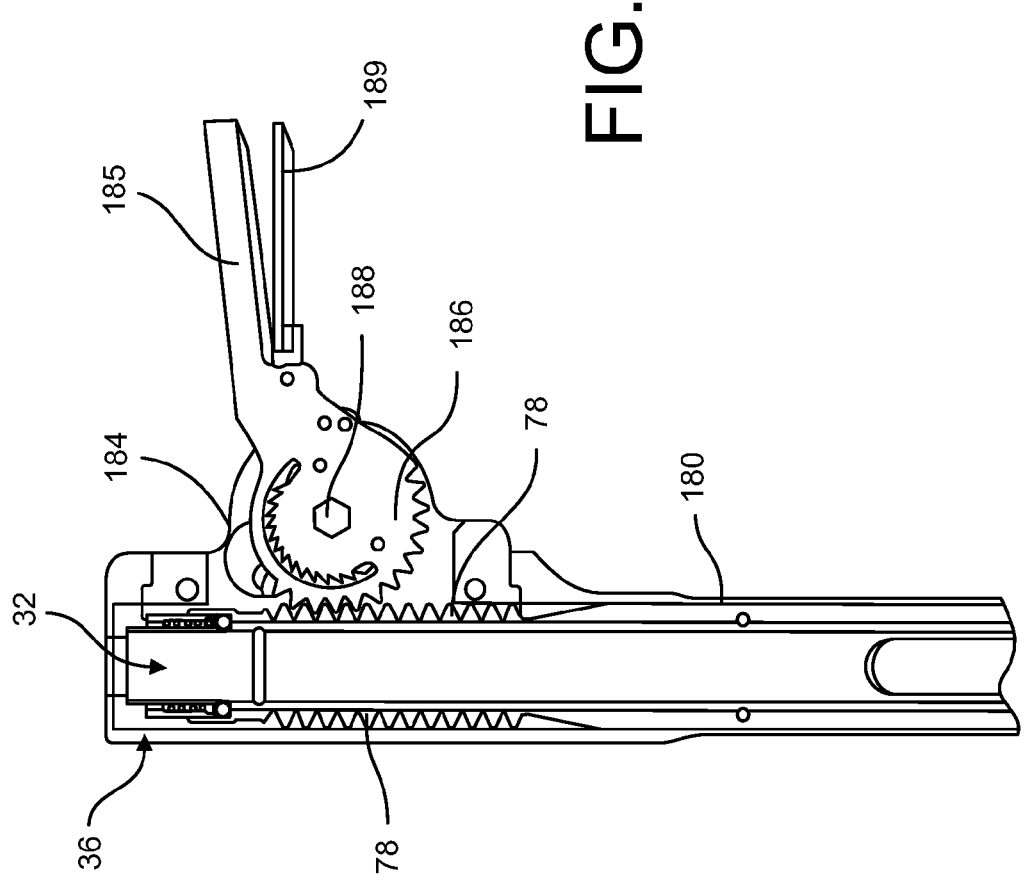
FIG. 35 is an enlarged cross-sectional view of the proximal end of the rod introducer assembly mounted on the screw extension assembly with the introducer assembly in a first position.

The persuader assembly includes an outer tube 180 defining a bore 181 sized to pass over the outer sleeve 55 of the screw extension assembly 32, as shown in FIG. 3. The distal end of the outer tube defines diametrically opposed scallops 182 that are configured to seat on the outer surface of the connecting rod 25 when the persuader is in operation. The persuader includes an advancement mechanism 184 driven by a lever 185. The lever 185 may be connected to or integral with a coupling element 186. The coupling element is arranged and configured to engage a persuader coupling member 78 defined on the outer sleeve 55 of the screw extension assembly 32. In one embodiment the coupling element 186 and coupling member 78 form a rack and pinion arrangement. Thus, as shown in FIG. 35 the coupling element 186 of the rod persuader assembly 36 is a pinion gear while the coupling member 78 of the outer sleeve is the rack. It can thus be appreciated that as the coupling element 186 is pivoted about the pivot hub 188 the pinion gear travels up or down the rack, depending upon the direction of rotation. It is noted that the screw extension assembly includes a coupling member 78 on opposite sides of the outer sleeve 55. The coupling members are arranged at 90 degrees to the rod slot 59. With this arrangement the scallops 182 of the outer tube 180 will contact the connecting rod 25 and the persuader assembly 36 may be coupled to the screw extension assembly 32 on either opposite side.

Figure 38:
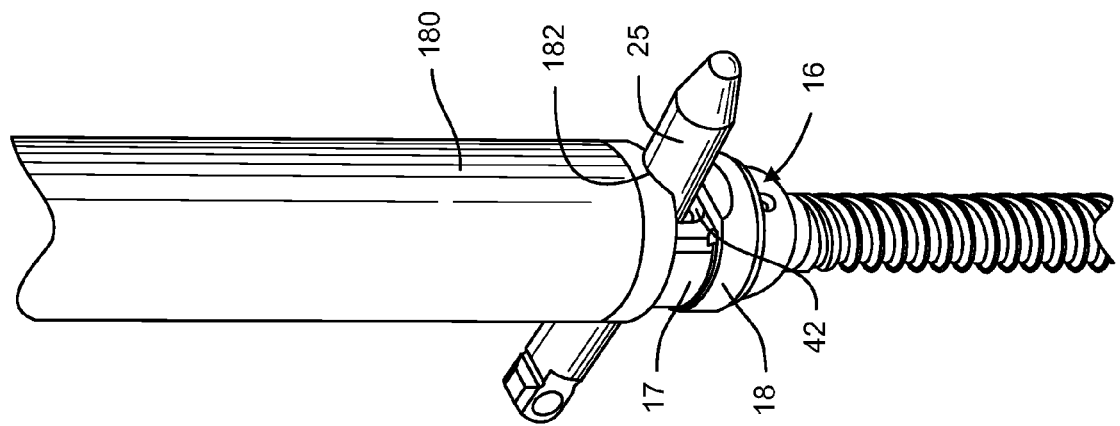
FIG. 38 is an enlarged view of the distal end of the rod introducer assembly in the second position mounted on the screw extension assembly.
Figure 39:
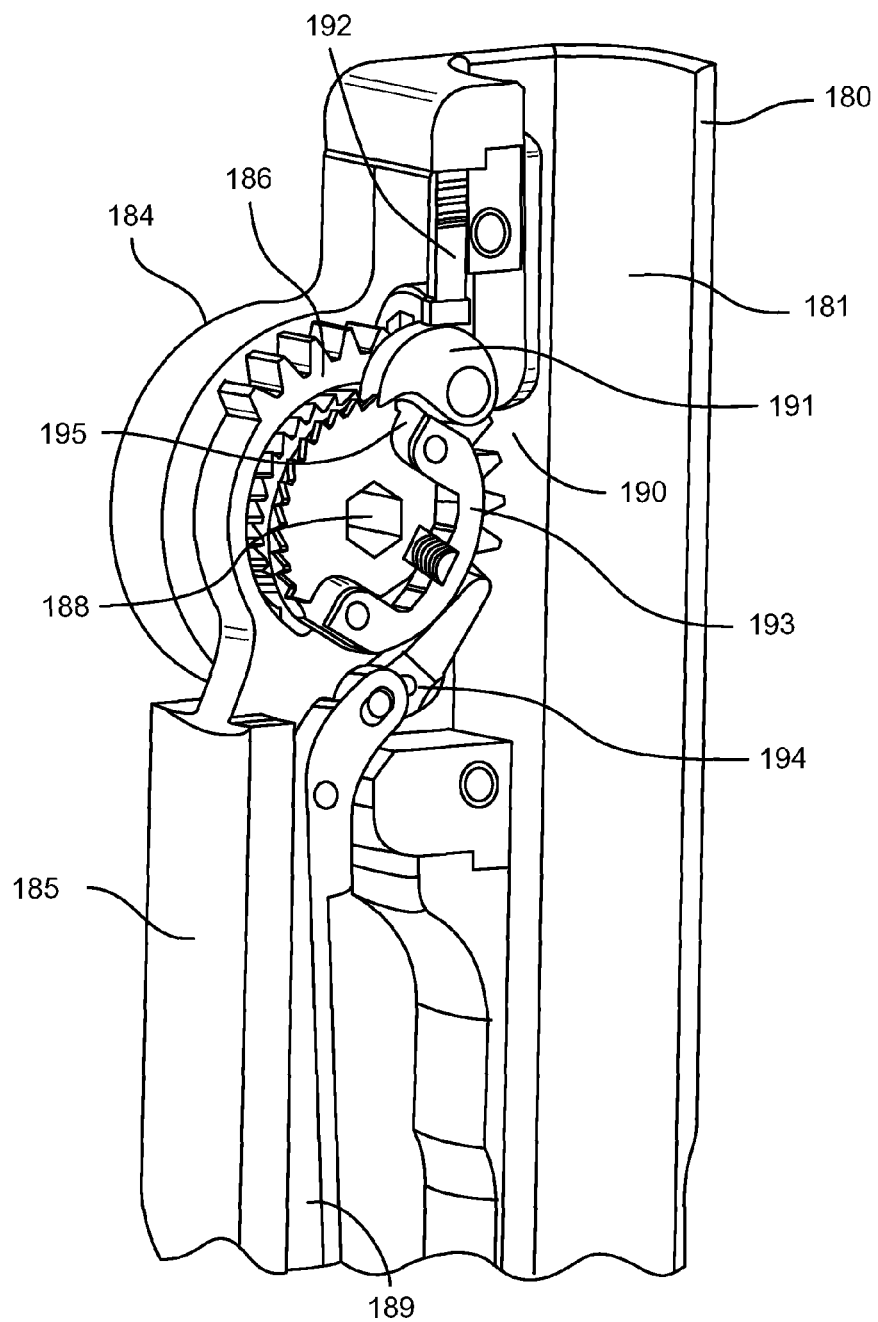
FIG. 39 is an enlarged cut-away view of the advancement mechanism of the rod introducer assembly shown in FIG. 34.

The advancement mechanism 180 may be provided with a release lever 189 that releases a locking mechanism 190 operable to lock the coupling element 186 and coupling member 78, or rack and pinion, in the position shown in FIGS. 38-39. In this position, the outer tube 180 has been advanced the full length of its travel along the outer sleeve 55 so that the scallops 182 contact the connecting rod 25 and force the rod into the slot 42 of the yoke 17 and/or into the sleeve 18 of the screw assembly 15. As shown in FIG. 39, the release lever 189 is connected to a release element 193 by a linkage 194. A pawl 191 is pivotably mounted to the outer tube 180 to engage the pinion gear or coupling element 186 to prevent rotation in one direction while permitting rotation in the opposite direction. The pawl 191 thus prevents rotation of the lever 185 upward to the position shown in FIG. 34 but permits rotation downward from the position in FIG. 35 to the position in FIG. 39. The release element 193 includes a prong 195 that is arranged to push or rotate the pawl 191 away from the coupling element 186, thereby allowing the element (pinion gear) and lever 185 to rotate freely in either direction. Thus, depressing the release lever 189 toward the advancement lever 185 actuates the linkage 194 to push the release element 193 toward the pawl 191. The release element 193 may be spring biased outward from the hub 188, which in turn biases the locking mechanism 190 to the locked position with the pawl 191 in contact with the coupling element 186.

Figure 40:
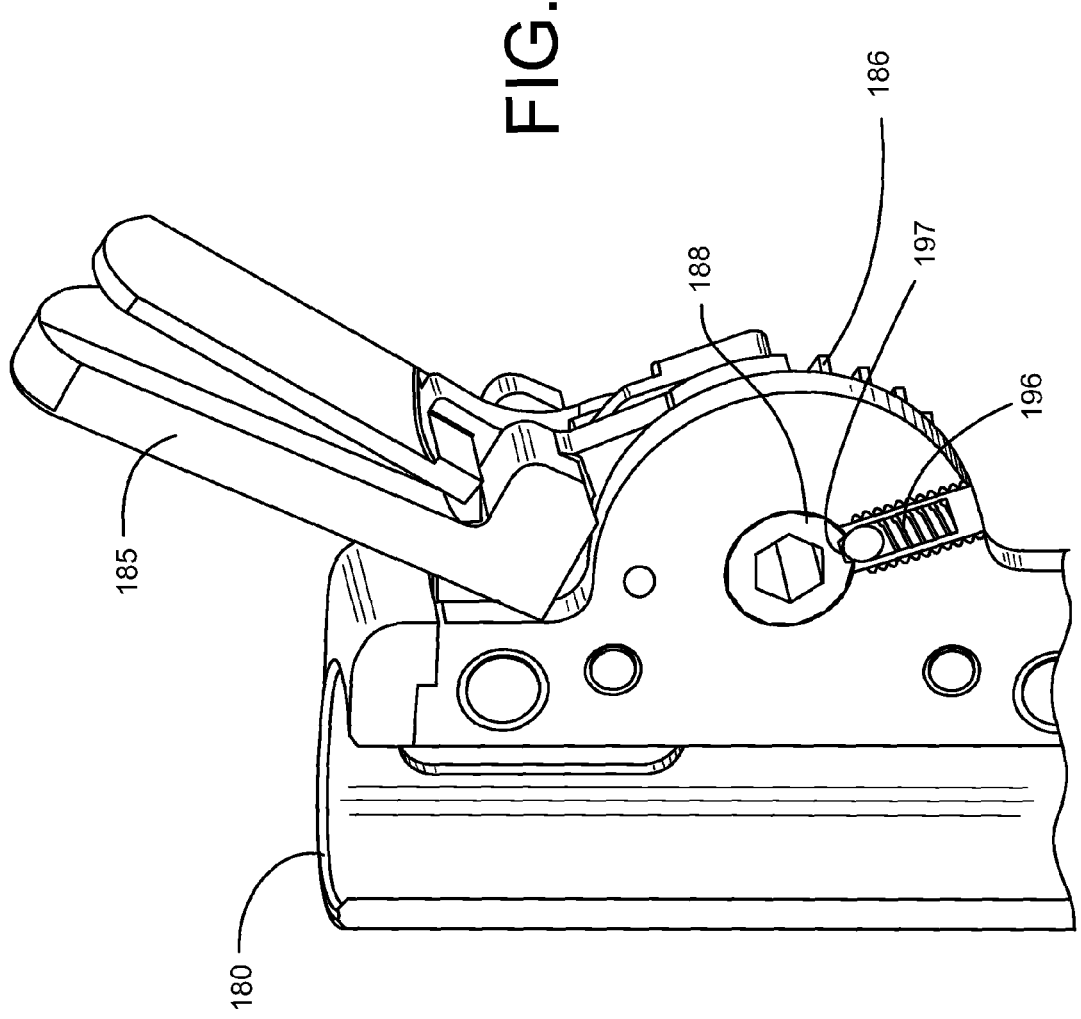
FIG. 40 is an enlarged cut-away view of the advancement mechanism shown in FIG. 39.

The rod persuader assembly 36 may include a feature to temporarily hold the advancement lever 185 in the upward position shown in FIG. 40. In this position the rod persuader assembly and especially the scallops 182 of the outer tube 180 are offset from the yoke 17 and the rod 25. This arrangement may be beneficial in procedures in which the rod persuader assembly is mounted on a screw extension assembly prior to introduction of a connecting rod. This temporary holding feature may be implemented by a spring-biased ball 196 biased toward a detent 197 in the pivot hub 188. The detent 197 is arranged to receive the ball 196 only when the lever 185 is in its upright position. Otherwise the ball simply rolls or slides along the remainder of the pivot hub 188.

Distraction/Compression Instrument

Figure 41:
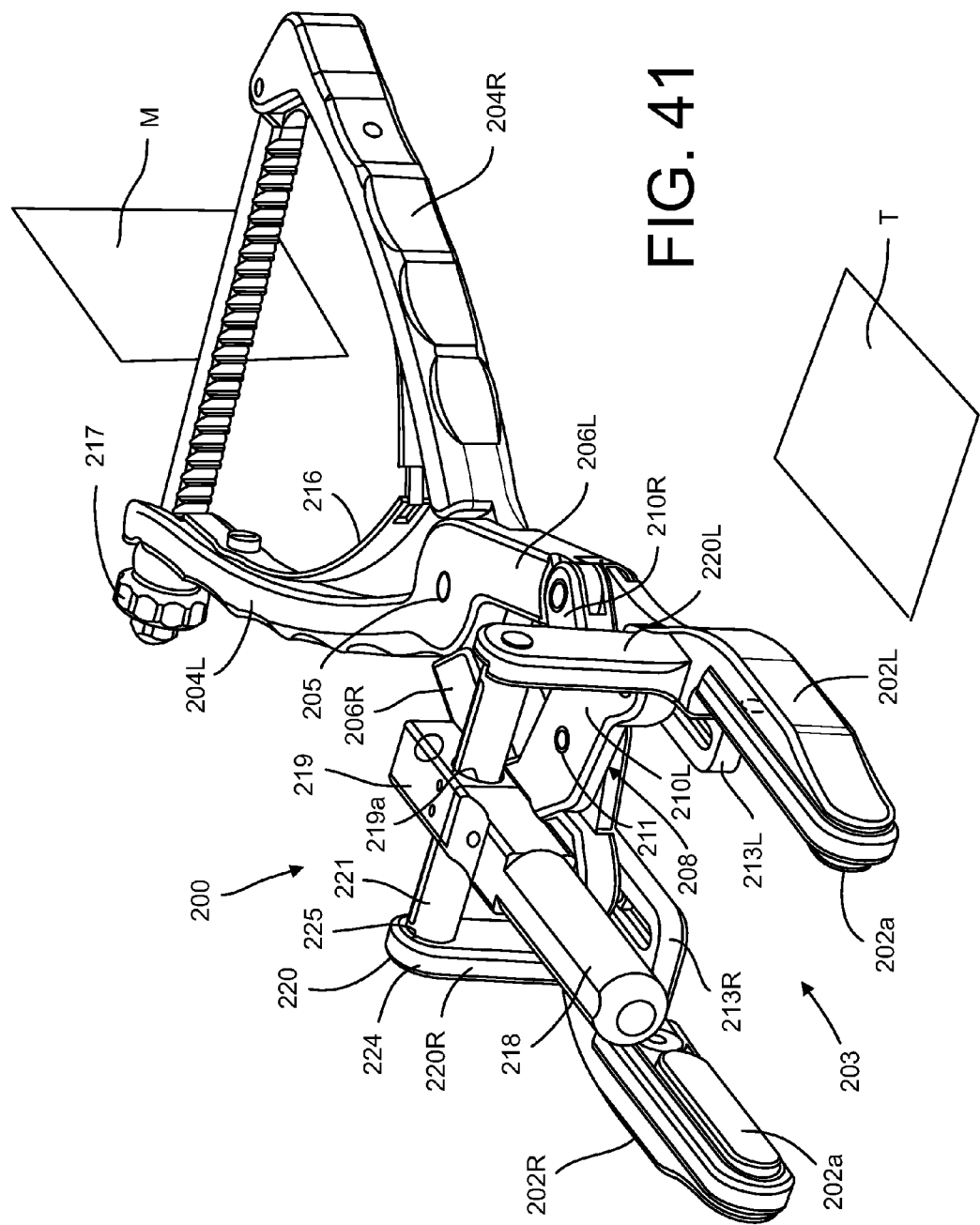
FIG. 41 is a perspective view of a compression/distraction device as disclosed herein, shown with the jaws open and the fulcrum in a first position.
Figure 46A:
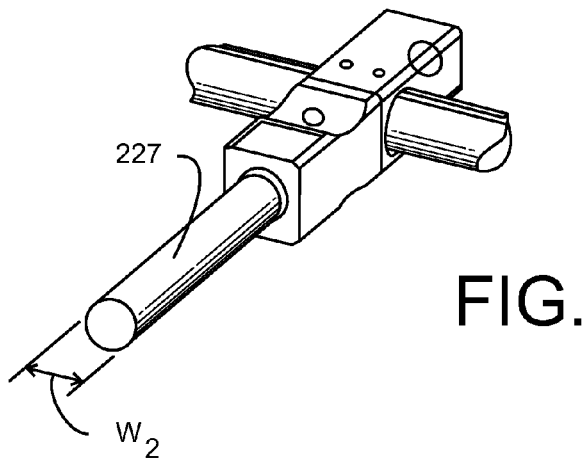
FIGS. 46a-c are perspective views of alternative fulcrums for use with the compression/distraction device shown in FIG. 41.
Figure 46B:
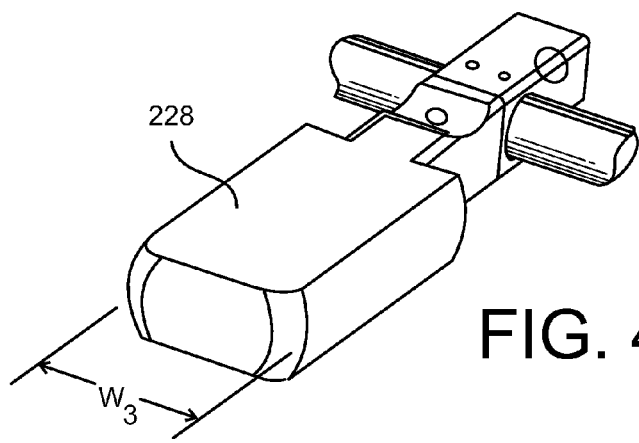
Figure 46C:
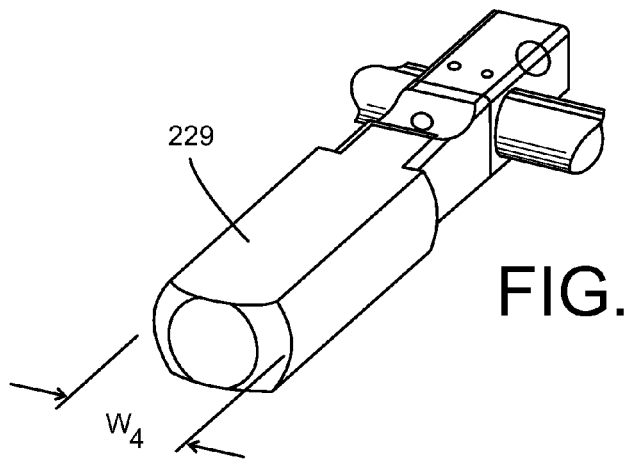
Figure 47:
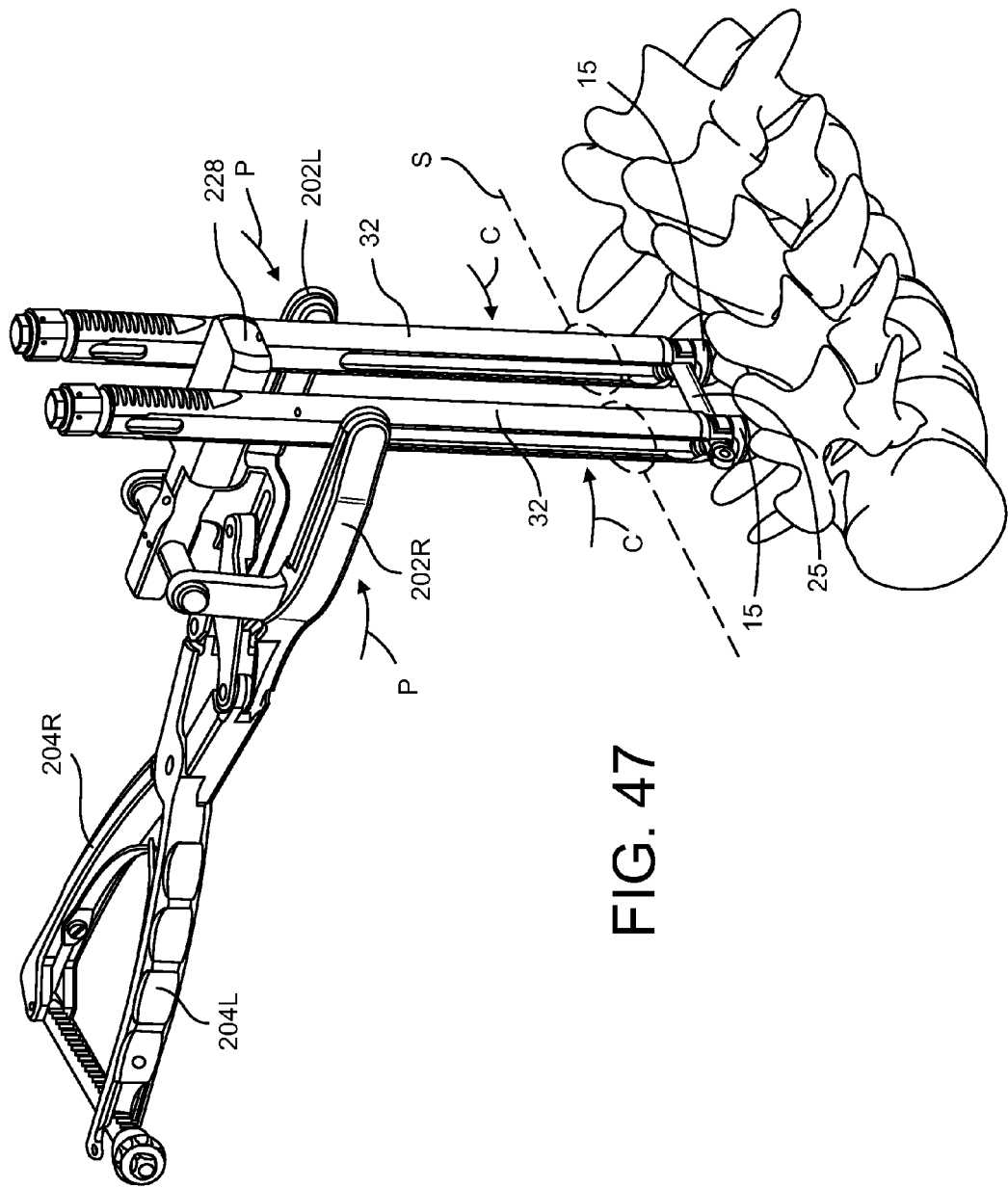
FIG. 47 is a perspective view of the compression/distraction device of FIG. 41 used in a compression procedure.
Figure 48:
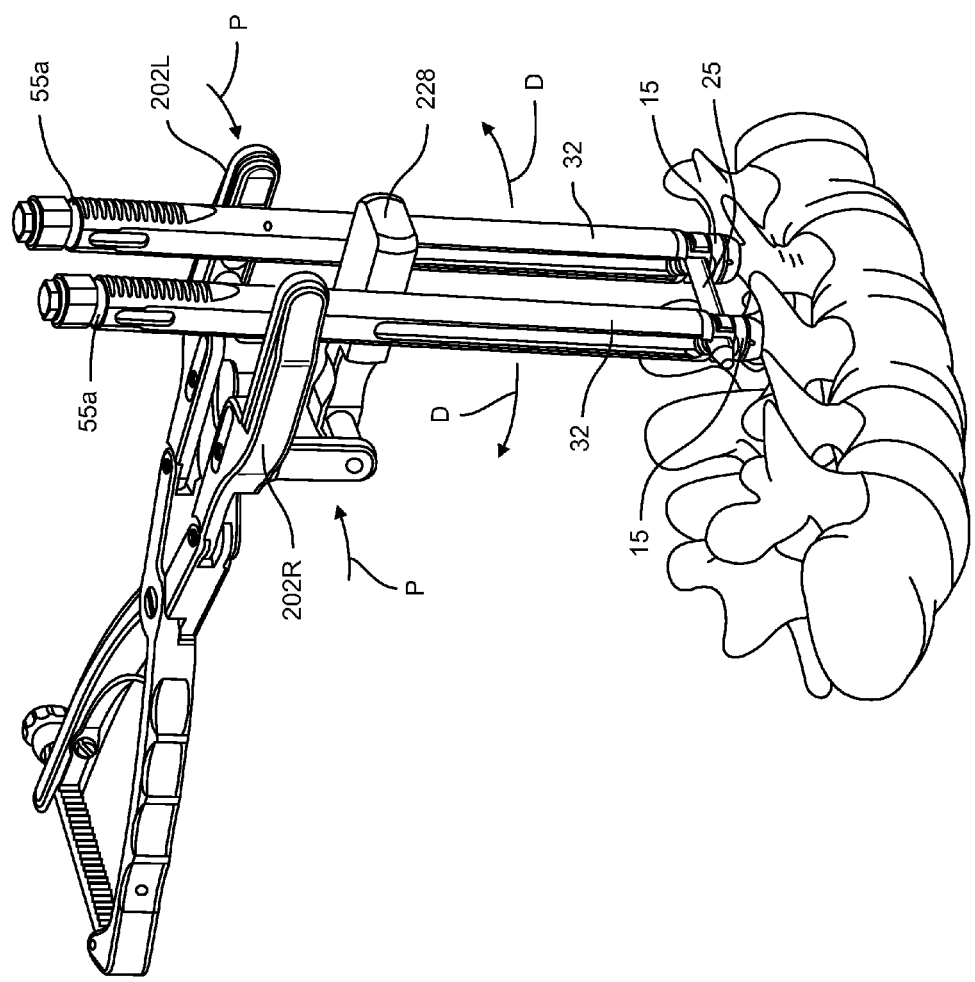
FIG. 48 is a perspective view of the compression/distraction device of FIG. 41 used in a distraction procedure.

A distraction/compression instrument 200 is illustrated in FIGS. 41-46. The assembly is configured to particularly operate on screw extension assemblies of bone screws engaged within adjacent vertebrae as shown in FIGS. 47-48. The instrument 200 includes a pair of opposed jaws 202R and 202L defining a contractible workspace 203 therebetween. (The designation R and L is arbitrary and merely indicative of like components on opposite sides of a midplane M passing along the longitudinal axis of the instrument 200 and between the jaws. (For clarity the R and L designation may not be used when referring to both jaws 202 together). The jaws 202R, L are generally elongate and parallel to each other and define a plane T extending through the jaws 202R, L are perpendicular to the midplane M, as shown in FIG. 41. The jaws may be provided with pads 202a that may be formed of a material adapted to contact the outer sleeve of a screw extension assembly 32 without damaging the sleeve. The pads 202a may also be resilient and/or compressible to modestly embrace the outer sleeves as the jaws 202 are drawn together.

Figure 42:
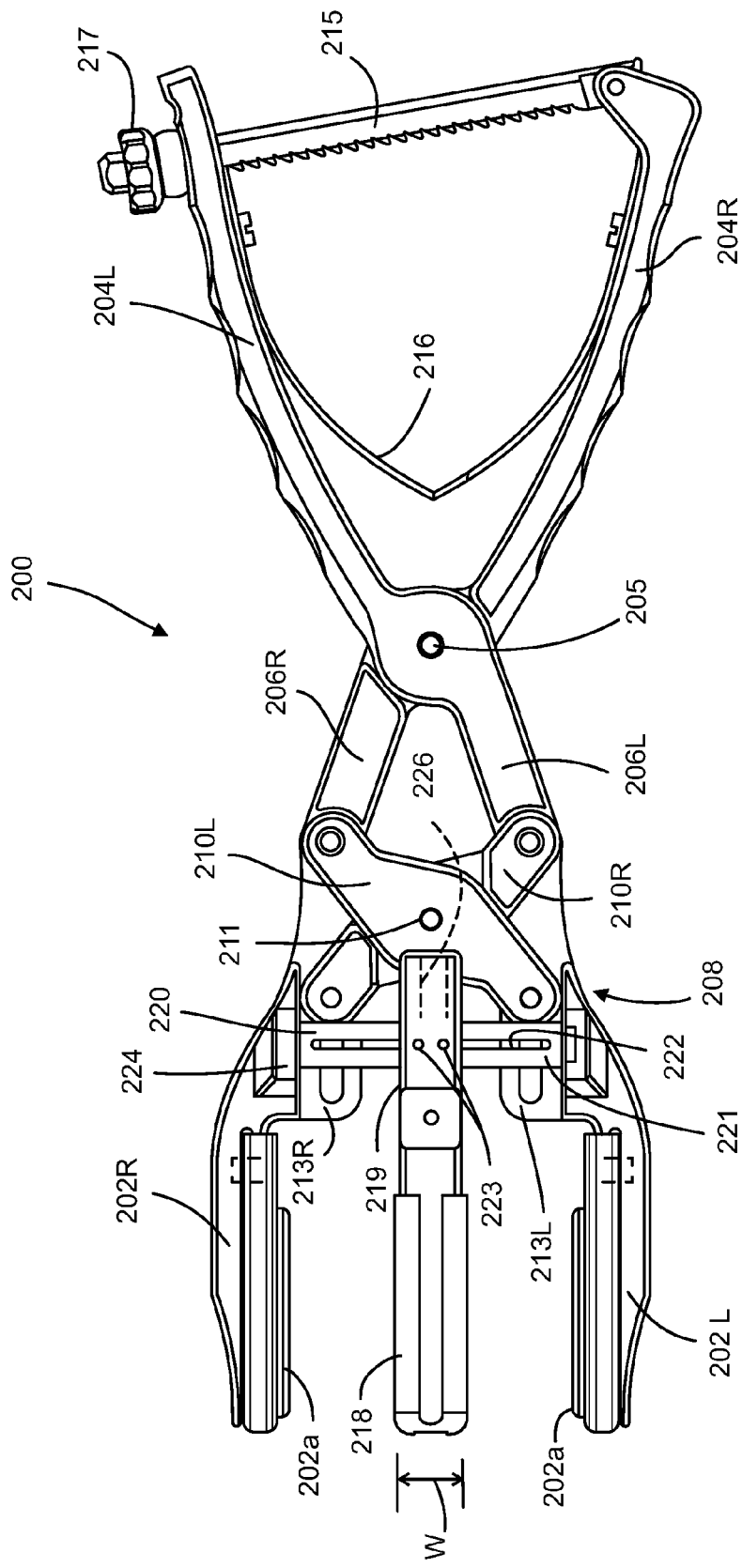
FIG. 42 is a top view of the compression/distraction device shown in FIG. 41.
Figure 43:
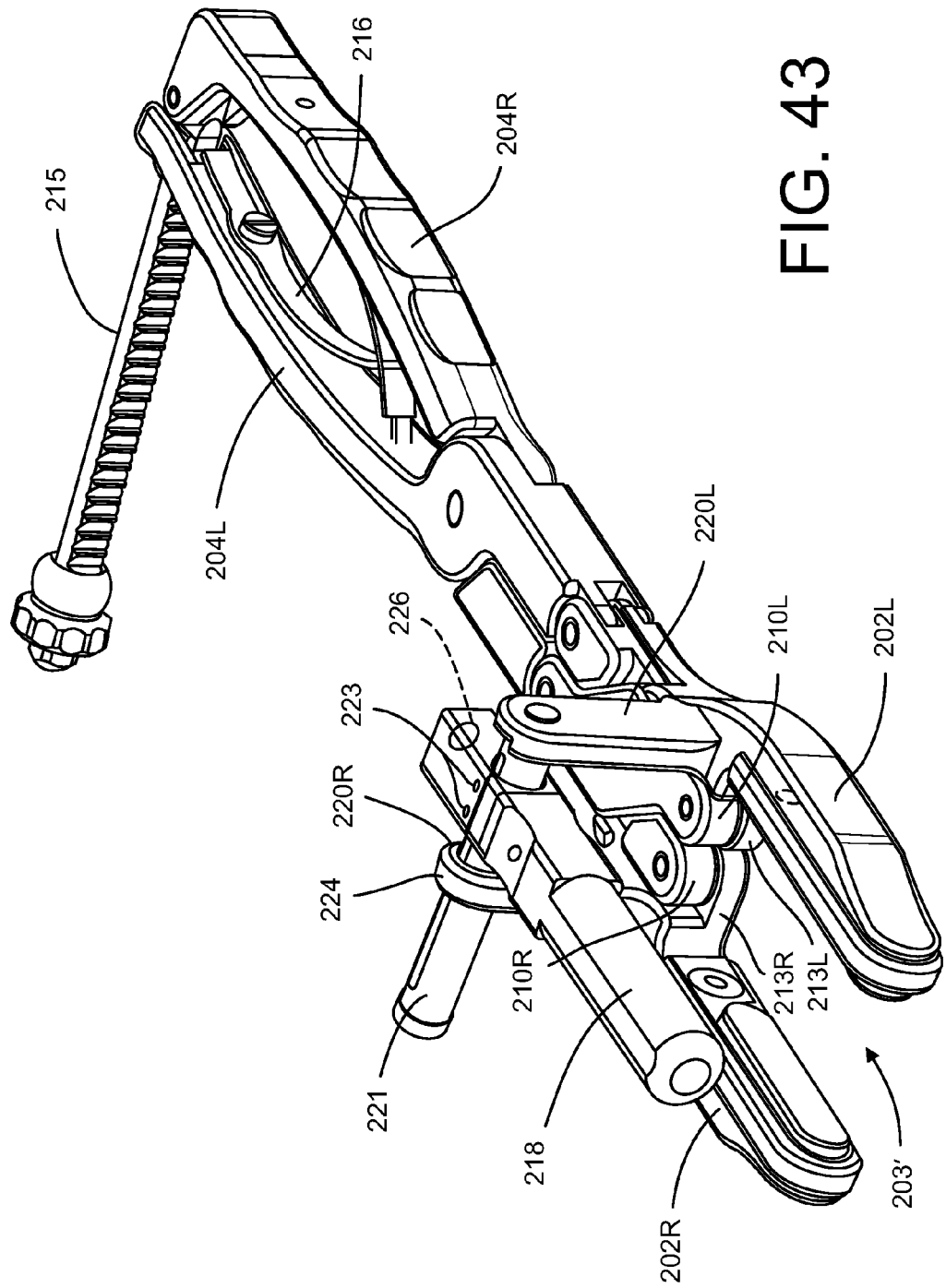
FIG. 43 is a perspective view of the compression/distraction device shown in FIG. 41, shown with the jaws closed.
Figure 44:
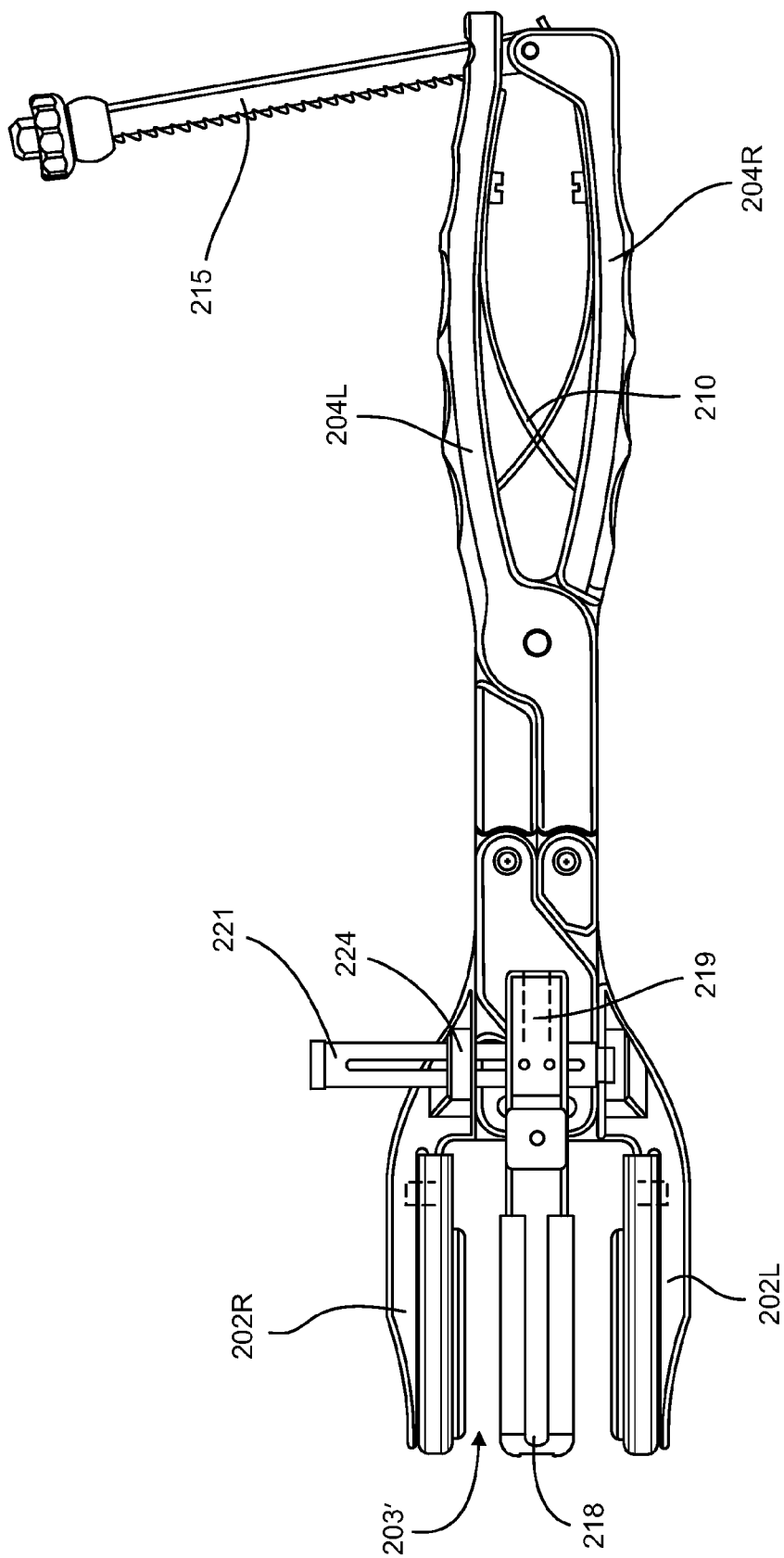
FIG. 44 is a top view of the compression/distraction device shown in FIG. 43, shown with the jaws closed.

The jaws are linked to a corresponding pair of handles 204R, L in a scissors-type configuration—i.e., the handle 204R is on the opposite side of the mid-plane of the apparatus from the corresponding jaw 202R. The handles are pivotably connected at a pivot 205 and with a corresponding linkage arm 206R, L extending beyond the pivot. The two linkage arms 206 are connected to the corresponding jaws 202 by a linkage mechanism 208 that is configured to allow the jaws 202R, L to be drawn together with the facing surface of the jaws or the pads 202a remaining generally parallel to each other and to the mid-plane M of the instrument. The linkage mechanism 208 includes a cross arm 210R, L connecting each linkage arm 206R, L to the corresponding jaw 202R, L, as best seen in FIG. 42. The cross arms 210 are pivotably connected at a pivot 211. The ends of the cross arms 210 are slidably engaged to a guide channel member 213R, L attached to or integral with a corresponding jaw 204R, L. The linkage mechanism 208 is thus configured to so that as the handles 204R, L are squeezed together the cross arms 210R, L slide to the end of the guide channel members 213R, L, as shown in FIG. 43. The cross arms 210 also pivot together, thereby drawing the jaws 202 together and closing the workspace to the reduced configuration 203' shown in FIGS. 43, 44.

An adjustable ratchet mechanism 215 is connected between the ends of the handles 204R, L. The ratchet mechanism is operable to hold the handles in a plurality of positions ranging from the fully open position shown in FIG. 42 to the fully closed position shown in FIG. 43. A leaf spring assembly 116 is disposed between the handles and configured to bias the handles apart. An adjustable stop 217 may be provided on the ratchet mechanism 215 to adjust the span of the fully open position of the handles when they are biased outward by the leaf spring assembly 217. Other mechanisms for biasing the handles and/or holding the handles in a particular position are contemplated.

The compression/distraction instrument 200 includes a fulcrum 218 that provides leverage for the compression or distraction of the vertebrae. The fulcrum includes a base 219 that is mounted on a support 220. One leg 220R of the support is connected to the jaw 202R while another leg 220L is connected to the other jaw 202L. A cross beam 221 is supported by the two legs 220R, L generally parallel to the plane of movement P of the jaws 202, as shown in FIG. 47. The base 219 of the fulcrum 218 defines a bore 219a configured to be slidably mounted on the cross beam 221. The beam 221 may be provided with a guide or anti-rotation slot 222 that receives one or more pins 223 extending from the fulcrum base 219 into the slot. The fulcrum 218 is thus supported in the instrument 200 to allow slidable movement of the axis of the fulcrum 218 in a plane that is spaced above and substantially parallel to the plane T. A plunger or friction pin 226 may be provided in the base 219 that is adapted to frictionally engage or apply pressure to the cross beam 221 in a manner sufficient to hold the fulcrum against shifting or wobbling while still allowing the fulcrum to slide along the beam. The plunger 226 may be adjustable to vary the pressure applied to the cross beam.

The cross beam 221 is affixed or attached to one of the legs, leg 220L for instance. The other leg, leg 220R in this example, includes a collar 224 defining an opening 225 to slidably receive the cross beam 221. Thus, as the jaws 202 move together the collar 224 and more specifically the leg 220R slides along the cross beam, as seen by comparing FIGS. 41 and 43.

As shown in FIGS. 41-45, the fulcrum 218 is in the form of a generally elongate cylindrical rod having an effective width $W_1$. The width of the fulcrum impacts the manner in which the vertebrae are distracted/compressed. Thus, in one aspect, the instrument 200 may be provided with additional fulcrums having different configurations and widths. For instance, the fulcrum 227 shown in FIG. 46a is also cylindrical but has an effective width $W_2$ that is less than the width $W_1$ of the fulcrum 218. Alternatively the fulcrum can be generally rectangular with rounded sides, like the fulcrum 228 and 229 in FIGS. 46b and 46c, respectively. The two fulcrums may have differing widths $W_3$ and $W_4$ that may also differ from the widths $W_1$ and $W_2$. In each of the illustrated embodiments the fulcrums present a rounded surface to contact the screw extension assemblies. The rounded surface facilitates pivoting of the extension assemblies about the fulcrum as described below.

As its name suggests, the compression/distraction instrument 200 may be used to selectively compress or distract adjacent vertebrae that are instrumented with the bone screw assemblies 15 and connecting member/rod 25. Whether the instrument is used to compress or distract depends upon the orientation of the fulcrum, such as fulcrum 228, relative to the jaws 202. Thus, as shown in FIG. 47, the instrument 200 is arranged for compression with the fulcrum 228 above the jaws 202 or, in other words, with the jaws 202 disposed between the fulcrum and the connecting rod 25. In this orientation, when the handles are manually squeezed together the jaws 202 pivot toward each other in the direction of the arrows P. Since the jaws bear against the screw extension assemblies 32 below the fulcrum 228 the extension assemblies pivot about the fulcrum toward each other in the direction of the arrows C. This movement draws the screw assemblies 15 together along the connecting member 25, thereby compressing the adjacent vertebrae to which the screw assemblies are engaged.

When distraction is desired the instrument 200 is inverted—i.e., turned over—so that the fulcrum 228 is between the jaws 202 and the screw assemblies 15, as shown in FIG. 48. In this orientation when the jaws are moved toward each other in the direction P the extension assemblies 32 pivot about the fulcrum so that the distal or lower portion of the assemblies flare outward in the direction of the arrows D. This movement of the extension assemblies slides the screw assemblies 15 along the rod 25, thereby distracting the adjacent vertebrae.

It can be appreciated that the amount of distraction or compression is limited by the angle through which the screw extension assemblies may pivot before contacting each other. For instance, in the compression mode of FIG. 47, the screw extension assemblies 32 will contact each other around the middle of the connecting rod 25. In the distraction mode of FIG. 48, the proximal ends of the assemblies, such as the proximal ends 55a of the outer sleeves of the assemblies, will contact each other when the extension assemblies have pivoted far enough outward in the direction D. The amount of angular movement of the screw extension assemblies that occurs before this contact is affected by the width of the fulcrum. Increasing the width of the fulcrum increases the amount of angular pivoting, and conversely decreasing the fulcrum width decreases the range of extension assembly pivoting.

In addition, the location of the fulcrum along the length of the extension assemblies 32 will also affect the maximum available pivot angle. In the compression mode of FIG. 47, the closer the fulcrum is moved to the screw assemblies 15 or to the surgical incision S the greater the angular range of motion. Conversely, in the distraction mode of FIG. 48, the angular range of motion increases as the fulcrum is moved farther from the screw assemblies or incision.

Figure 45:
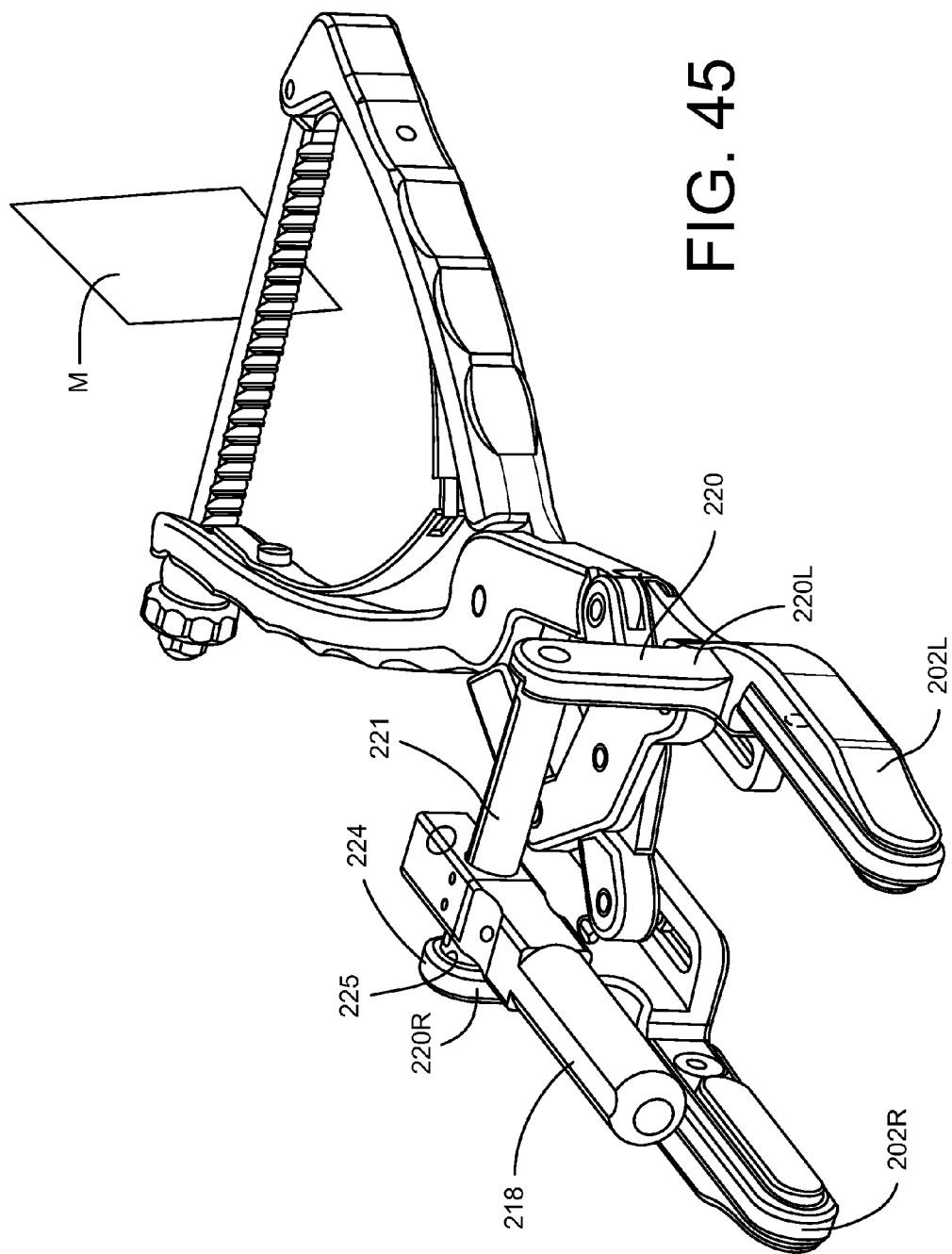
FIG. 45 is a perspective view of a compression/distraction device as disclosed herein, shown with the jaws open and the fulcrum in a second position.

As shown in FIG. 45 the fulcrum, such as fulcrum 218, may be slidably offset from the mid-plane M of the instrument 200. Upon actuation of the instrument the fulcrum will slide along the cross beam 220 as the fulcrum successively contacts the extension assemblies. The sliding of the fulcrum 218 and the use of fulcrums having different widths allow the surgeon more flexibility in handling different sized and spaced vertebrae in patients.

Percutaneous Surgical Procedures

The instruments disclosed herein may be used to percutaneously introduce pedicle screws and a connecting member for multiple level fixation of the spine. The instruments may be used in several different approaches as described with reference to FIGS. 49-57. In each approach the pedicle of the patient is accessed according to known techniques. Guide wires may be used to locate the pedicle of each vertebra to be instrument and to facilitate the subsequent introduction of tools, instruments and implants. Once the guide wires are properly positioned a series of separate incisions I are created to provide a pathway to each pedicle. Thus, in one approach a series of tissue dilators and/or tissue retractors may be introduced over each guide wire to create the pathway to the each pedicle. A final dilator or tissue retractor may remain in position to create the working channel for introduction of the pedicle screw assembly 15 into the corresponding pedicle. The size or diameter of the working channel may be larger if the bone screw assembly is to be introduced with a rod persuader assembly mounted to a screw extension assembly.

Figure 36:
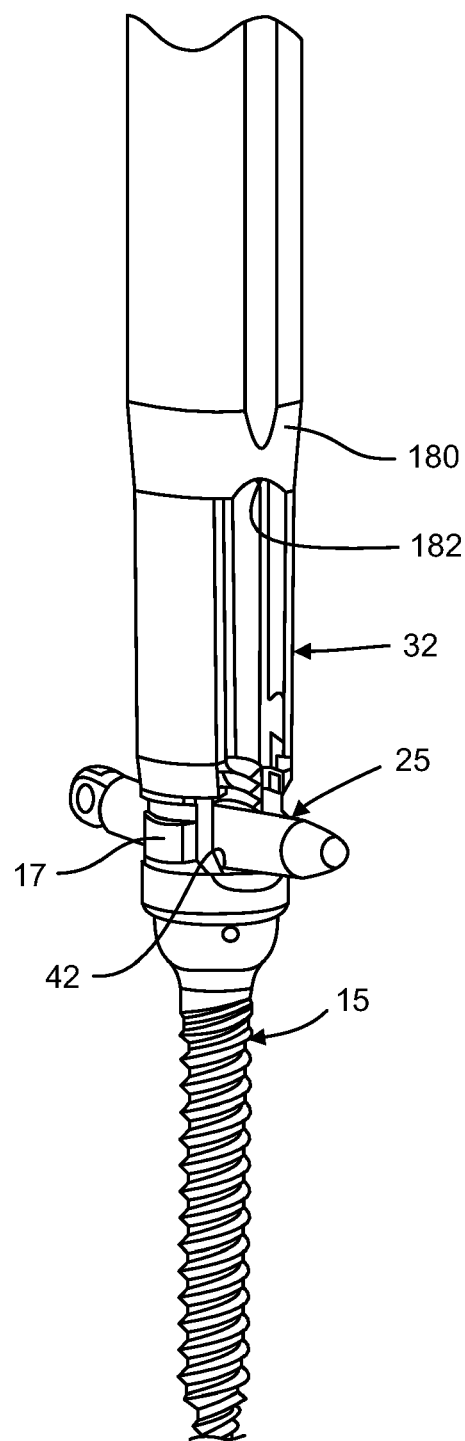
FIG. 36 is an enlarged view of the distal end of the rod introducer assembly in the first position mounted on the screw extension assembly.
Figure 37:
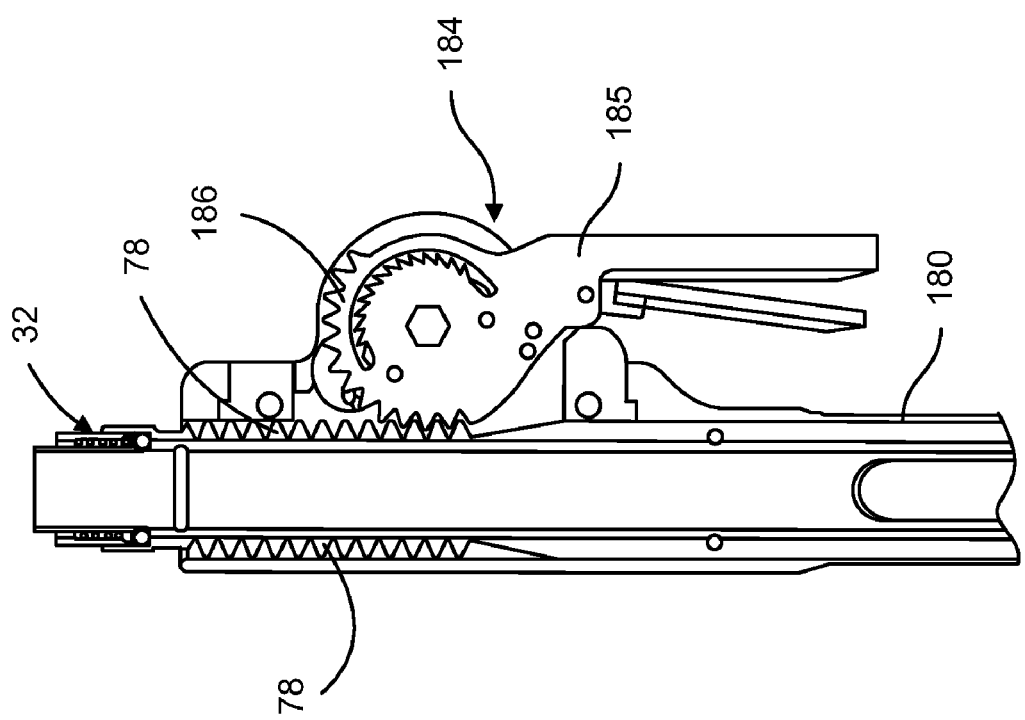
FIG. 37 is an enlarged cross-sectional view of the proximal end of the rod introducer assembly shown in FIG. 35 with the introducer assembly in a second position.

Once the working channel pathway has been created the pedicle is prepared in a known manner for introduction of a bone screw. Thus, the pedicle may be cannulated by a safety awl and then tapped to a suitable depth. A bone screw assembly 15 is engaged to a screw extension assembly 32 as described above and as shown in FIGS. 10-11. With the extension assembly in its locked configuration (see FIG. 16) the yoke 17 of the bone screw assembly 15 is tightly held by the screw extension assembly 32. In some procedures it may be desirable to also mount a rod persuader assembly 36 onto the screw extension assembly 32 as shown in FIGS. 3 and 36. In this instance, the persuader assembly may be locked onto the extension assembly with the advancement mechanism 184 and lever 185 in the position shown in FIG. 37. At this point the instruments are not in a position to receive a connecting rod so there is no need to retract the persuader assembly distal end from the vicinity of the yoke.

Once the screw extension assembly (and alternatively the rod persuader assembly) is engaged to the bone screw assembly 15 the screw driver assembly 100 may be advanced through the bore 58 of the inner sleeve 57 of the extension assembly 32, as depicted in FIG. 19. The shaft 102 may be advanced entirely through the extension assembly and into the screw assembly until the engagement end 103 is seated within the tool engagement recess 22 of the bone screw. The entire assembly, bone screw first, is then advanced along the previously placed guide wire until the bone screw 16 of the screw assembly arrives at the tapped opening in the pedicle. The screw driver assembly 100 may then be used to drive the bone screw into the pedicle until seated. The screw extension assembly 32 may be held by the surgeon while the pedicle screw assembly 15 is driven by the screw driver assembly 100 into the pedicle. When the lower surface of the head 16a of the bone screw seats in the pedicle, the lower portion of the yoke is spaced above the surface of the vertebra allowing unhindered articulation of the yoke and pedicle screw extension assembly 32 which is tightly affixed to the yoke. The depth and positioning of the bone can be verified in a known manner.

Figure 49:
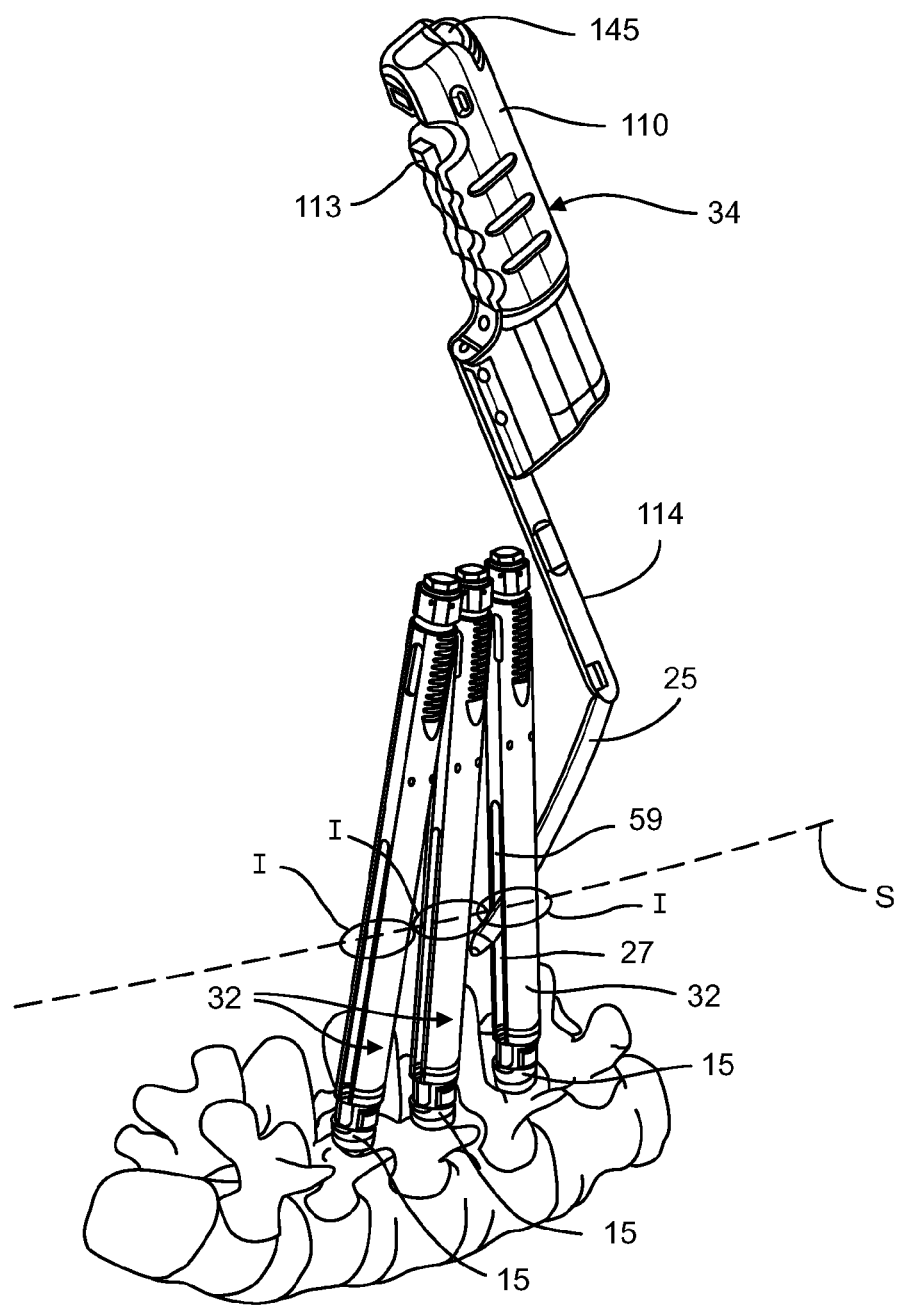
FIG. 49 is a perspective view of one step of one procedure disclosed herein.

Once the pedicle screw position has been verified the screw driver assembly and guide wire may be removed. In a procedure that does not utilize an initially placed rod persuader assembly, the bone screw assemblies 15 and screw extension assemblies 32 will appear as shown in FIG. 49 with each assembly extending through its own incision I. In a procedure in which a persuader is initially placed on at least one screw extension assembly 32 the surgical site will appear as in FIG. 52. The screw extension assemblies 32 may be used to gage the size of the connecting member or rod 25 required to span the instrumented vertebrae. Thus, a known caliper instrument (not shown) may be seated on the outermost extension assemblies to indicate the desired rod length. The proper length rod is selected and contoured as desired. As previously discussed, the pre-bent rod 25 disclosed herein may be used in one orientation for correcting or creating lordosis and in the opposite orientation for correcting or creating kyphosis. More complex bends may be introduced into the connecting rod using a suitable rod bender.

The selected rod is grasped by the rod introducer assembly 34 as shown in FIG. 25 and as described above. As to the proper positioning of the curvature of the rod, for a lordotic curve the rod should curve toward the handle 110 of the introducer assembly, as shown in FIG. 49. For a kyphotic curve the rod should curve in the opposite direction away from the handle. Once the rod orientation has been verified the second locking mechanism 150 of the introducer assembly 34 may be engaged to hold the rod in its "neutral" position, as depicted in FIG. 22. In the neutral position the rod is retained by the introducer assembly but may pivot about the engagement posts 120, as described above in relation to FIGS. 22 and 26. The desired angle of the rod 25 relative to the outer sleeve 114 of the rod introducer assembly 34 may be set and the rod locked by engaging the first lock 140 upon fully depressing the lever 113 (see FIG. 21). In many procedures the rod is initially situated at a 45 degree angle to the outer sleeve 114, as shown in FIG. 49. If it is found during the procedure that a different rod angle is needed, the push button 145 may be depressed to release the first lock 140 and placing the introducer assembly in the neutral position to permit adjustment of the rod angle. Once the new rod angle has been set the lever 113 may be depressed to engage the first lock and tightly grip the rod again.

With the screw assemblies threaded into the pedicles with the screw extensions attached the connecting rod can then be introduced. In certain procedures one or more rod detectors 160 may be placed within one or more screw extension assemblies 32, as illustrated in FIG. 33. In one procedure the rod is introduced through the incision at an extreme cephalad or caudal one of the screw extension assemblies, as depicted in FIG. 49. In this depiction the rod 25 is oriented at a 45 degree angle to the outer sleeve 114 of the rod introducer 34. The introducer is manipulated so that the leading end 27 of the rod 25 passes through the slot 59 of the extension assembly and subsequently or simultaneously through incision I. The slot 59 may act as a guide to slide the distal end 27 of the rod downward through the incision. If necessary the angle of the rod may be adjusted as described above to facilitate entry of the rod through the incision.

Figure 50:
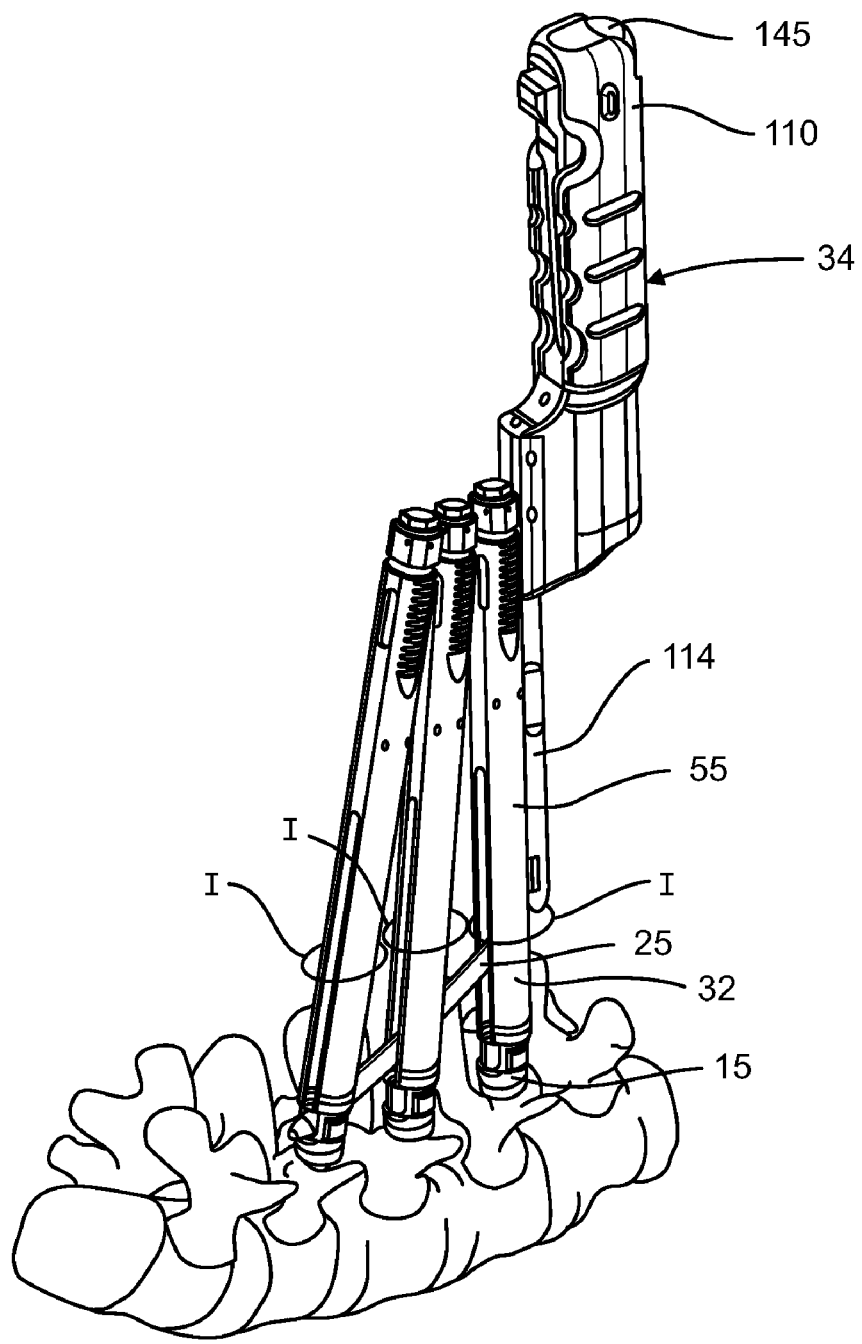
FIG. 50 is a perspective view of a further step of the procedure.

Once below the fascia S the rod can be advanced subcutaneously beneath the fascia toward the other screw assemblies. The sides of the rod slots 59 and 67 in the outer and inner sleeves, respectively, of the extreme screw extension assembly can further act as a guide to keep the rod 25 aligned with the rod slots in the other extension assemblies. As the rod enters the rod slots of the successive extension assemblies the indicator flag 164 (FIG. 33) of the associated rod detector will shift positions to indicate that the rod is within the respective slot. When the rod is fully positioned within each of the screw extension assemblies 32 the outer sleeve 114 of the rod introducer 34 may abut the outer sleeve 55 of the extreme extension assembly, as shown in FIG. 50. The rod detectors may then be removed.

Figure 51:
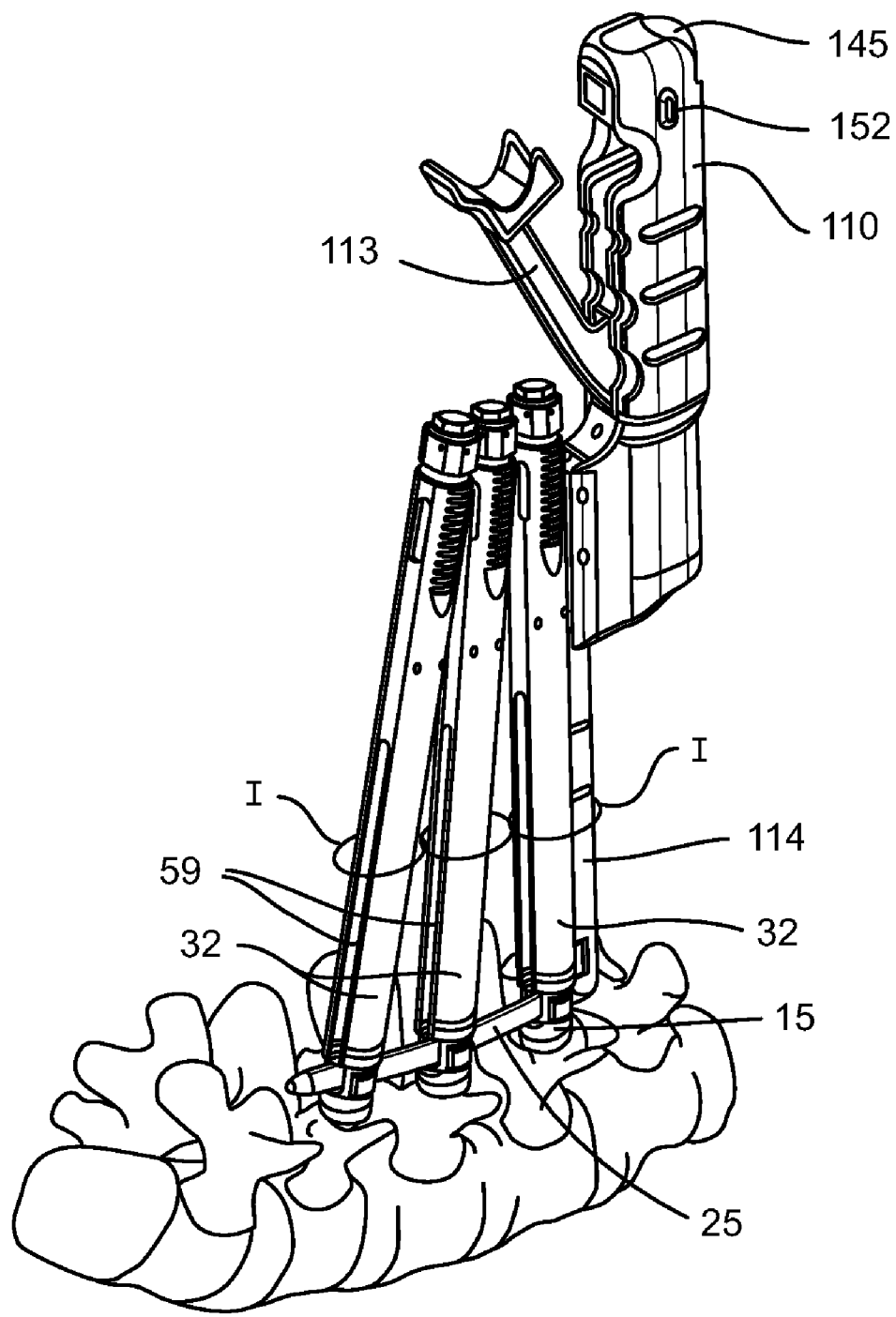
FIG. 51 is a perspective view of an additional step of the procedure.

At this point it is desirable that the rod be oriented at a 90 degree angle to the outer sleeve 114 of the introducer, as illustrated in FIG. 51. Adjustment of the rod angle can be accomplished by depressing the pushbutton 145 to release the second lock and allow the rod to be pivoted relative to the outer sleeve 114. It can be pointed out that due to the construction of the rod introducer the surgeon will receive a tactile indication produced by the rod introducer when the rod has dislodged from the current angular position and re-seated in the new position. In accordance with this particular procedure the rod introducer 34 is the only tool required to seat the rod within the yokes in anticipation of locking the screw assembly with a set screw or a clamping mechanism in accordance with the design of the screw assembly. Consequently, once the rod is fully seated the rod introducer 34 may be disconnected from the rod 25 by depressing the pushbutton 145 to release the second lock and then depressing the release buttons 152 to release the first lock. The actuation lever 113 may then be pivoted outward from the handle 110, as shown in FIG. 51 to spread the flexible legs of the outer sleeve and release the legs from the engagement end 28 of the rod (see FIG. 20). The rod persuader is then withdrawn through the incision.

Figure 52:
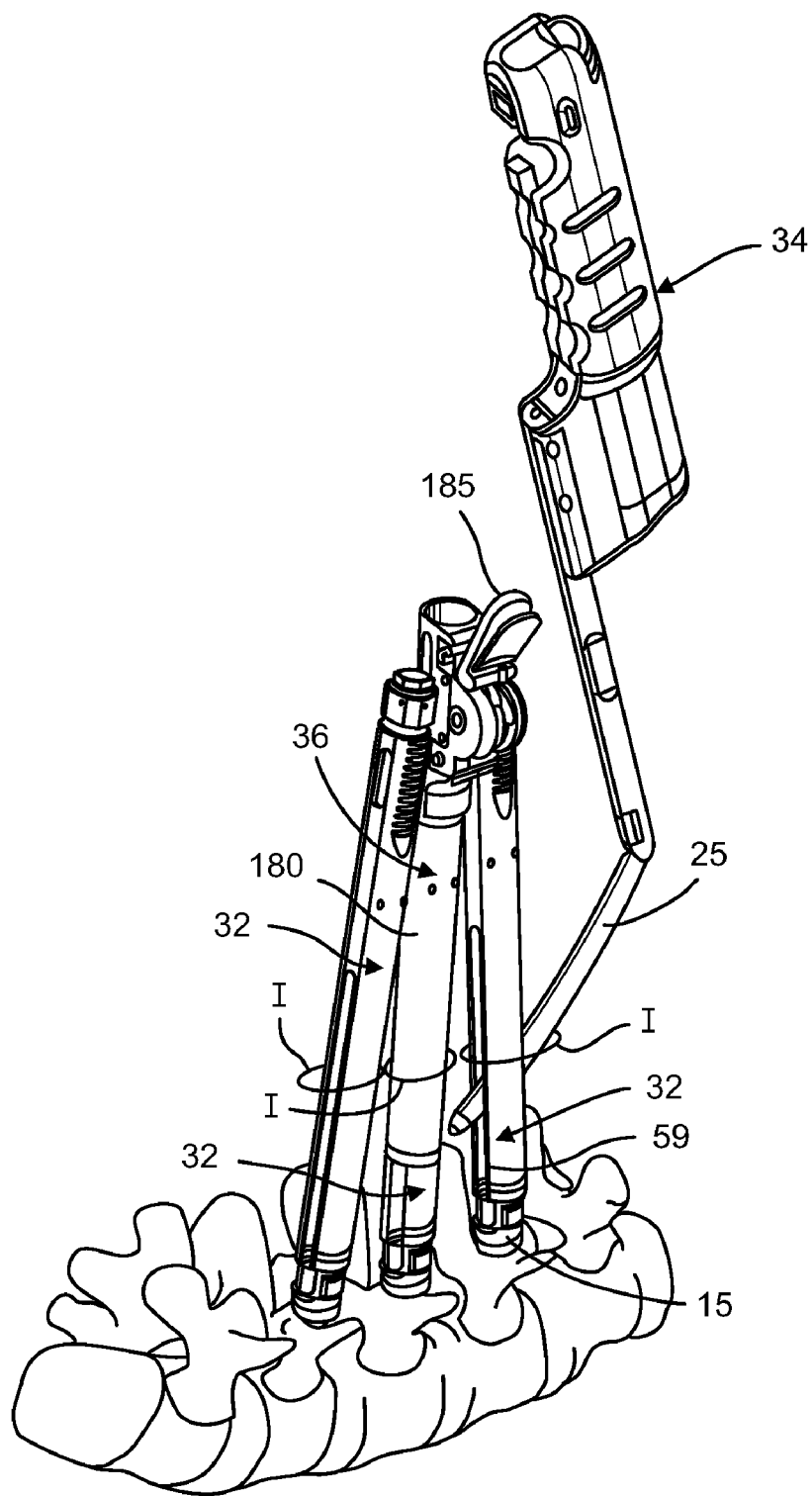
FIG. 52 is a perspective view of one step of another procedure disclosed herein.
Figure 53:
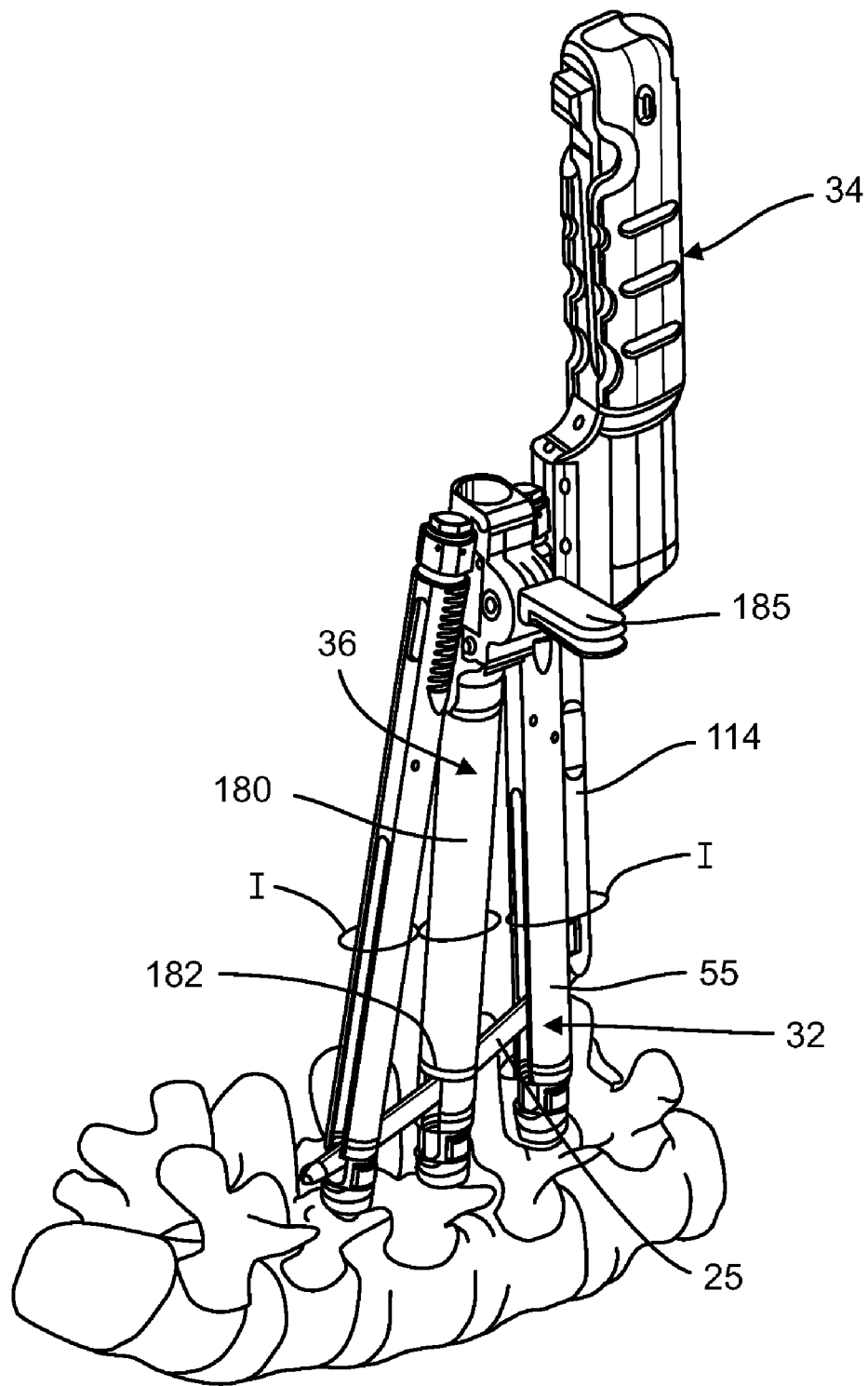
FIG. 53 is a perspective view of a further step of the procedure.
Figure 54:
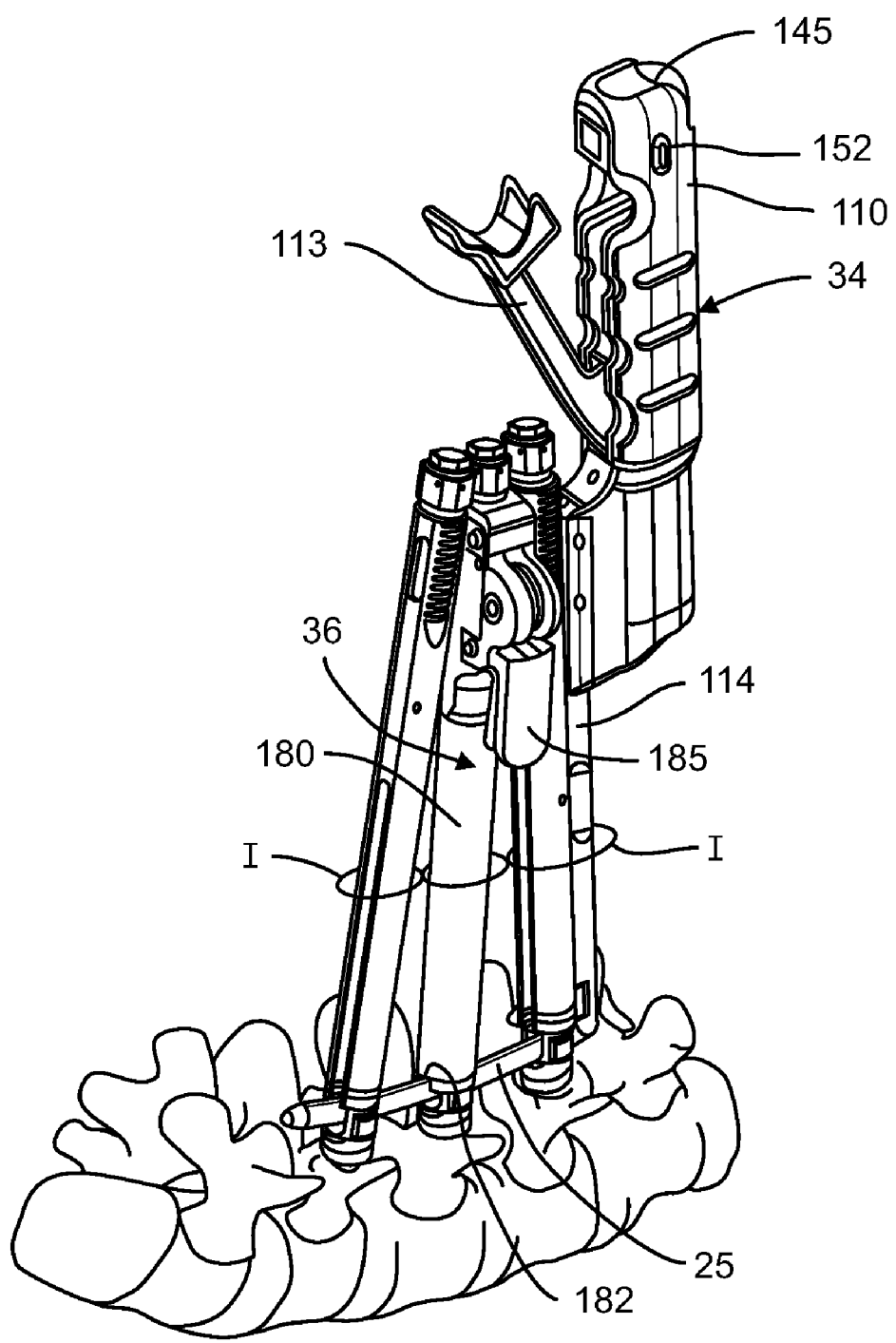
FIG. 54 is a perspective view of an additional step of the procedure.

In an alternative procedure, one or more rod persuaders 36 may be selectively used to seat the rod 25 within the bone screw assemblies 15, as shown in FIGS. 52-54. The rod persuader 36 may be introduced through the incision I with the screw extension assembly 32, as described above, or at the discretion of the surgeon after the screw assemblies and extension assemblies have been engaged to the vertebrae. One or more rod detectors may be positioned as described above. Prior to introducing the rod 25 the rod persuader(s) must be in the retracted position shown in FIG. 52 to avoid interfering with the rod as it enters the rod slots in the screw extension assemblies. Thus, the advancement lever 185 of the assembly 36 is in its upward position. The spring biased ball and detent structure discussed above (FIG. 40) will hold the lever and thus the outer tube 180 in the retracted position.

As shown in FIG. 52 the rod 25 is introduced through the incision I and rod slot 59 at the extreme cephalad or caudal screw assembly 15 and extension assembly 32. Once the rod has been fully advanced through each of the extension assemblies (with the outer sleeve 114 of the introducer 34 abutting the outer sleeve 55) the rod introducer assembly 34 may be moved to the neutral position and the rod persuader assembly 36 can be actuated. The lever 185 is pivoted downward, which drives the outer sleeve 180 downward so that the rod scallops 182 seat on the rod 25, as illustrated in FIG. 53. The advancement lever 185 is pivoted to its lowermost position to drive the outer sleeve 180 fully downward, as shown in FIG. 54. In this position the outer sleeve has pushed the rod 25 to fully seat within the yokes of the screw assemblies. The rod introducer 34 may remain engaged to the rod 25 during this process. Once the rod is fully seated the introducer 34 may be disengaged from the rod as explained above.

Figure 55:
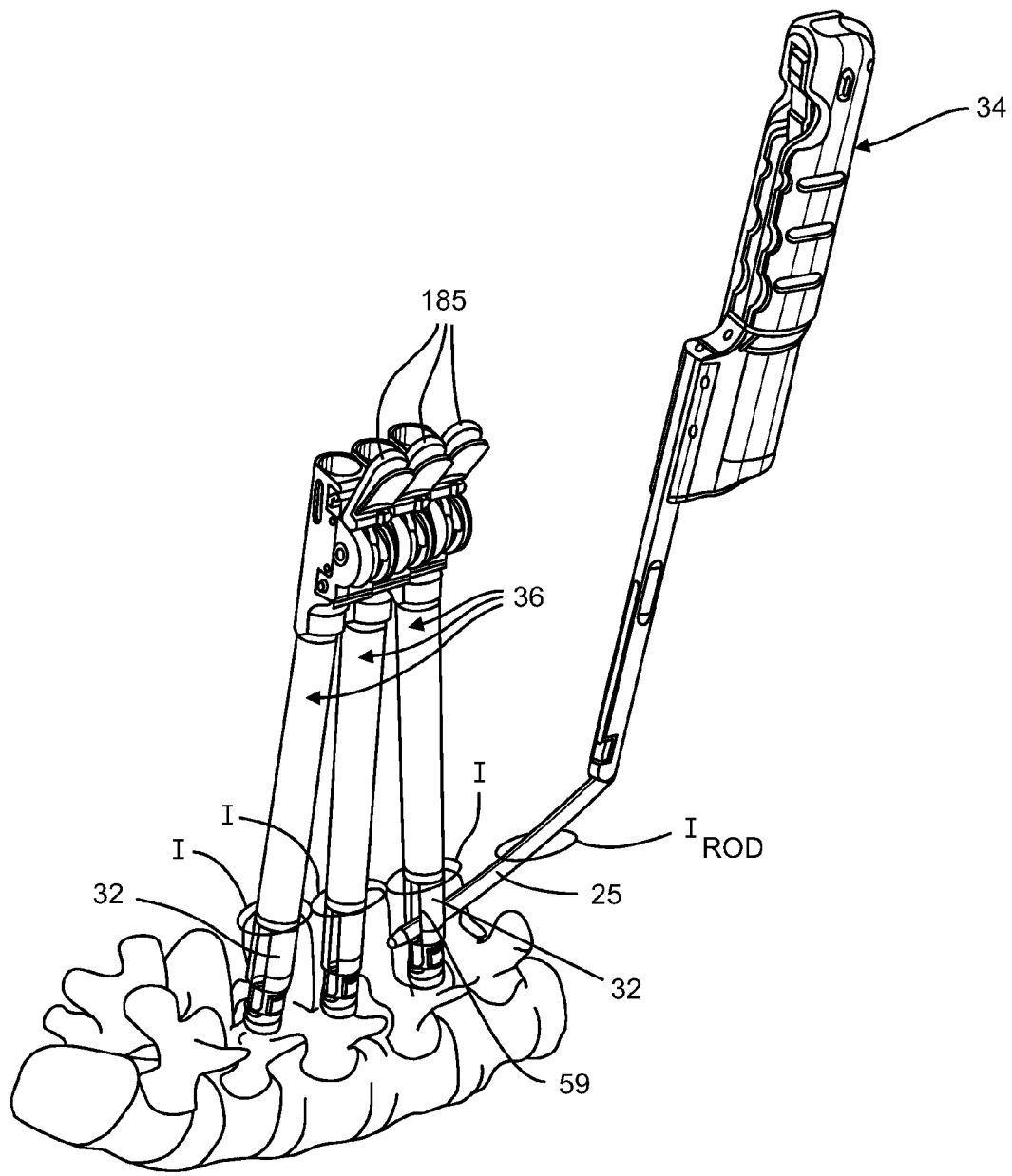
FIG. 55 is a perspective view of one step of yet another procedure disclosed herein.
Figure 56:
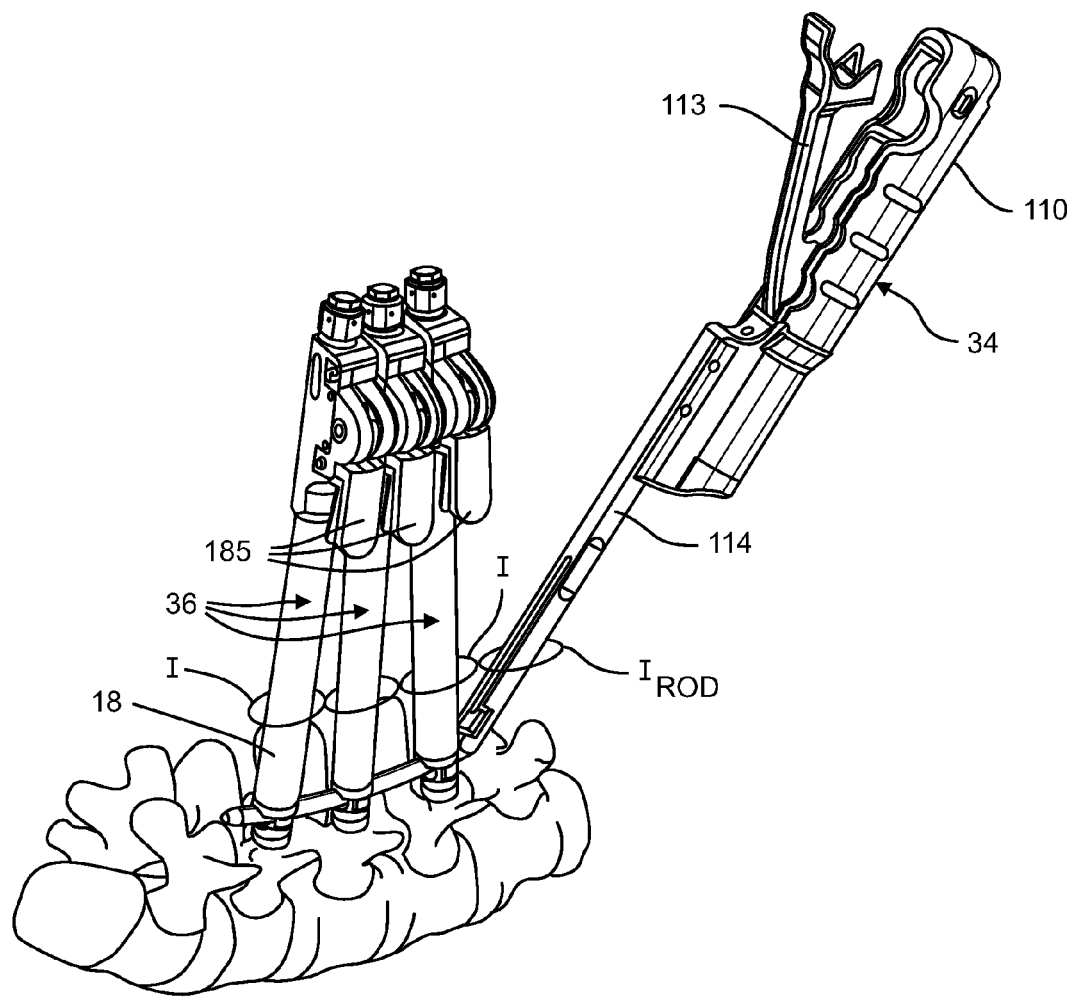
FIG. 56 is a perspective view of a further step of the procedure.

In the procedures just described the rod is introduced exteriorly of the extension assemblies through an incision common with an outermost screw and extension assembly. In an alternative procedure the rod is introduced into the surgical site through a separate incision $I_{rod}$, as illustrated in FIGS. 55-56. This separate incision $I_{rod}$ may be oriented at a 45 degree trajectory with respect to the extreme cephalad or caudal screw extension assembly through which the rod is first introduced. The rod 25 is preferably at the 45 degree orientation relative to the rod introducer 34 as shown in FIG. 55. As shown in FIG. 55 the outer sleeve 114 will pass through the separate incision $I_{rod}$ to guide the rod subcutaneously through each successive extension assembly. With this procedure it may be desirable to position a rod detector within each screw extension assembly to provide a visual indication when the rod enters each assembly.

As shown in FIGS. 55-56 each extension assembly may be provided with a rod persuader assembly 36. Prior to introducing the rod 25 the advancement levers 185 of all the rod persuader assemblies are in their fully retracted positions. Once the rod is in place the levers are pivoted downward to the respective outer sleeves 180 downward to seat the rod in the corresponding yoke. It can be appreciated that the advancement levers may be pivoted simultaneously or sequentially or partially rotated in steps, all with the goal of smoothly seating the rod within each screw assembly 15.

Figure 57:
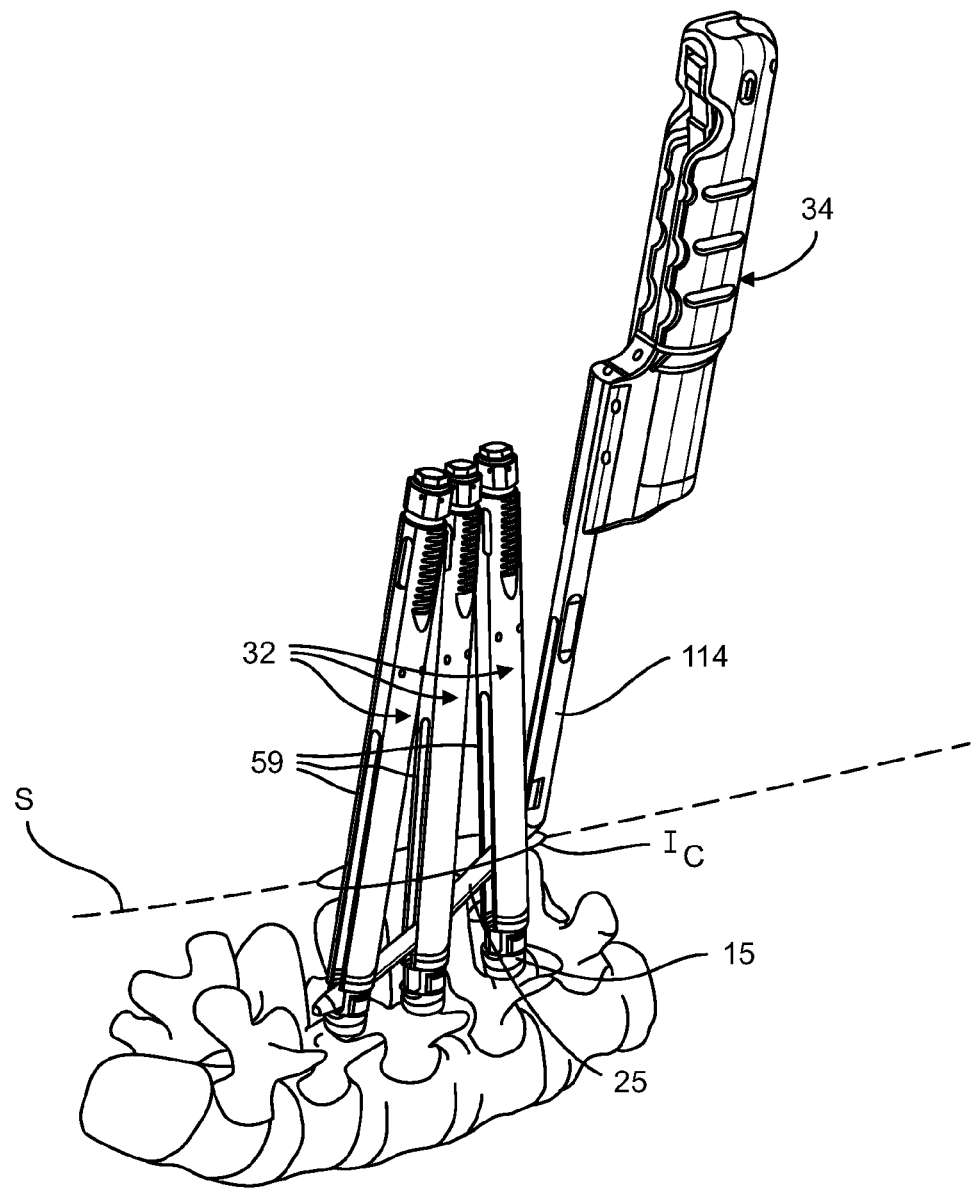
FIG. 57 is a perspective view of an additional step of the procedure.

Another procedure approach is shown in FIG. 57. In this approach a common incision $I_C$ is formed between the separate incisions through which the screw and extension assemblies have been advanced. The rod 25 may be introduced through the rod slots 59 of each extension assembly 32 above the fascia S under direct vision, so that rod detectors are not required. In this approach the rod persuader(s) are not mounted on the screw extension assemblies until after the rod has been properly positioned within the assemblies.

Once the rod has been positioned above the fascia the rod introducer assembly 34 can be manipulated to push the rod through the incision $I_C$ to the position shown in FIG. 57. If necessary the rod angle relative to the outer sleeve 114 may be adjusted, as described above. The rod may be fully seated within the screw assemblies 15 with or without the rod persuader assemblies.

In each approach, once the rod has been fully seated within the screw assemblies the set screw or locking element may be advanced through each screw extension assembly to engage the respective bone screw assembly. In some instances the screw assemblies are finally tightened onto the rod. In other instances compression or distraction may be necessary. In these instances the bone screw assemblies may be provisionally tightened in a manner that permits one or more of the screw assemblies to slide along the connecting rod. The compression/distraction device 200 may be used as described above to perform the necessary adjustments to the screw assemblies, after which the assemblies may be finally tightened. After the rod and screw fixation construct is complete the screw extension assemblies can be removed and the incisions closed.

While the invention has been illustrated and described in detail in the drawings and foregoing description, the same should be considered as illustrative and not restrictive in character. It is understood that only the preferred embodiments have been presented and that all changes, modifications and further applications that come within the spirit of the invention are desired to be protected.

What is claimed is:

1. A surgical instrument for the distraction or compression of bones or bone portions, comprising:
    a pair of elongate cross members pivotally coupled for relative movement having at one end a respective pair of handles and at the other end a respective pair of jaws, said jaws being generally parallel to each other and defining a first plane within which said jaws are relatively movable, the space on both sides of said plane and between said jaws defining a work space;
    a pivot coupling said cross members such that as said handles are squeezed together said jaws are drawn together for both distraction and compression; and
    a fulcrum supported by at least one of said cross members in a fixed second plane spaced from and generally parallel to said first plane, said fulcrum projecting into said work space and having an axis spaced from said jaws and lying in said second plane.

2. The surgical instrument of claim 1, wherein said pivot includes a mechanism that allows movement of said jaws toward each other.

3. The surgical instrument of claim 2, wherein said mechanism couples said jaws to said handles to cause said jaws to move toward each other when said handles are moved toward each other.

4. The surgical instrument of claim 3 wherein said mechanism comprises a linkage between said handles and said jaws.

5. The surgical instrument of claim 4, further including a ratchet mechanism operably connected between said handles to hold said cross members and thereby said jaws in fixed relative positions.

6. The surgical instrument of claim 4, further including a rubber pad on each surface of said jaws facing each other.

7. The surgical instrument of claim 1, wherein said fulcrum is adjustably movable in said second plane spaced from said jaws.

8. The surgical instrument of claim 6, wherein said fulcrum is supported for sliding movement within said second plane.

9. The surgical instrument of claim 6, wherein said fulcrum defines a width within said second plane, said width lying in a generally the same direction as the direction between the jaws.

10. The surgical instrument of claim 9, wherein said width of said fulcrum is adjustable.

11. The surgical instrument of claim 10, wherein said fulcrum includes one of a plurality of elongate bars each having different widths.

12. The surgical instrument of claim 11, wherein said fulcrum includes an adapter to permit selective connections of one of said bars thereto.

13. A method of selectively compressing or distracting bones or bone portions during surgery comprising the steps of:
    providing a surgical instrument having a pair of jaws pivotally movable relative to each other in a first plane, the space on both sides of said plane and between said jaws defining a work space, the instrument including a fulcrum projecting into said work space, said fulcrum being supported by said instrument in a fixed second plane spaced from and generally parallel to said first plane and having an axis spaced from said jaws and lying in said second plane; and
    pivotally operating said jaws with said instrument selectively being in a first position or a second position, said fulcrum in said first position being in a first orientation with said jaws being disposed between said fulcrum and the bones or bone portions to cause compression, said second position being the inverse of said first position, said fulcrum in said second position being in a second orientation between said jaws and said bones or bone portions to cause distraction.

14. The method of claim 13, wherein said jaws are moved in the same direction with the surgical instrument being in the first position and the second position.

15. The method of claim 14, wherein said jaws are moved toward each other.

16. A method of selectively compressing or distracting vertebral bodies in a patient during percutaneous surgery, comprising the steps of:
    providing a surgical instrument having a pair of jaws pivotally movable relative to each other in a first plane, the space on both sides of said plane and between said jaws defining a work space, the instrument including a fulcrum projecting into said work space and being supported by said instrument in a fixed second plane spaced from and said first plane, said fulcrum having an axis spaced from said jaws and lying in said second plane;
    coupling a pair of elongate extensions to one each of respective vertebral bodies of the spine, said extensions each having a length to project outwardly of the exterior surface of said patient;
    inserting said fulcrum between and in a direction generally transverse to the longitudinal axis of said extensions with said jaws disposed exteriorly of said extensions; and
    pivotally moving said jaws relatively toward each other to contact said extensions and pivot said extensions about said fulcrum to cause one of compression and distraction of said vertebral bodies, whereby said surgical instrument is placed in a first position to cause compression and is inverted to a second position to cause distraction.

17. The method of claim 16, wherein said fulcrum is placed more exteriorly from the exterior surface of the patient than the first plane of said jaws to cause compression of the vertebral bodies.

18. The method of claim 16, wherein said fulcrum is placed less exteriorly from the exterior surface of the patient than the first plane of said jaws to cause distraction of the vertebral bodies.

19. The method of claim 16, wherein said fulcrum is adjustably movable in a second plane spaced from and substantially parallel to first plane of said jaws.

20. The method of claim 19, wherein said fulcrum adjustability is practiced by sliding said fulcrum on an instrument support, said fulcrum sliding in a second plane substantially parallel to the first plane of said jaws.

21. The method of claim 20, wherein said fulcrum defines a width within said second plane, said width lying in a direction generally the same as the direction between said jaws, said width being adjustable.

22. The method of claim 21, wherein said fulcrum width adjustably is practiced by selectively interchanging a plurality of bars each having different widths into an adapter supported by said instrument.

23. The surgical instrument of claim 1, further including a beam affixed to at least one of said cross members in a fixed position spaced from, generally transverse to said jaws and of extent to extend form one jaw to the other jaw, said fulcrum projecting from said beam into said work space.

24. The surgical instrument of claim 23, wherein said fulcrum includes a base mounted on said beam.

25. The surgical instrument of claim 24, wherein said base is slidably mounted on said beam.

26. The surgical instrument of claim 1, wherein at least a portion of each of said handles moves in a plane parallel to said first plane.

27. The surgical instrument of claim 26, wherein said at least a portion of each of said handles lies between said jaws and said pivot.

28. The surgical instrument of claim 26, wherein said at least a portion of each of said handles lies in said first plane.

* * * * *